(12) United States Patent
Ginn et al.

(10) Patent No.: US 12,115,077 B2
(45) Date of Patent: Oct. 15, 2024

(54) SYSTEMS, APPARATUS AND METHODS FOR STABILIZING SACROILIAC JOINTS

(71) Applicant: Tenon Medical, Inc., Los Gatos, CA (US)

(72) Inventors: Richard S Ginn, Powhatan, VA (US); Richard Brown, Colorado Springs, CO (US)

(73) Assignee: Tenon Medical, Inc., Los Gatos, CA (US)

( * ) Notice: Subject to any disclaimer, the term of this patent is extended or adjusted under 35 U.S.C. 154(b) by 0 days.

(21) Appl. No.: 18/612,032

(22) Filed: Mar. 21, 2024

(65) Prior Publication Data

US 2024/0261107 A1    Aug. 8, 2024

Related U.S. Application Data

(63) Continuation-in-part of application No. 17/899,693, filed on Aug. 31, 2022, which is a continuation of
(Continued)

(51) Int. Cl.
*A61F 2/30* (2006.01)
*A61B 5/055* (2006.01)
(Continued)

(52) U.S. Cl.
CPC .......... *A61F 2/30988* (2013.01); *A61B 5/055* (2013.01); *A61B 5/062* (2013.01);
(Continued)

(58) Field of Classification Search
CPC .......... A61F 2/4455; A61F 2002/30121; A61F 2002/30123; A61F 2002/3013; A61F 2002/30138; A61F 2002/30197; A61F 2002/30215; A61F 2002/30166; A61F 2002/30227; A61F 2002/30878; A61F 2002/30883; A61F 2002/30884; A61F 2002/30995; A61B 17/0642

See application file for complete search history.

(56) References Cited

U.S. PATENT DOCUMENTS

| | | | | |
|---|---|---|---|---|
| 5,609,636 A | * | 3/1997 | Kohrs | A61F 2/4455 606/279 |
| 5,669,909 A | * | 9/1997 | Zdeblick | A61F 2/4455 606/247 |
| 5,683,394 A | * | 11/1997 | Rinner | A61F 2/4455 606/279 |
| 5,779,707 A | * | 7/1998 | Bertholet | A61B 17/8625 606/301 |

(Continued)

FOREIGN PATENT DOCUMENTS

WO    WO-2010045749 A1 *  4/2010 ......... A61B 17/1617

*Primary Examiner* — Lynnsy M Summitt
(74) *Attorney, Agent, or Firm* — Francis Law Group

(57) ABSTRACT

Prostheses and methods are described for stabilizing dysfunctional sacroiliac (SI) joints. The prostheses are sized and configured to be press-fit into surgically created pilot SI joint openings in dysfunctional SI joint structures. The prostheses have a pontoon shape with opposed elongated partially cylindrical sections connected by a bridge section. The bridge section can have various shapes, such as an offset, arched structure, to accommodate the delivery and/or positioning of a primary or supplemental support member or device between the first and second elongated sections, such as a sacral-alar iliac (S2AI) screw or surgical dowel member.

7 Claims, 46 Drawing Sheets

Related U.S. Application Data application No. 17/463,831, filed on Sep. 1, 2021, which is a continuation-in-part of application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.
| | | |
|---|---|---|
| *A61B 5/06* | (2006.01) | |
| *A61B 6/00* | (2006.01) | |
| *A61B 6/03* | (2006.01) | |
| *A61B 8/08* | (2006.01) | |
| *A61B 17/16* | (2006.01) | |
| *A61B 17/70* | (2006.01) | |
| *A61B 17/88* | (2006.01) | |
| *A61B 34/20* | (2016.01) | |
| *A61F 2/44* | (2006.01) | |
| *A61F 2/46* | (2006.01) | |

(52) U.S. Cl.
CPC ............. *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); *A61F 2002/30166* (2013.01); *A61F 2002/30593* (2013.01); *A61F 2002/30995* (2013.01)

(56) References Cited

U.S. PATENT DOCUMENTS

| | | | | |
|---|---|---|---|---|
| 5,782,919 A * | 7/1998 | Zdeblick | ............... | A61F 2/4455 606/247 |
| 5,904,719 A * | 5/1999 | Errico | .................... | A61F 2/446 623/17.16 |
| 6,371,987 B1 * | 4/2002 | Weiland | ................ | A61F 2/4455 623/17.11 |
| 6,641,613 B2 * | 11/2003 | Sennett | .............. | A61B 17/1757 623/17.11 |
| 6,666,888 B1 * | 12/2003 | Jackson | ................... | A61F 2/446 623/17.11 |
| 6,743,256 B2 * | 6/2004 | Mason | .................... | A61F 2/447 623/17.11 |
| 7,452,369 B2 * | 11/2008 | Barry | .................... | A61F 2/4405 606/279 |
| 7,837,732 B2 * | 11/2010 | Zucherman | ............. | A61F 2/446 623/17.11 |
| 8,162,981 B2 * | 4/2012 | Vestgaarden | ...... | A61B 17/7064 606/247 |
| 8,617,244 B2 * | 12/2013 | Reichen | ................ | A61F 2/4455 623/17.11 |
| 9,039,768 B2 * | 5/2015 | Voellmicke | ........... | A61F 2/4611 606/86 A |
| 11,006,949 B2 * | 5/2021 | Daniel | ................ | A61B 17/068 |
| 11,752,011 B2 * | 9/2023 | Stuart | .................... | A61B 17/92 623/17.11 |
| 2004/0230305 A1 * | 11/2004 | Gorensek | ............. | A61F 2/446 623/18.11 |
| 2007/0093839 A1 * | 4/2007 | Beckendorf | ........ | A61B 17/0642 606/75 |
| 2007/0299529 A1 * | 12/2007 | Rhodes | ................... | A61F 2/389 623/20.32 |
| 2008/0319443 A1 * | 12/2008 | Focht | .................. | A61B 17/0642 606/75 |
| 2009/0036927 A1 * | 2/2009 | Vestgaarden | ...... | A61B 17/7064 606/247 |
| 2010/0125301 A1 * | 5/2010 | Kinmon | ............. | A61B 17/1775 606/300 |
| 2012/0296428 A1 * | 11/2012 | Donner | ................... | A61B 17/7043 623/17.11 |
| 2016/0192930 A1 * | 7/2016 | Finley | .................... | A61B 17/15 606/75 |

\* cited by examiner

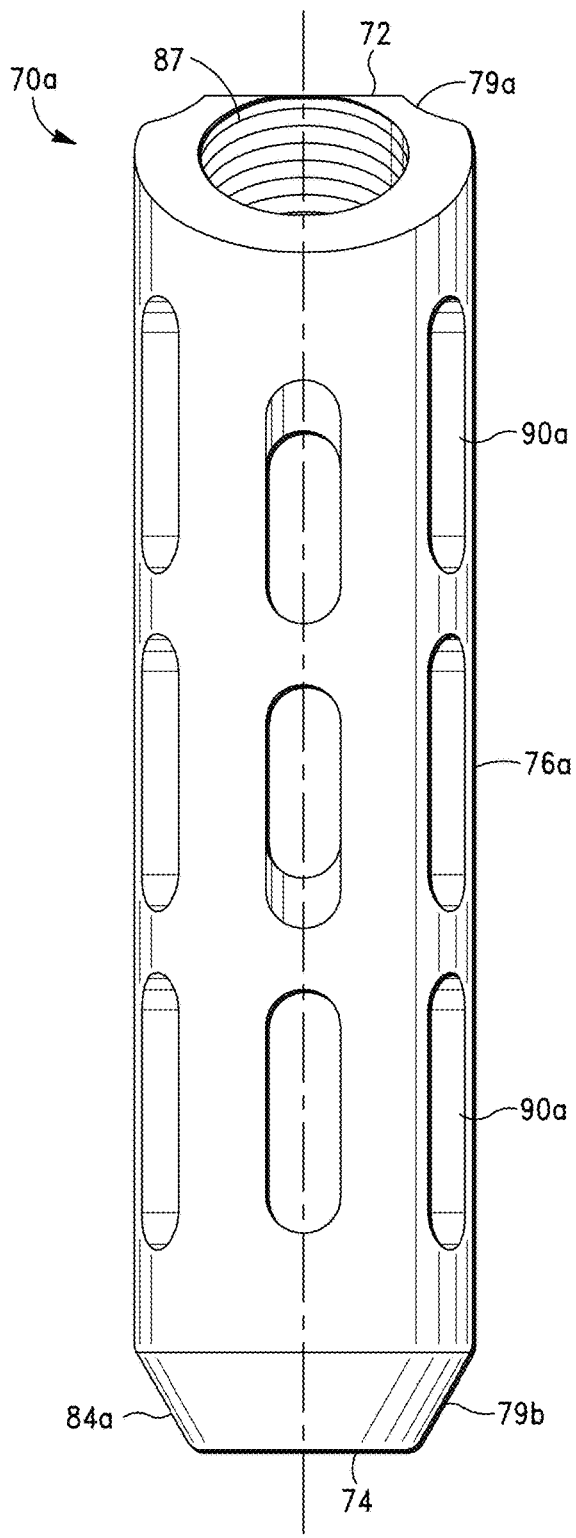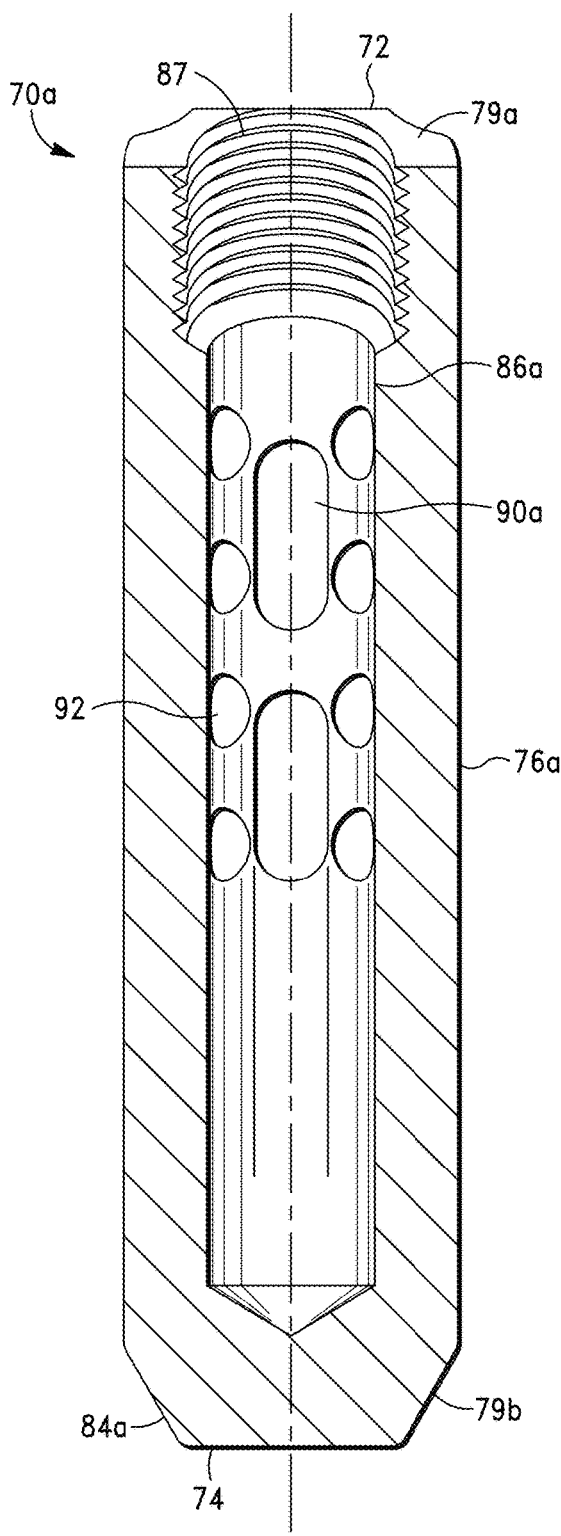
FIG. 6H
FIG. 6I

SYSTEMS, APPARATUS AND METHODS FOR STABILIZING SACROILIAC JOINTS

CROSS-REFERENCES TO RELATED APPLICATIONS

This application is a continuation-in-part of U.S. patent application Ser. No. 17/899,693, filed Aug. 31, 2022, which is a continuation of U.S. patent application Ser. No. 17/463,831, filed Sep. 1, 2021, which is a continuation-in-part application of U.S. patent application Ser. No. 13/857,977, filed Apr. 5, 2013, now U.S. Pat. No. 11,273,042, which is a continuation application of U.S. patent application Ser. No. 13/192,289, filed Jul. 27, 2011, now abandoned, which claims the benefit of U.S. Provisional Patent Application No. 61/368,233, filed Jul. 27, 2010.

FIELD OF THE INVENTION

The present invention relates to systems, apparatus and methods for stabilizing junctions between bone structures. More particularly, the present invention relates to systems, apparatus and methods for stabilizing dysfunctional sacroiliac (SI) joints.

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As is also well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIG. 1A) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3.0°, approximately 1.5° in axial rotation and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

In some instances, SI joint dysfunction, and pain associated therewith, is caused by a misaligned or dislodged surgical joint implant, such as a surgical pin or dowel, or screw, e.g., a sacral-alar iliac (S2AI) screw.

Various non-surgical methods, such as administration of pharmacological agents, e.g., the corticosteroid prednisone, and surgical methods and devices, i.e., prostheses, have been developed and employed to treat SI joint dysfunction.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a prosthesis proximate to or in a dysfunctional SI joint and is generally characterized by the direction of access to the dysfunctional SI joint, i.e., anterior, posterior or lateral.

Although several conventional SI joint stabilization surgical methods and associated bone prostheses have effectively ameliorated pain associated with SI joint dysfunction, there remains many disadvantages associated with the conventional methods and associated prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive methods for SI joint stabilization have thus been developed to address the noted disadvantages associated with open surgery methods. Although conventional minimally-invasive SI joint stabilization methods, such as the methods disclosed in U.S. Pub. No. 2009/0076551 to Petersen, have garnered some success in relieving pain associated with SI joint dysfunction and have effectively addressed many of the disadvantages associated with open surgery methods, there similarly remains many disadvantages associated with conventional minimally-invasive SI joint stabilization methods.

A major disadvantage associated with many conventional minimally-invasive SI joint stabilization methods is that such methods are difficult to perform and, hence, often require extensive, system-specific surgical training and experience. Despite the level of surgical training and experience that surgeons possess, when such conventional minimally-invasive SI joint stabilization methods are employed, there is still a substantial incidence of damage to the lumbosacral neurovascular structures proximate to the SI joint.

A further disadvantage associated with many conventional minimally-invasive SI joint stabilization methods and associated apparatus, i.e., prostheses, such as the methods and prostheses disclosed in U.S. Pub. No. 2009/0076551 to Petersen, is that pre-existing sacral abnormalities can lead to displacement of the implanted prostheses, which can, and often will result in damage to surrounding bone and soft tissue structures and, hence, post-procedure pain.

An additional disadvantage associated with many conventional minimally invasive SI joint stabilization methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a prosthesis in a dysfunctional SI joint.

Further, some conventional minimally-invasive SI joint stabilization methods are particularly prone to failure due to displacement of the prostheses in the dysfunctional SI joint and/or failure of the prostheses to effectively engage the SI joint structures, e.g., articular surfaces of the sacrum and/or ilium.

Various "improved" prostheses have thus been developed for use in minimally-invasive SI joint stabilization methods or procedures to effectively engage SI joint structures and maintain engagement thereto during SI joint function.

Although many of the "improved" prostheses, when deployed properly in a dysfunctional SI joint, can, and often will, effectively engage SI joint structures, there remains several disadvantages associated with the prostheses. Illustrative are the prostheses disclosed in U.S. Pat. No. 8,951,254 to Mayer, et al.

The prostheses disclosed in U.S. Pat. No. 8,951,254 comprise or are coated with a liquefiable synthetic polymer that is adapted to liquify upon administration of mechanical energy, e.g., high frequency vibration, when implanted and re-solidify thereafter to securely engage the SI joint structures, i.e., sacrum and ilium.

A major disadvantage associated with the prostheses disclosed in U.S. Pat. No. 8,951,254 is that the liquefiable synthetic polymers, when re-solidified in situ, are structurally inferior to the osseous or bone tissue of the sacrum and ilium. The fusion sites between the articular surfaces of the sacrum and ilium that define the SI joint are, thus, highly susceptible to structural fatigue and failure, which can, and often will, result in misalignment of the SI joint and ultimately increased pain for the subject.

A further disadvantage associated with the prostheses disclosed in U.S. Pat. No. 8,951,254 is that the synthetic liquefiable synthetic polymers are also substantially immunogenic and will induce an adverse immune response when the prostheses are implanted in a dysfunctional SI joint. As is well established, the adverse immune response can, and often will, prevent healing and osteogenic processes, e.g., remodeling of damaged osseous tissue and regeneration of new osseous tissue.

Additional disadvantages associated with the prostheses disclosed in U.S. Pat. No. 8,951,254 and many other prostheses designed for minimally-invasive SI joint stabilization are that the noted prostheses are difficult to accurately place in optimum positions in a dysfunctional SI joint and, in many instances, lack sufficient structural properties, such as rigidity and/or fatigue resistance, to effectively stabilize the dysfunctional SI joint.

It would thus be desirable to provide SI joint stabilization systems, apparatus and methods, which substantially reduce or eliminate the disadvantages associated with conventional SI joint stabilization systems, apparatus and methods.

It is therefore an object of the invention to provide improved SI joint stabilization systems, apparatus and methods, which substantially reduce or eliminate the disadvantages associated with conventional SI joint stabilization systems, apparatus and methods.

It is another object of the invention to provide improved minimally-invasive SI joint stabilization systems and apparatus, which can be readily employed to place prostheses in and, thereby, stabilize dysfunctional SI joints via a posterior approach.

It is another object of the invention to provide improved minimally-invasive SI joint stabilization systems, apparatus and methods, which can be readily employed to stabilize dysfunctional SI joints.

It is another object of the invention to provide improved minimally-invasive SI joint stabilization systems, apparatus and methods, which can readily be employed in minimally-invasive SI joint stabilization procedures to stabilize SI joint structures with misplaced or dislodged prior implants; particularly, surgical pins, dowels or screws.

It is another object of the invention to provide improved minimally-invasive SI joint stabilization systems, apparatus and methods, which can readily be employed in minimally-invasive SI joint stabilization procedures and provide supplemental stabilization of SI joint structures with prior implants, such as a surgical pin or screw.

It is another object of the invention to provide improved minimally-invasive SI joint stabilization systems, apparatus and methods, which can readily be employed in conjunction with surgical or orthopedic pins, dowels and screws to provide enhanced stabilization of SI joint structures.

It is another object of the invention to provide improved minimally-invasive SI joint stabilization systems and apparatus, which, when implanted in a dysfunctional SI joint, effectively ameliorate pain associated with the SI joint dysfunction.

It is another object of the invention to provide improved SI joint prostheses that can readily be employed in minimally-invasive SI joint stabilization methods and provide secure engagement to SI joint structures.

It is another object of the invention to provide improved SI joint prostheses that can readily be employed in minimally-invasive SI joint stabilization methods and possess optimal structural properties to effectively stabilize dysfunctional SI joints.

It is yet another object of the invention to provide improved SI joint prostheses that can readily be employed in minimally-invasive SI joint stabilization methods and facilitate remodeling of damaged osseous tissue and regeneration of new osseous tissue and osseous tissue structures.

SUMMARY OF THE INVENTION

The present invention is directed to minimally-invasive systems, apparatus and methods for stabilizing dysfunctional SI joints.

In some embodiments of the invention, there are thus provided apparatus for stabilizing dysfunctional SI joints.

In a preferred embodiment, the apparatus comprises an elongated prosthesis structure adapted to be implanted in a dysfunctional SI joint in a posterior trajectory, whereby the apparatus transfix the SI joint, the elongated prosthesis structure comprising a monolithic structure comprising first and second elongated sections, and a bridge section disposed between and connected to the first and second elongated sections, the first elongated section sized and configured to be advanced into the sacrum bone structure of the dysfunctional SI joint when the apparatus is advanced into the dysfunctional SI joint in a posterior trajectory, the first elongated section comprising a tapered distal end to facilitate the advancement of the first elongated section into the sacrum bone structure, the second elongated section sized and configured to be advanced into the ilium bone structure of the dysfunctional SI joint when the apparatus is advanced into the dysfunctional SI joint in the posterior trajectory, the second elongated section also comprising a tapered distal end to facilitate the advancement of the second elongated section into the ilium bone structure, the bridge section adapted to be advanced into the intraarticular region of the dysfunctional SI joint when the apparatus is advanced into the dysfunctional SI joint in the posterior trajectory, whereby the bridge section traverses the sacrum bone structure, intraarticular region and ilium bone structure of the dysfunctional SI joint, the bridge section comprising a tapered distal end to facilitate the advancement of the bridge section into the dysfunctional SI joint.

In a preferred embodiment, the bridge section comprises a structure that is sized and configured to accommodate the delivery and/or positioning of a supplemental joint support member or device, such as a surgical pin, dowel and/or screw, e.g., a sacral-alar iliac (S2AI) screw, between the first and second elongated sections.

In some embodiments, the bridge section comprises an offset, arched shaped structure.

In some embodiments, the bridge section comprises an offset, V-shaped structure.

In some embodiments, the bridge section comprises an offset, U-shaped structure.

In some embodiments, the bridge section comprises a radius-shaped open structure.

In some embodiments, the bridge section comprises a rectangular-shaped open structure.

In some embodiments, the bridge section comprises a V-shaped open structure.

In some embodiments of the invention, there are thus also provided methods for stabilizing dysfunctional SI joints; particularly, dysfunctional SI joints with misaligned or dislodged dowel or screw surgical implants.

In one embodiment, the method comprises the steps of:
a. providing the apparatus described above with an offset, arched-shaped bridge structure;
b. creating a pilot opening in the dysfunctional SI joint proximate the misaligned or dislodged surgical implant, the pilot opening comprising a sacrum portion in the sacrum bone structure and an ilium portion in the ilium bone structure; and
c. advancing the apparatus into the pilot opening in the dysfunctional SI joint in the posterior trajectory, wherein the surgical implant is disposed between the first and second elongated sections of the apparatus and proximate the bridge section.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 6H is a right-side plan view of the prosthesis shown in FIG. 6A, in accordance with the invention;

FIG. 6I is a right-side sectional plan view of the prosthesis shown in FIG. 6A, in accordance with the invention;

DETAILED DESCRIPTION OF THE PREFERRED EMBODIMENT

Figure 1A:
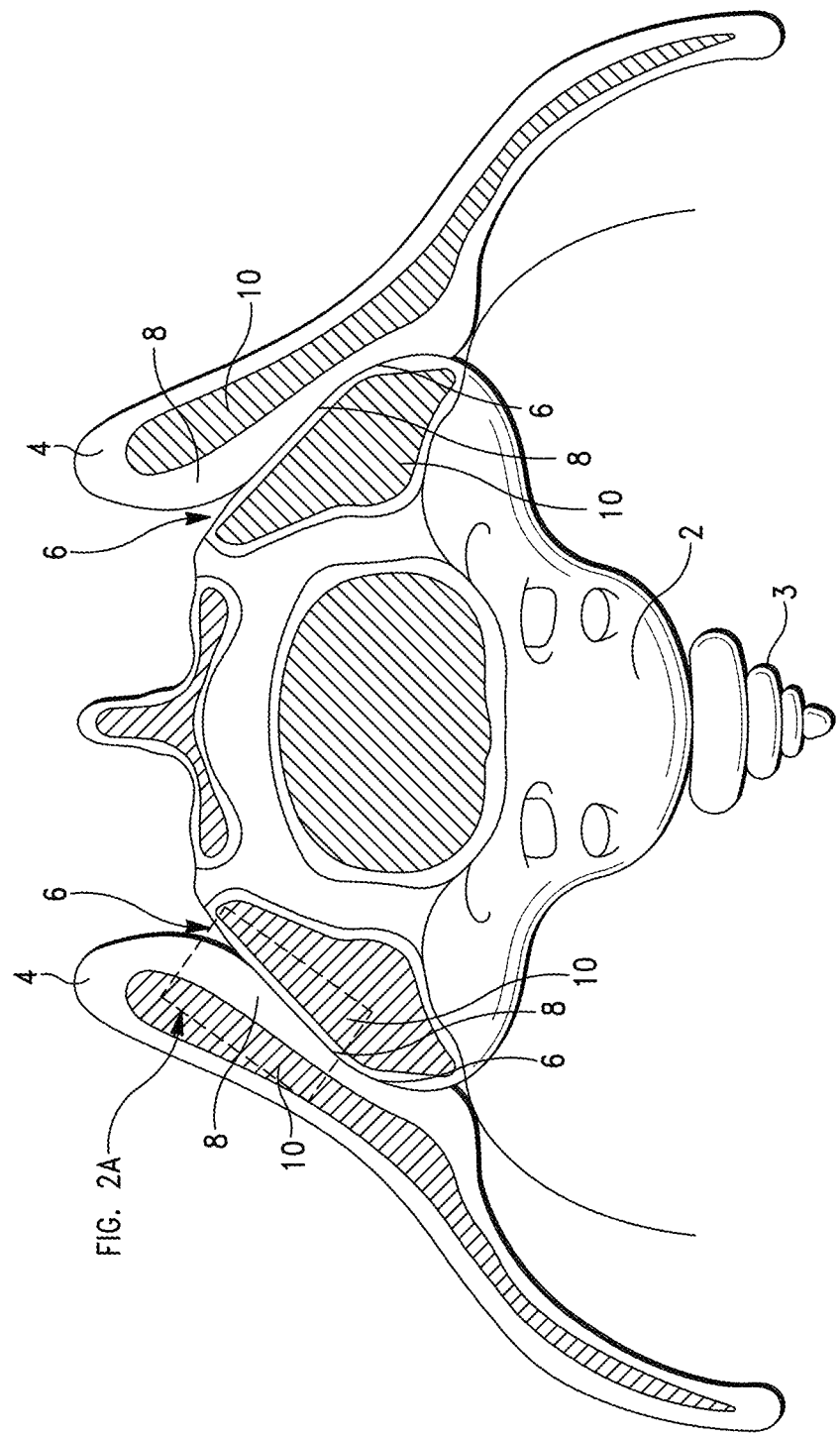
FIG. 1A is a schematic illustration of a human pelvic region from an anteroposterior (AP) perspective showing the SI joints thereof.
Figure 1B:
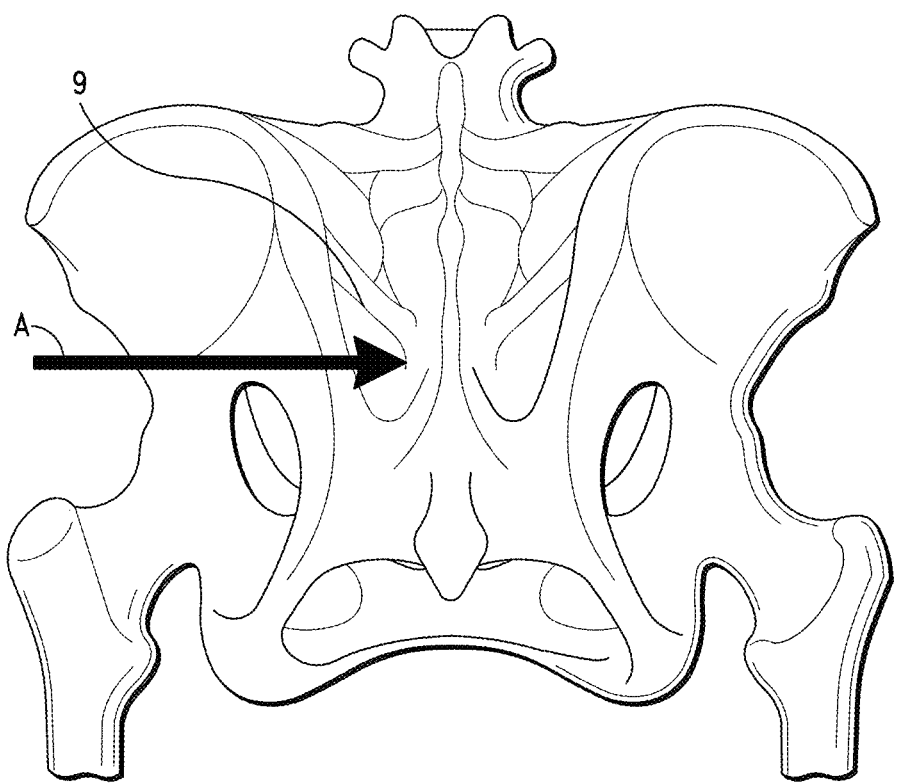
FIG. 1B is another schematic illustration of a human pelvic region from a posterior perspective showing the adjoining sacrum and ilium bone structures, and ligamentous structures thereof.
Figure 1C:
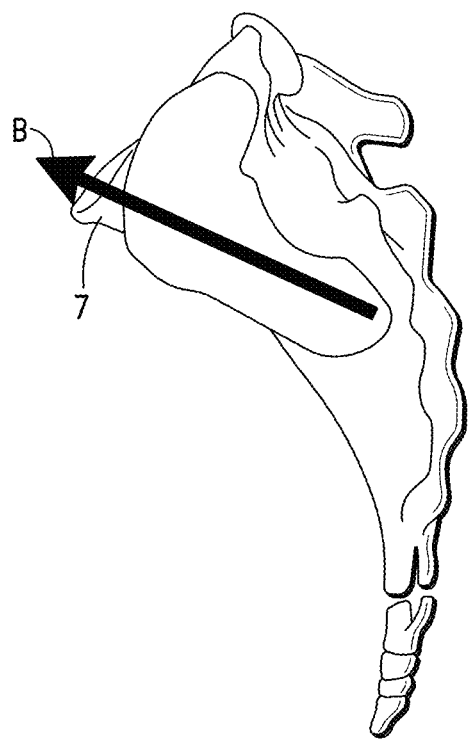
FIG. 1C is a schematic illustration of the sacrum and coccyx from a lateral perspective showing the sacral promontory and the articular surface of sacrum.

Before describing the present invention in detail, it is to be understood that this invention is not limited to particularly exemplified apparatus, systems, structures or methods as such may, of course, vary. Thus, although a number of apparatus, systems, structures and methods similar or equivalent to those described herein can be used in the practice of the present invention, the preferred apparatus, systems, structures and methods are described herein.

It is also to be understood that, although the present invention is described and illustrated in connection with sacroiliac (SI) joint stabilization, fixation and fusion procedures, the invention is not limited to such procedures. According to the invention, the apparatus, systems, structures and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a," "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used in connection with a SI joint, means and includes a physiological abnormality, disorder or impairment of an SI joint, including, but limited to, traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "articular surface" and "articulating surface" are used interchangeably herein in connection with bone structures; particularly, the sacrum and ilium bone structures of a SI joint, and mean and include a surface of a bone structure that forms an articulating junction (i.e., a synovial joint) with an adjacent bone structure, e.g., the articular surfaces of the sacrum and ilium bone structures.

The terms "fusion" and "arthrodesis" are used interchangeably herein in connection with bone structures, and mean and include partial or complete immobilization of adjacent bone structures; particularly, the sacrum and ilium bone structures of a SI joint.

The term "stabilization", as used herein, means and includes reinforcing, e.g., supporting, or modulating motion of adjacent articular bone structures; particularly, the sacrum and ilium bone structures of a SI joint. The term "stabilization", thus, in some instances, means and includes fusion and arthrodesis of adjacent bone structures.

The term "transfix", as used herein in connection with a SI joint, means and includes stabilization of the SI joint via advancement of a prosthesis of the invention into the SI joint and/or the position of the prosthesis after being advanced into the SI joint, wherein the prosthesis intersects (i.e., passes through) the axial and sagittal plans of the ilium and sacrum bone structures of the SI joint, whereby the SI joint is rendered motionless along its longitudinal axis.

The term "prosthesis", as used herein in connection with bone structures, means and includes a system or apparatus configured and adapted to stabilize or modulate motion of articulating bone structures; particularly, the sacrum and ilium bone structures of a SI joint.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly (lactic-co-glycolic) acid (PLGA) and poly(ε-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly (polyol sebacate) (PPS), poly(xylitol sebacate) (PXS), poly (xylitol glutamate sebacate) (PXGS), hydroxybutyrate-hydroxyvalerate copolymers, polyesters such as, but not limited to, aspartic acid and different aliphatic diols; poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®), Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone void filler material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly (ethylene glycol) (PGS-PEG); and/or composites thereof, e.g., PGS-hydroxyapatite (HA) composites and PGS-poly (ε-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)) and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2) and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs) and embryonic stem cells.

The terms "biologically active agent" and "biologically active composition" also mean and include an "extracellular vesicle (EV)", "exosome", "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab, disease-modifying anti-rheumatic drugs (DMARDs), including methotrexate and hydroxychloroquine, antibiotics, anti-viral agents, steroidal anti-inflammatoires, non-steroidal anti-inflammatoires, anti-thrombotic agents, including anti-coagulants and anti-platelet agents, and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®) and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, crythromycin, fluoroquinolones, macrolides, azolides, metronidazole, trimethoprim-sulfamethoxazole, polymyxin B, oxytetracycline, tobramycin, cefazolin and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, mean that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to minimally-invasive methods, systems and apparatus for stabilizing dysfunctional SI joints.

In some embodiments of the invention, there are thus provided minimally-invasive systems for stabilizing dysfunctional SI joints. As indicated above, in a preferred embodiment, the minimally-invasive systems (also referred to herein as "minimally-invasive SI joint stabilization systems") can be readily employed in minimally-invasive methods or procedures to stabilize dysfunctional SI joints via a posterior approach.

In some embodiments of the invention, there are also provided apparatus, i.e., SI joint prostheses, that can be readily employed in minimally-invasive procedures to stabilize dysfunctional SI joints; particularly, dysfunctional SI joints with misaligned or dislodged prior implants, such as surgical pins, dowels and/or screws.

Figure 17:
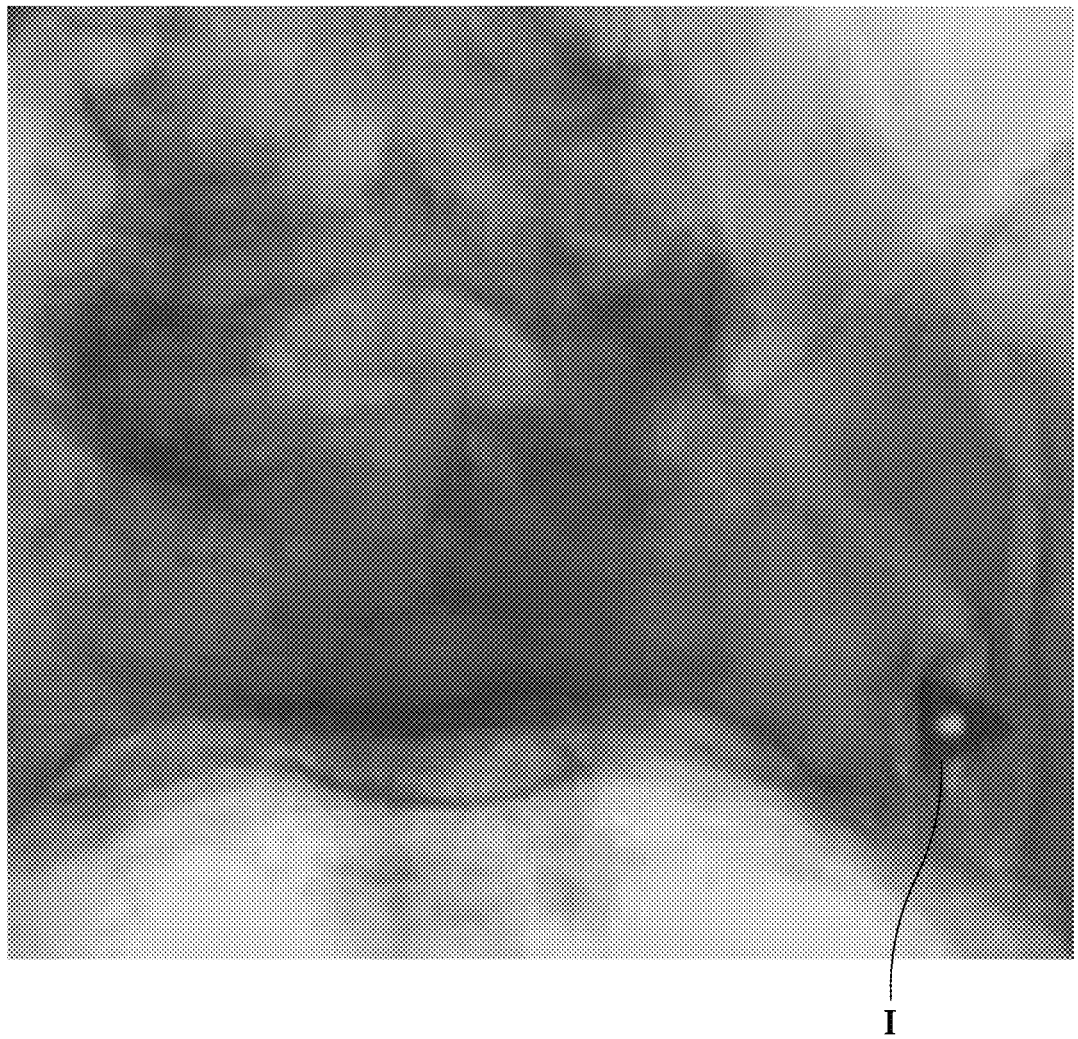
FIG. 17 is a CT scan of a SI joint from a posterior perspective with a surgical dowel implanted therein.

As discussed in detail herein, the apparatus can also be readily employed in minimally-invasive procedures to provide supplemental stabilization of SI joint structures with prior implants, such as a surgical dowel shown in FIG. 17 (and denoted "I").

According to the invention, the apparatus can also be readily employed in conjunction with surgical or orthopedic pins, dowels and screws to provide enhanced stabilization of SI joint structures.

As also discussed in detail herein, the apparatus are specifically configured and adapted to be advanced into SI joints in a posterior trajectory, whereby the apparatus transfix the SI joint.

As indicated above, SI joint stabilization, including minimally-invasive SI joint stabilization, typically comprises surgical placement of a prosthesis proximate to or in a dysfunctional SI joint in anterior, lateral and posterior trajectories.

From the perspective of FIG. 1A, an anterior approach to the SI joint 6 (and, hence, a dysfunctional SI joint) would be substantially perpendicular to the page upon which FIG. 1A is printed.

Figure 2A:
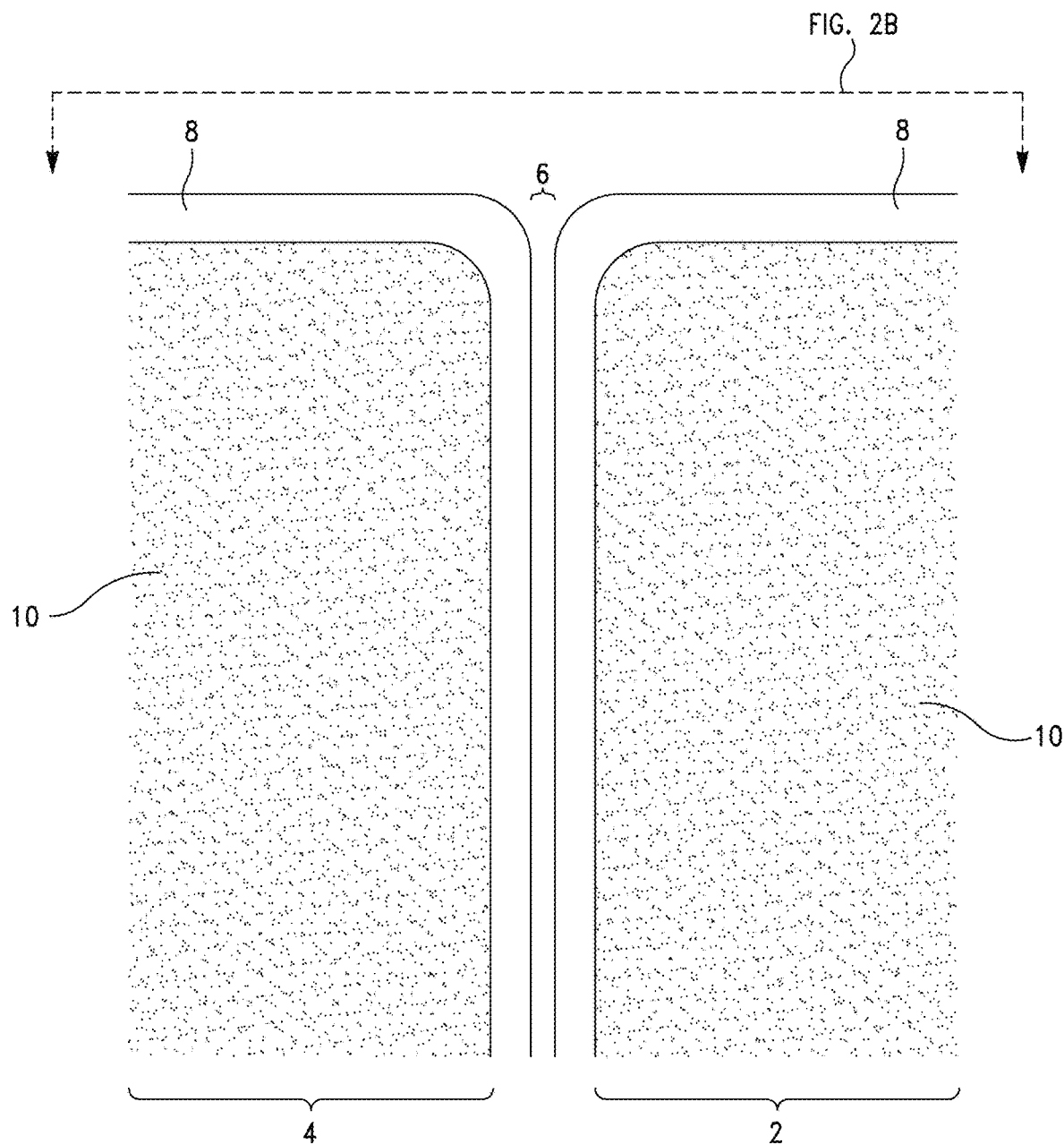
FIG. 2A is an illustration of a SI joint from a superior perspective showing the adjoining sacrum and ilium articular surfaces.

Referring now to FIG. 2A, there is shown a close-up illustration of a portion of the leftmost SI joint 6 illustrated in FIG. 1A. For illustrative simplicity, a uniform layer of cortical bone 8 is shown adjacent to a deeper layer of trabecular bone 10 on both of the depicted sacrum 2 and ilium 4 portions. However, in actuality, such layers are far less uniform and homogeneous.

Figure 2B:
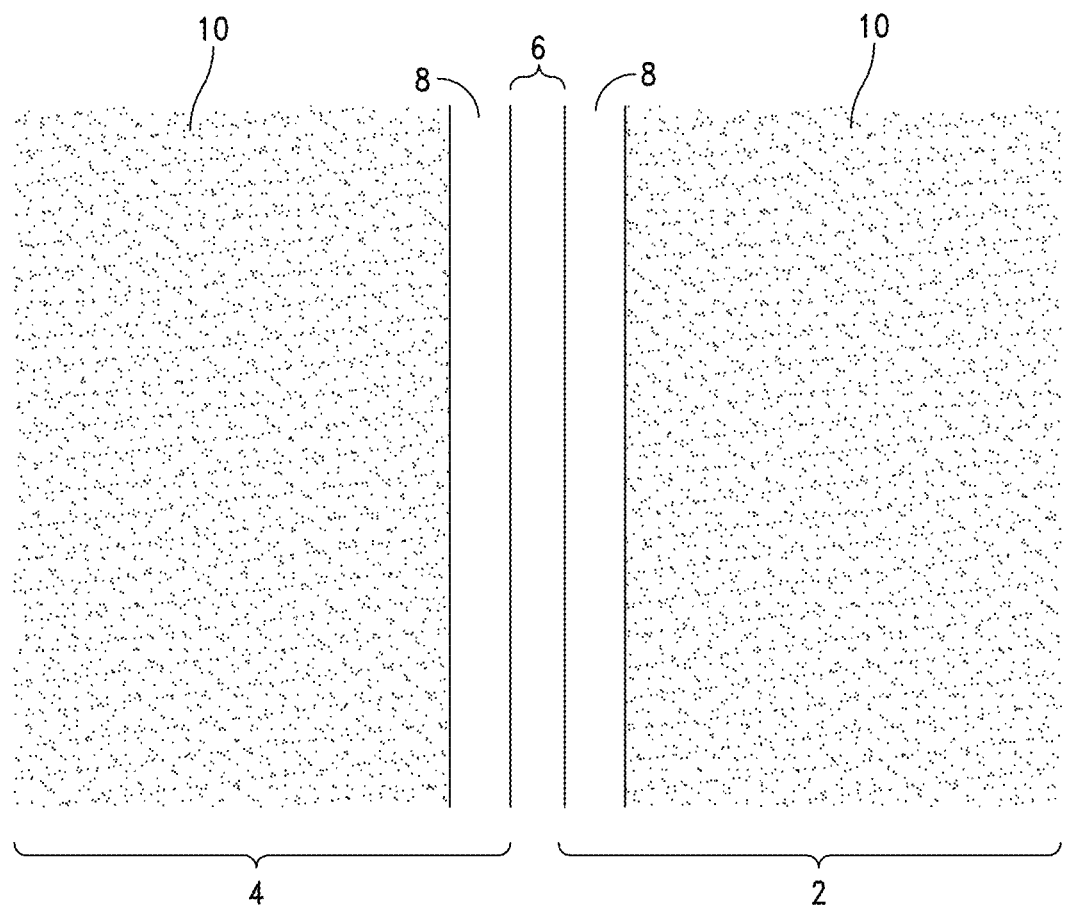
FIG. 2B is another illustration of a SI joint from a posterior perspective showing the adjoining sacrum and ilium articular surfaces.
Figure 2C:
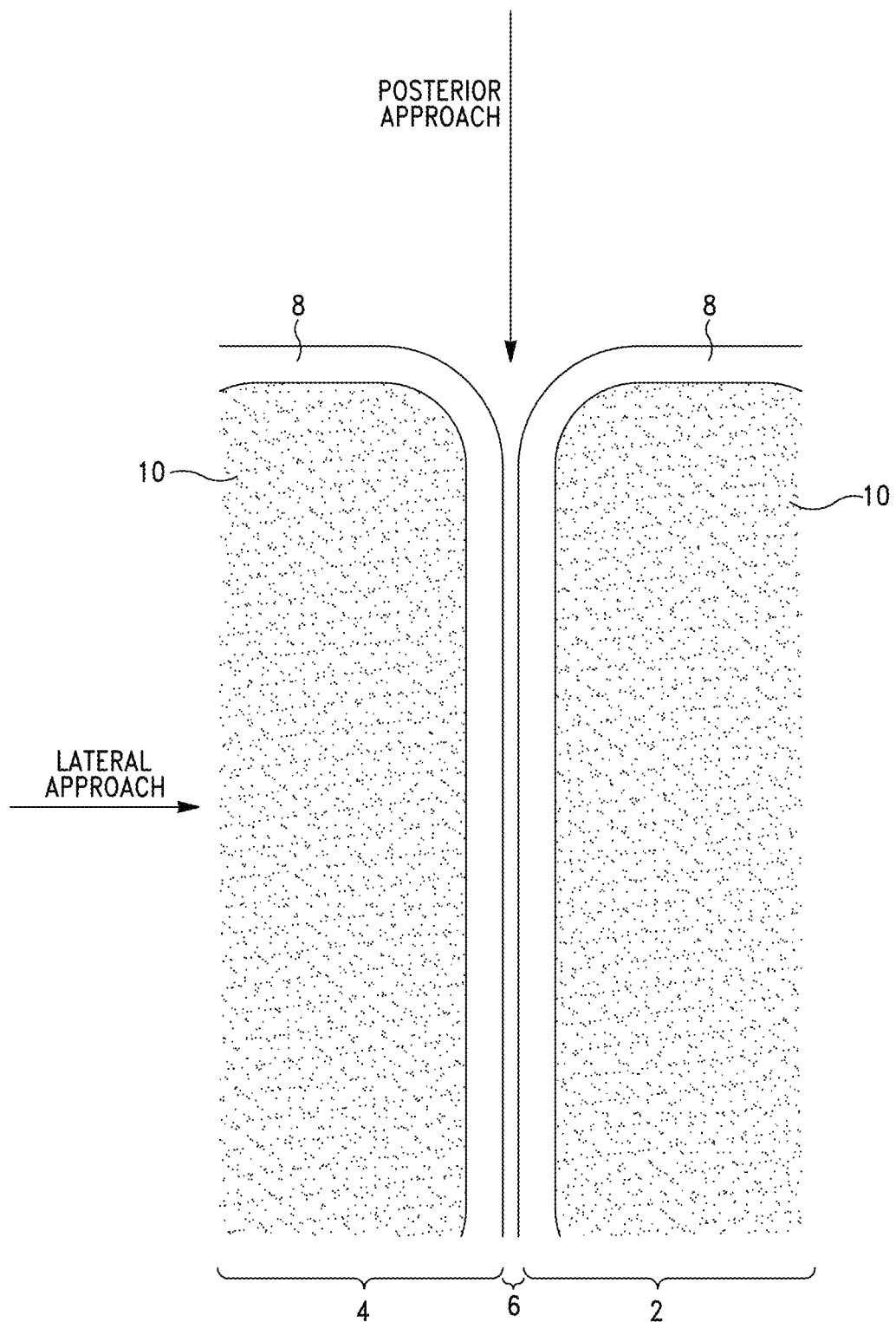
FIG. 2C is a further illustration of the SI joint shown in FIG. 2A showing lateral and posterior approaches to the SI joint, in accordance with the invention.

Referring now to FIG. 2B, there is shown a view of the same structure from a different posterior perspective. From the perspective of FIG. 2B, a posterior approach to the SI joint 6 (and, hence, a dysfunctional SI joint) would be substantially perpendicular to the page upon which FIG. 2B is printed. Indeed, referring to FIG. 2C, a variation similar to that depicted in FIG. 2A is illustrated, showing an approximate approach vector for a lateral approach to the SI joint 6 versus a posterior approach, using the orientation paradigms introduced in FIGS. 1A and 2A-2C. Such paradigms are used to illustrate various embodiments of the subject invention in various figures that follow FIGS. 1A and 2A-2C.

As indicated above, a major disadvantage associated with many conventional anterior or lateral approaches to a dysfunctional SI joint is that muscles and ligaments are typically disrupted and often damaged. Nerves and blood vessels are also susceptible to damage during such SI joint stabilization methods.

In contrast, a posterior approach to a dysfunctional SI joint is much less invasive. Indeed, less tissue and fewer muscles are disrupted, and nerves and large blood vessels are avoided.

As indicated above, in a preferred embodiment of the invention, the system for stabilizing a dysfunctional SI joint comprises a tool assembly and a prosthesis.

Referring now to FIGS. 3A-3C, 4A-4C and 5A-5B, a preferred tool assembly of the invention will be described in detail. As illustrated in FIGS. 3A-3C and 5A-5B, in a preferred embodiment, the tool assembly comprises an elongated guide probe 20, an SI joint opening or defect creation assembly (referred to hereinafter as "defect creation assembly") 30, and prosthesis deployment assembly 50.

Figure 3A:
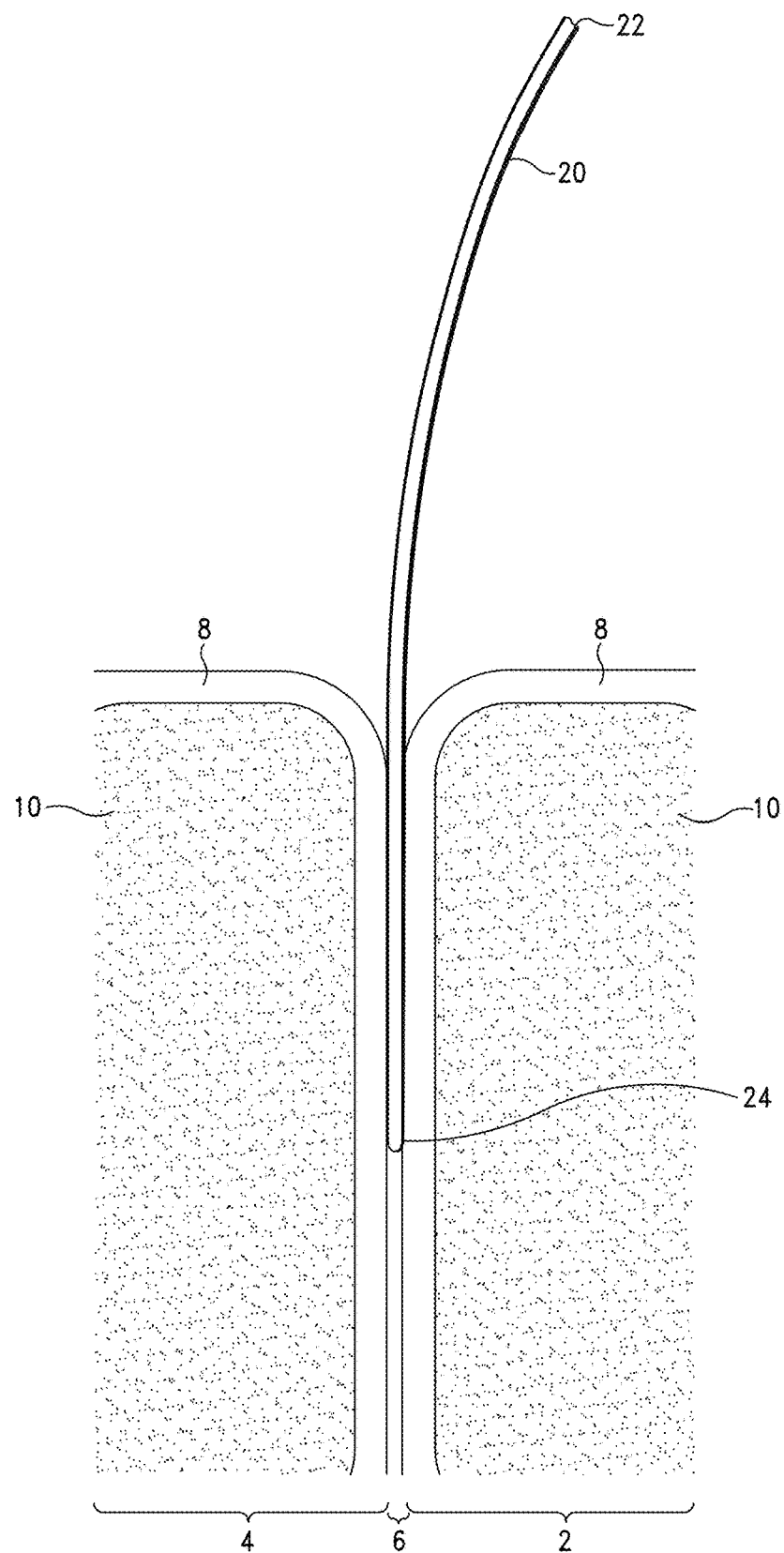
FIG. 3A is a further illustration of the SI joint shown in FIG. 2A showing an elongated guide probe of the invention positioned in the SI joint, in accordance with the invention.
Figure 3B:
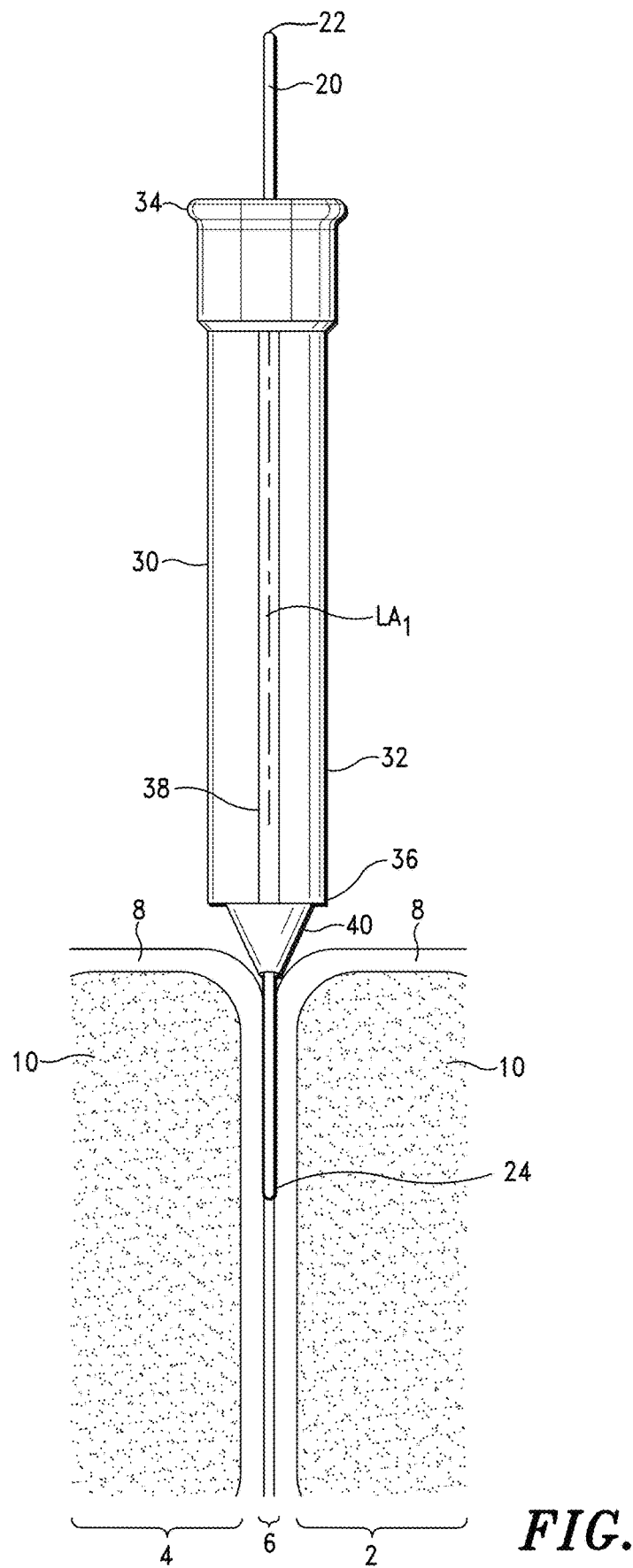
FIG. 3B is a further illustration of the SI joint shown in FIG. 3A showing one embodiment of a defect creation assembly disposed proximate the SI joint, in accordance with the invention.

Referring first to FIGS. 3A and 3B, there is shown a preferred embodiment of an elongated guide probe 20 of the invention. As illustrated in FIGS. 3A and 3B, the elongated guide probe 20 comprises proximal and distal ends 22, 24.

As further illustrated in FIG. 3B, and set forth in Co-pending priority U.S. application Ser. No. 13/857,977, and Co-pending U.S. application Ser. No. 17/463,779 filed on Sep. 1, 2021, which are expressly incorporated by reference herein, the elongated guide probe 20 is sized and configured to be positioned in the dysfunctional SI joint and function as a guide for advancing the defect creation assemblies of the invention; particularly, defect creation assembly 30, into dysfunctional SI joints and placement of a prosthesis therein.

Figure 3C:
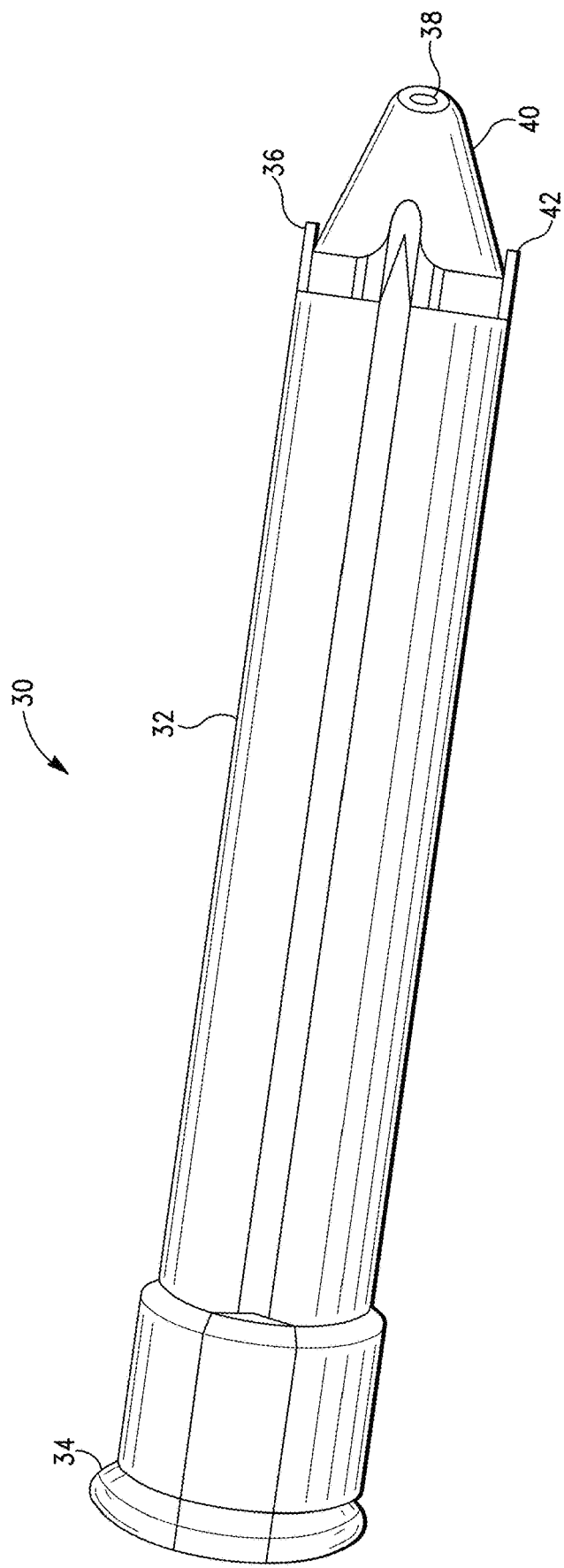
FIG. 3C is a perspective view of the defect creation assembly shown in FIG. 3B, in accordance with the invention.

Referring now to FIGS. 3B and 3C, there is shown a preferred embodiment of the defect creation assembly 30 (referred to as an "osteotome/cannulation assembly" in Co-pending priority U.S. application Ser. No. 13/857,977).

As also set forth in Co-pending U.S. application Ser. Nos. 13/857,977 and 17/463,779, the defect creation assembly 30 is configured and adapted to create pre-determined, surgically produced open spaces or defects in the dysfunctional SI joint (referred to herein after as "pilot SI joint openings") to accommodate placement of a prosthesis of the invention therein.

As illustrated in FIGS. 3B and 3C, the defect creation assembly 30 comprises a housing 32, having a longitudinal axis $LA_1$, a proximal end 34, a distal end 36, and a guide member lumen 38 that extends through the defect creation assembly 30.

As further illustrated in FIG. 3B, the guide member lumen 38 adapted to receive the guide probe 20 therein, whereby the defect creation assembly 30 is allowed to slidably translate or be advanced along the guide probe 20 to position the defect creation assembly 30 proximate to a dysfunctional SI joint site.

In a preferred embodiment of the invention, the defect creation assembly 30 further comprises a bone dislodging apparatus or system 40 disposed on the defect creation assembly distal end 36, which is configured and adapted to dislodge portions of osseous tissue, i.e., bone, proximate to and in the dysfunctional SI joint.

As set forth in Co-pending U.S. application Ser. No. 17/463,779, the bone dislodging system 40 can comprise various bone dislodging apparatus, such as a drill assembly and associated drill bit or orthopedic burr, which can be operated manually, pneumatically, or electromechanically. In a preferred embodiment, the bone dislodging system 40 comprises a drill assembly.

As shown in greater detail in FIG. 3C, according to the invention, the distal end 36 of the defect creation assembly 30 may also comprise one or more teeth or apices 42 configured to assist with creation of a pilot SI joint opening in SI joint bone structures, i.e., sacrum or ilium bone structures.

As indicated above, in a preferred embodiment, the defect creation assemblies of the invention (and, particularly, defect creation assembly 30) are configured and adapted to create pilot SI joint openings in SI joint bone structures to accommodate placement of a prosthesis of the invention therein.

It is however, to be understood that defect creation assembly 30 described herein, is but one embodiment of a defect creation assembly that can be employed within the scope of the invention to create pilot SI joint openings in SI joint bone structures. Indeed, as indicated above and discussed in detail below, various conventional apparatus and systems, such as a surgical drill, can also be employed within the scope of the invention to create pilot SI joint openings of the invention in SI joint bone structures.

As also set forth in Co-pending U.S. application Ser. Nos. 13/857,977 and 17/463,779, the defect creation assemblies of the invention, including defect creation assembly 30, are configured and adapted to create pilot SI joint openings in SI joint bone structures of various sizes and configurations. Illustrative are the pilot SI joint openings depicted in FIGS. 11C-11E of Co-pending priority U.S. application Ser. No. 13/857,977.

Figure 4A:
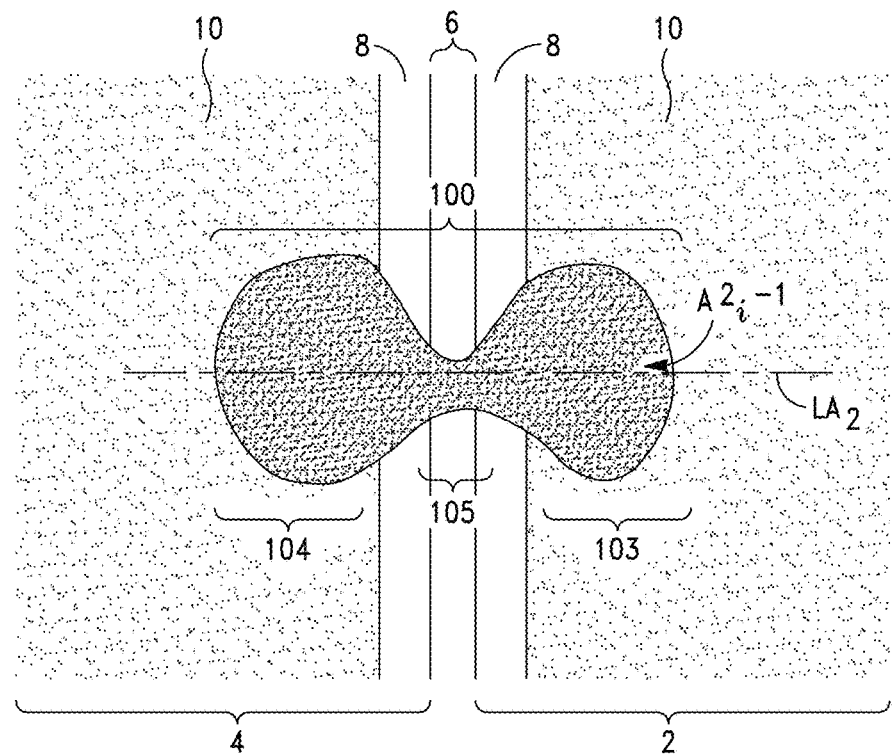
FIG. 4A is a further illustration of the SI joint shown in FIG. 2B showing one embodiment of a pilot SI joint opening, in accordance with the invention.

Referring now to FIG. 4A, there is shown one embodiment of a preferred pilot SI joint opening of the invention (denoted "100") that can be created with the defect creation assemblies of the invention; particularly, defect creation assembly 30.

As illustrated in FIG. 4A, the pilot SI joint opening 100 comprises a three-dimensional opening comprising first and second lobe regions 103, 104; the first lobe region 103 being disposed in the sacrum 2 and comprising a sacrum opening three-dimensional shape, and the second lobe region 104 being disposed in the ilium 4 and comprising an ilium opening three-dimensional shape.

As further illustrated in FIG. 4A, the three-dimensional pilot SI joint opening 100 preferably comprises an SI joint opening cross-sectional shape in a plane that intersects the sacrum 2 and ilium 4 bone structures; the plane being substantially perpendicular to the longitudinal axis $LA_1$ of the defect creation assembly 30 when the defect creation assembly 30 is disposed in a defect creation position in the dysfunctional SI joint. The three-dimensional pilot SI joint opening cross-sectional shape thus comprises the sacrum opening three-dimensional shape and ilium opening three-dimensional shape.

In some embodiments, the three-dimensional pilot SI joint opening 100 is defined in part by at least one noncircular cross-sectional shaped region (denoted "105") in the noted plane.

As additionally illustrated in FIG. 4A, the three-dimensional pilot SI joint opening 100, i.e., cross-sectional shape thereof, also defines a cross-sectional area of the three-dimensional pilot SI joint opening cross-sectional shape (denoted "$A^2_t$-1").

The three-dimensional pilot SI joint opening 100, i.e., cross-sectional shape thereof, also comprises a longitudinal axis (denoted "$LA_2$") in the plane that intersects the sacrum 2 and ilium 4 and an initial pilot SI joint opening length along the axis $LA_2$.

Figure 4B:
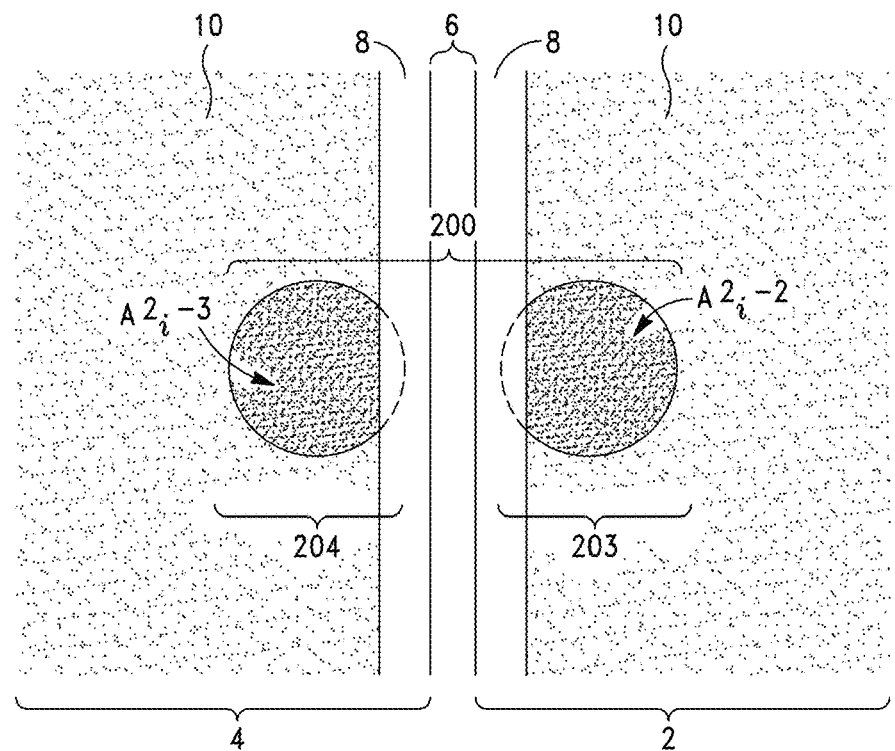
FIGS. 4B and 4C are illustrations of further embodiments of SI joint openings, in accordance with the invention.

Referring now to FIG. 4B, there is shown a further pilot SI joint opening of the invention (denoted "200") that can be created with the defect creation assemblies of the invention; particularly, defect creation assembly 30.

As illustrated in FIG. 4B, the pilot SI joint opening 200 comprises two three-dimensional pilot or guide portions or regions 203, 204; the first guide portion 203 being disposed in the sacrum 2 and the second guide portion 204 being disposed in the ilium 4.

According to the invention, the sacrum and ilium guide portions 203, 204 can comprise various configurations, e.g., cross-sectional shapes, and sizes to, as discussed in detail below, accommodate insertion of defined regions of a prosthesis of the invention therein and transition of the sacrum and ilium guide portions 203, 204 from pilot or first configurations and sizes to expanded second configurations and sizes when the prosthesis is inserted therein.

Figure 4C:
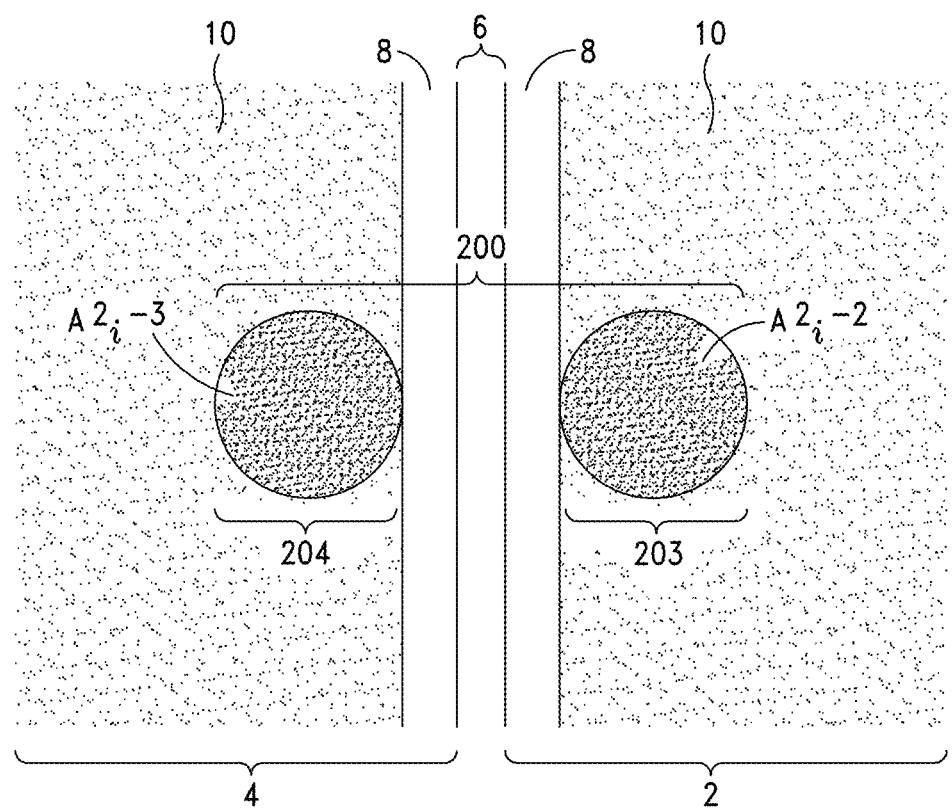

As set forth in Co-pending U.S. application Ser. No. 17/463,779, the sacrum and ilium guide portions 203, 204 can also be disposed at various locations in the sacrum 2 and ilium 4, such as shown in FIGS. 4A, 4B and 4C.

As illustrated in FIG. 4B, in a preferred embodiment, the sacrum and ilium guide portions 203, 204 of the pilot SI joint opening 200 created by the defect creation assembly 30 of the invention comprise substantially circular cross-sectional shapes.

As further illustrated in FIG. 4B, the sacrum and ilium guide portions 203, 204 of the pilot SI joint opening 200, i.e., cross-sectional shape thereof, define cross-sectional areas of the sacrum and ilium guide portions 203, 204 (denoted "$A^2_t$-2" and "$A^2_t$-3", respectively).

In a preferred embodiment, the sacrum and ilium guide portions 203, 204 of the pilot SI joint opening 200 are disposed on a plane that similarly intersects the sacrum 2 and ilium 4.

Figure 5A:
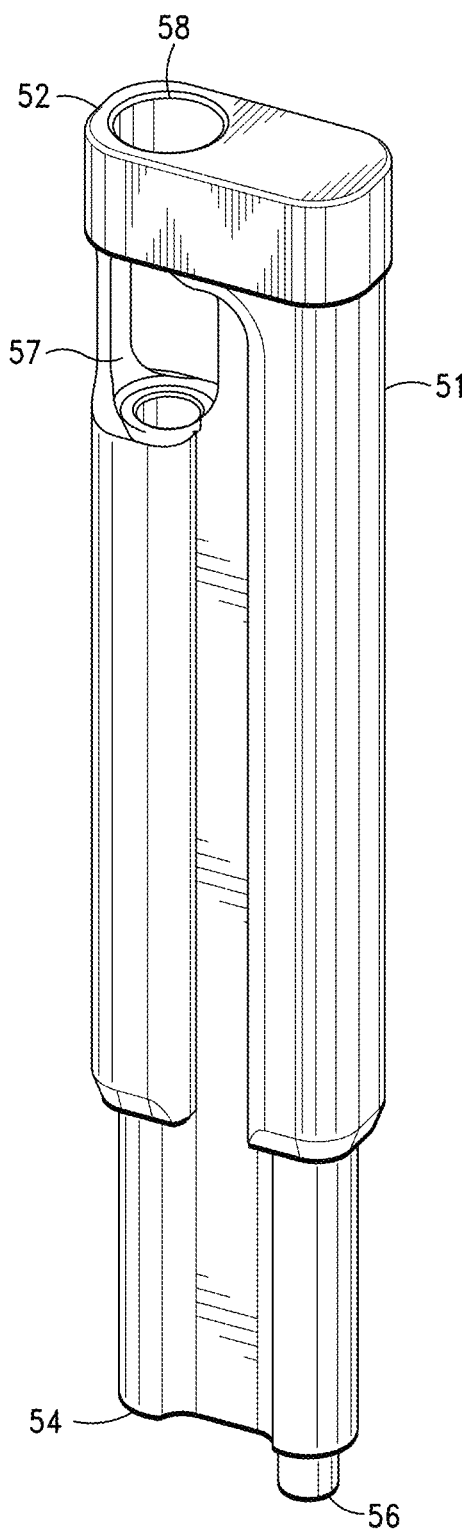
FIG. 5A is a perspective view of one embodiment of a prosthesis deployment assembly, in accordance with the invention.
Figure 5B:
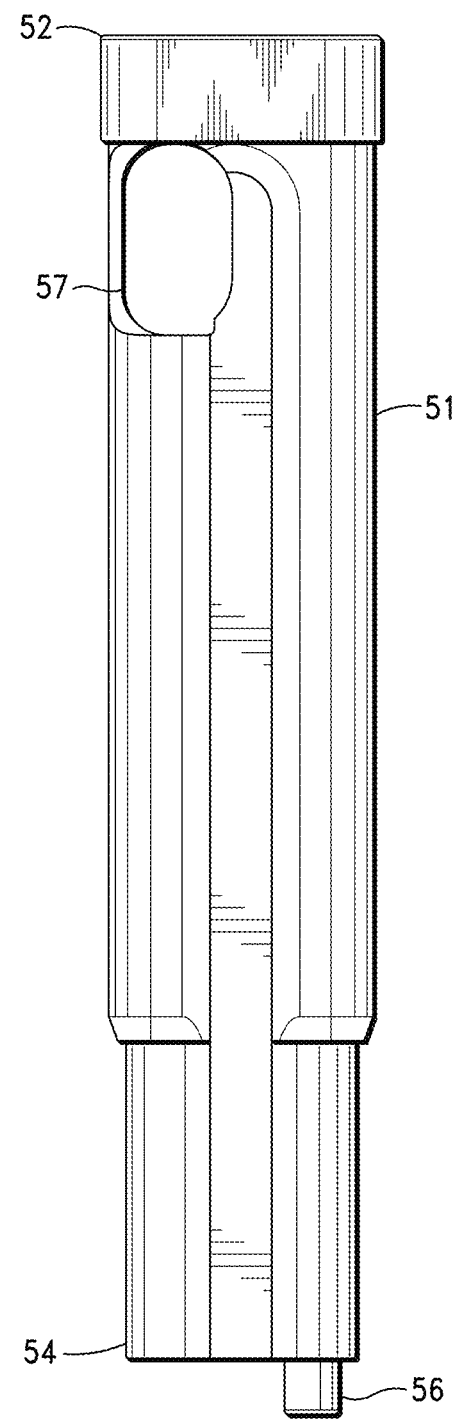
FIG. 5B is a front plan view of the prosthesis deployment assembly shown in FIG. 5A, in accordance with the invention.
Figures 5C, 5D, 5E:
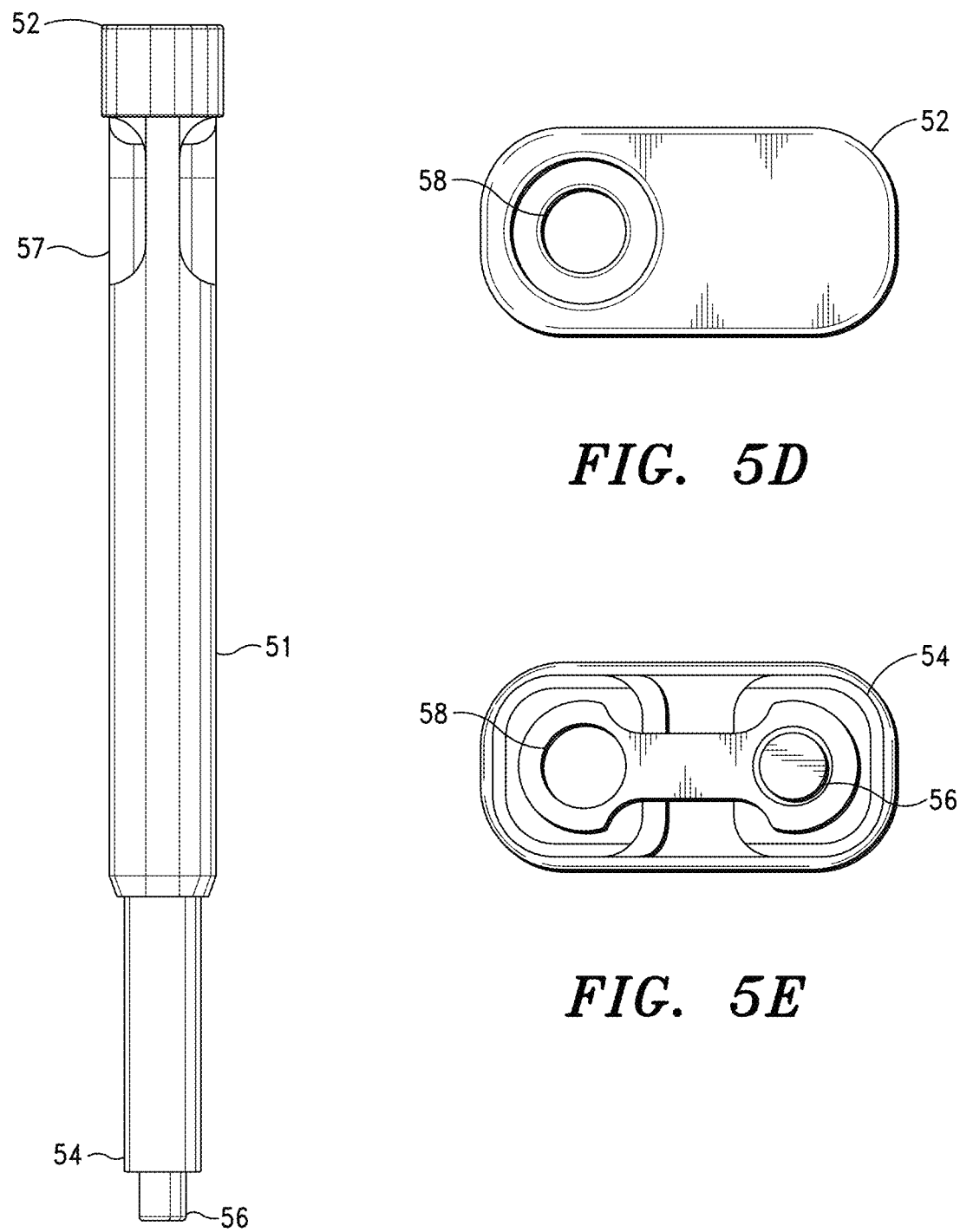
FIG. 5C is a left side plan view of the prosthesis deployment assembly shown in FIG. 5A, in accordance with the invention.
FIG. 5D is a top plan view of the prosthesis deployment assembly shown in FIG. 5A, in accordance with the invention.
FIG. 5E is a bottom plan view of the prosthesis deployment assembly shown in FIG. 5A, in accordance with the invention.
Figure 5F:
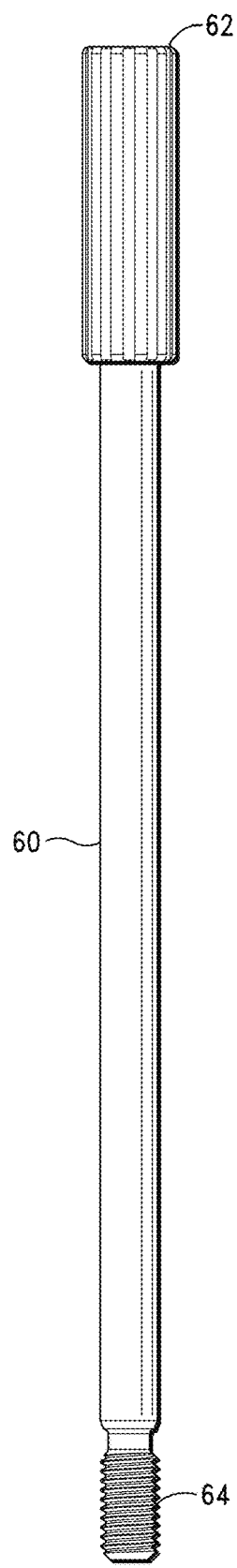
FIG. 5F is a front plan view of a prosthesis engagement rod of the prosthesis deployment assembly shown in FIG. 5A, in accordance with the invention.
Figure 5G:
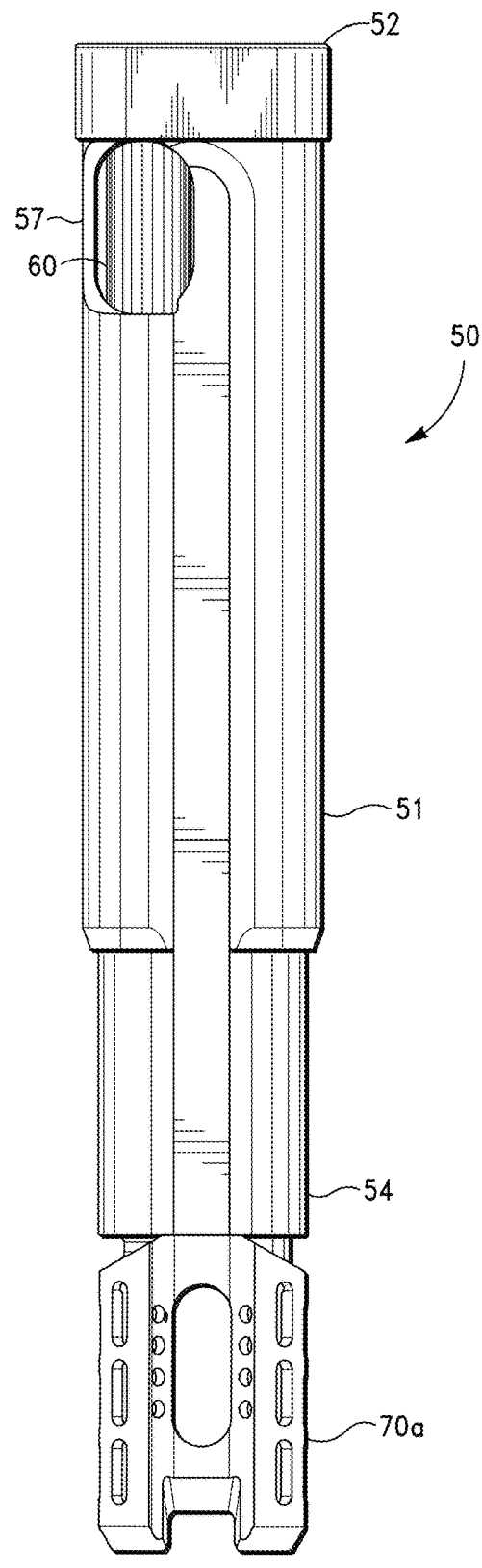
FIG. 5G is a perspective view of the prosthesis deployment assembly shown in FIG. 5A engaged to a prosthesis of the invention, in accordance with the invention.

Referring now to FIGS. 5A-5G, there is shown a preferred embodiment of a prosthesis deployment assembly of the invention (denoted "50" in FIG. 5G).

As also set forth in Co-pending U.S. application Ser. No. 17/463,779, in a preferred embodiment, the prosthesis deployment assembly 50 comprises prosthesis engagement means configured and adapted to connect the prosthesis deployment assembly 50 to prostheses of the invention; particularly, prosthesis 70a, as illustrated in FIG. 5G, and guide the prostheses into pilot SI joint openings created by the defect creation assembly 30.

As illustrated in FIGS. 5A-5C, the prosthesis deployment assembly 50 comprises an elongated guide member 51 comprising proximal and distal ends 52, 54.

As further illustrated in FIGS. 5B and 5E, the elongated guide member 51 further comprises a prosthesis guide pin 56 that extends from the guide member distal end 54. As discussed in detail below and shown in FIG. 5G, the prosthesis guide pin 56 is preferably sized and configured to seat in an internal prosthesis engagement member lumen 86a or 86b of prosthesis 70a.

As illustrated in FIGS. 5A, 5D and 5E, the elongated guide member 51 further comprises an internal lumen 58 that extends from the proximal end 52 of the elongated guide member 51 to the distal end 54 of the elongated guide member 51.

As illustrated in FIG. 5G, in a preferred embodiment of the invention, the internal lumen 58 is sized and configured to receive the prosthesis engagement rod 60 (i.e., prosthesis engagement means) of the prosthesis deployment assembly 50, discussed below.

Referring now to FIG. 5F, there is shown a preferred embodiment of a prosthesis engagement rod 60 of the invention. As illustrated in FIG. 5F, the prosthesis engagement rod 60 comprises a proximal end 62 and a threaded distal end 64, which, as discussed in detail below, is sized and configured to threadably engage an internal prosthesis engagement member lumen of a prosthesis of the invention, e.g., internal prosthesis engagement member lumens 86a and/or 86b of prosthesis 70a.

As further illustrated in FIG. 5F, in a preferred embodiment, the proximal end 62 of the prosthesis engagement rod 60 comprises a knurled configuration to facilitate threading the prosthesis engagement rod 60 into an internal prosthesis engagement member lumen of a prosthesis of the invention.

Referring back to FIGS. 5A and 5B, to further facilitate threading the prosthesis engagement rod 60 into an internal prosthesis engagement member lumen of a prosthesis of the invention, in a preferred embodiment, the elongated guide member 51 further comprises an access port 57 that provides access to the knurled proximal end 62 of the prosthesis engagement rod 60 when positioned in the internal lumen 58 of the elongated guide member 51, as shown in FIG. 5G.

According to the invention, the system for stabilizing dysfunctional SI joints can comprise various prostheses, which are configured and adapted to be inserted into pilot SI joint openings created by a defect creation assembly of the invention.

Suitable prostheses that are configured and adapted to be inserted into a pilot SI joint opening created by a defect creation assembly of the invention are set forth in Co-pending priority application Ser. Nos. 13/857,977 and 17/463,779, which is expressly incorporated by reference herein.

Figure 6A:
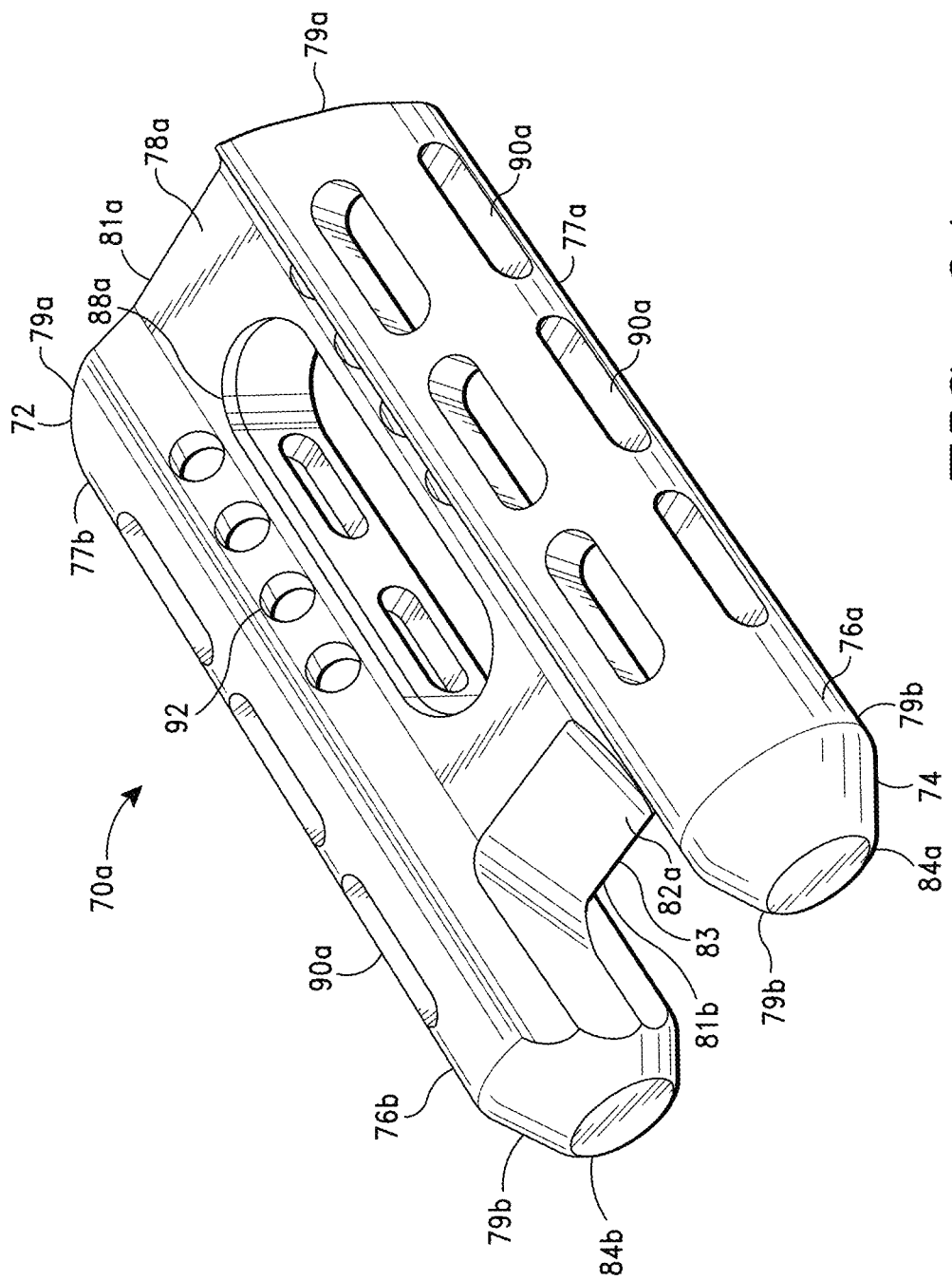
FIG. 6A is a perspective view of one embodiment of a prosthesis, in accordance with the invention.
Figure 6B:
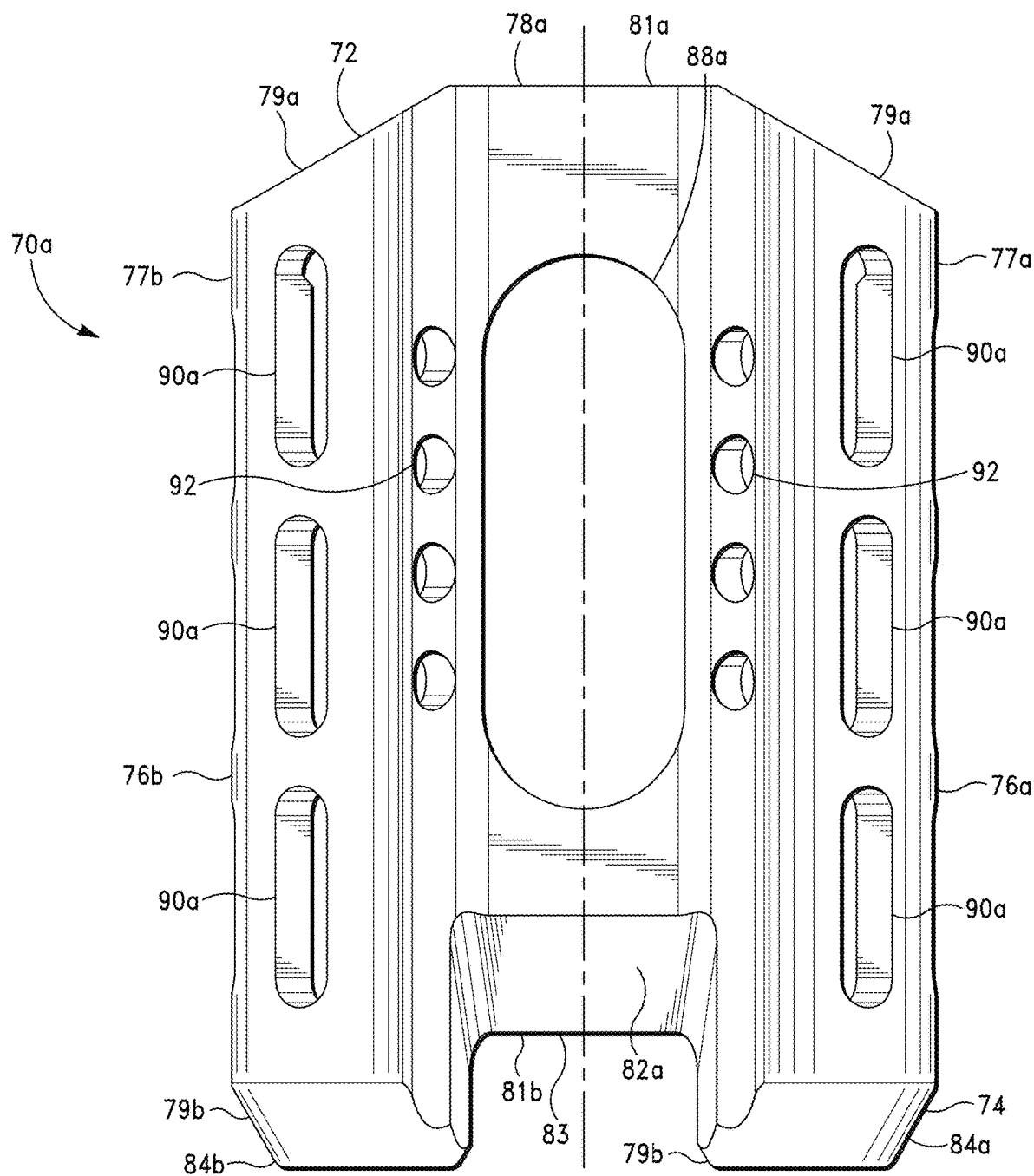
FIG. 6B is a top plan view of the prosthesis shown in FIG. 6A, in accordance with the invention.

According to the invention, suitable prostheses that are particularly suitable for insertion into pilot SI joint openings of the invention; particularly, SI joint openings 100, 200 created by the defect creation assemblies of the invention, include prosthesis 70a, illustrated in FIGS. 6A and 6B, and prostheses 70b, 70c, 70d, 70e, 70f, and 70g illustrated in FIGS. 9A-9C, 10A-10C, 11A-11C, 12A-12C, 13A-13C and 14A-14C.

Referring now to FIGS. 6A and 6B, there is illustrated prosthesis 70a. As illustrated in FIGS. 6A and 6B, the prosthesis 70a comprises an elongated implantable member comprising proximal and distal ends 72, 74, and first and second elongated partially cylindrical sections 76a, 76b connected to a bridge section (also referred to herein as "an osteotome") 78a, whereby the prosthesis 70a comprises a continuous exterior surface comprising first and second partially cylindrical surface regions 77a, 77b.

Figure 6C:
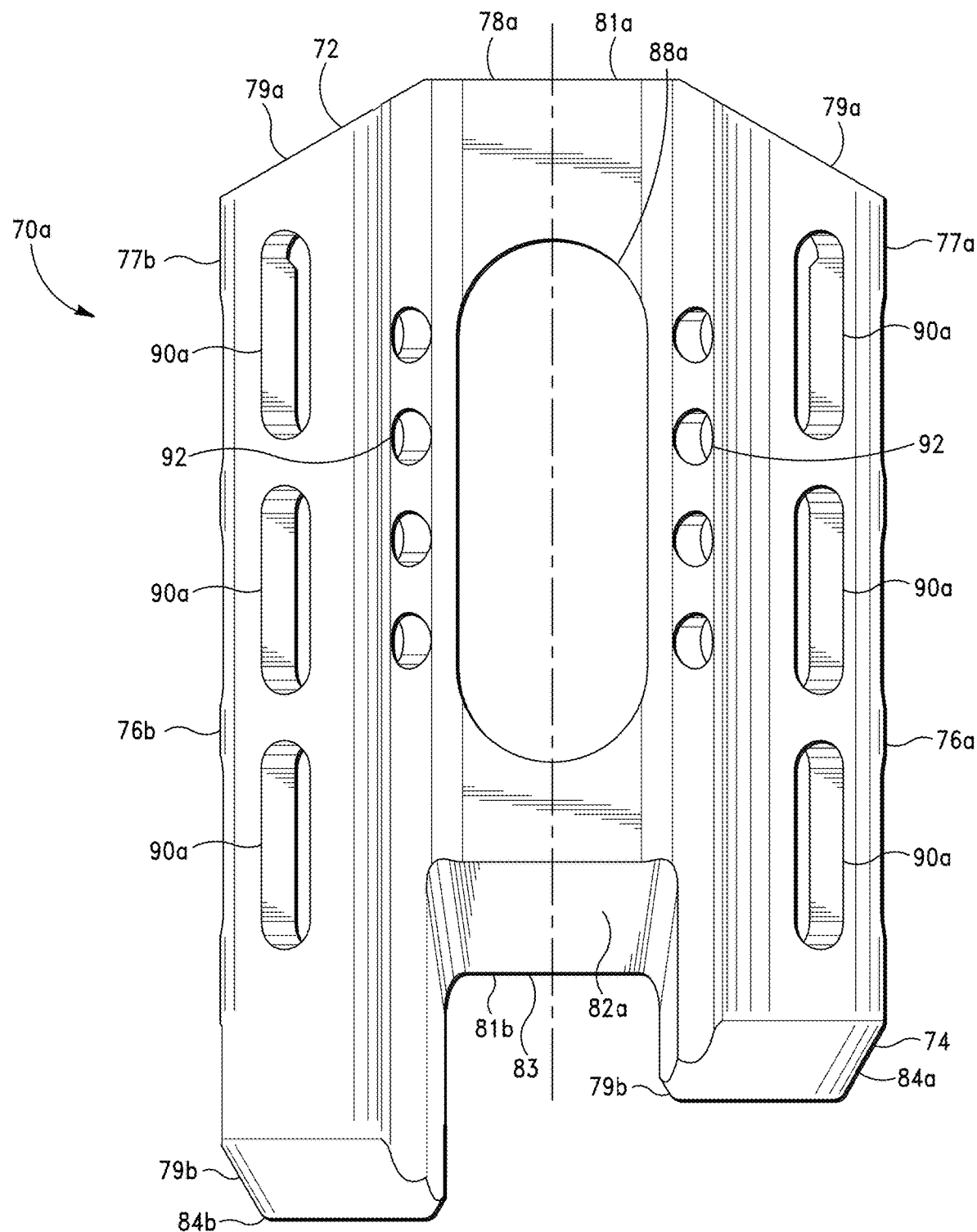
FIG. 6C is another top plan view of the prosthesis shown in FIG. 6A comprising unequal length elongated sections, in accordance with the invention.
Figure 6D:
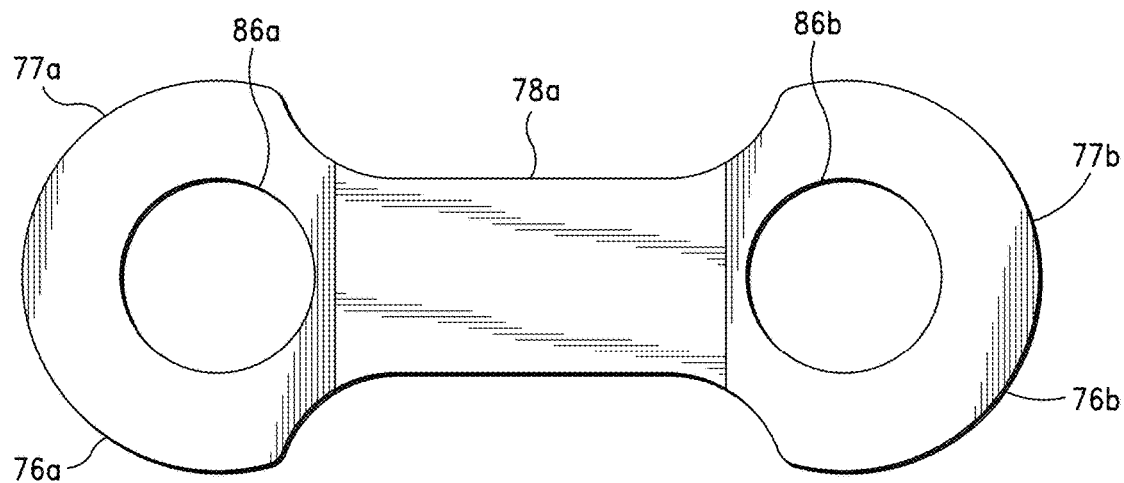
FIG. 6D is a rear plan view of the prosthesis shown in FIG. 6A, in accordance with the invention.
Figure 6E:
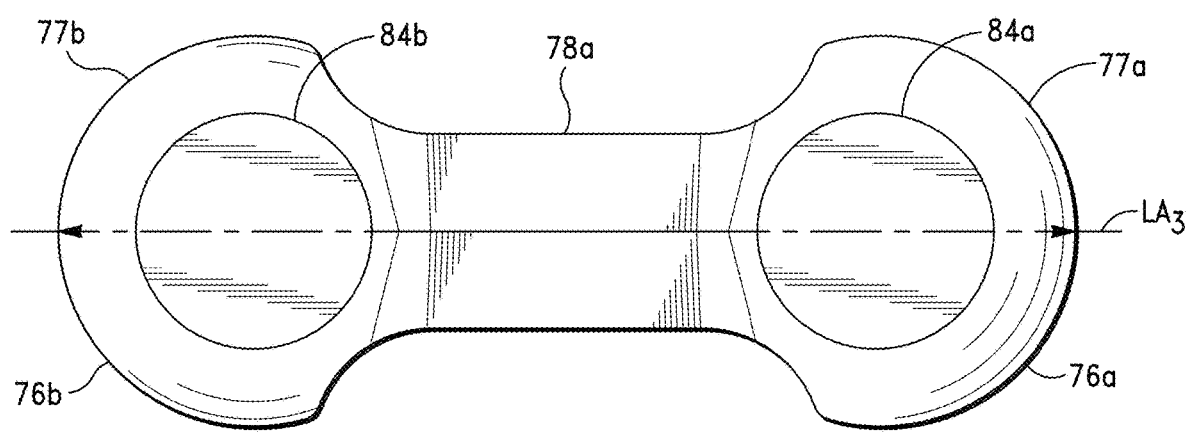
FIG. 6E is a front plan view of the prosthesis shown in FIG. 6A, in accordance with the invention.
Figure 6F:
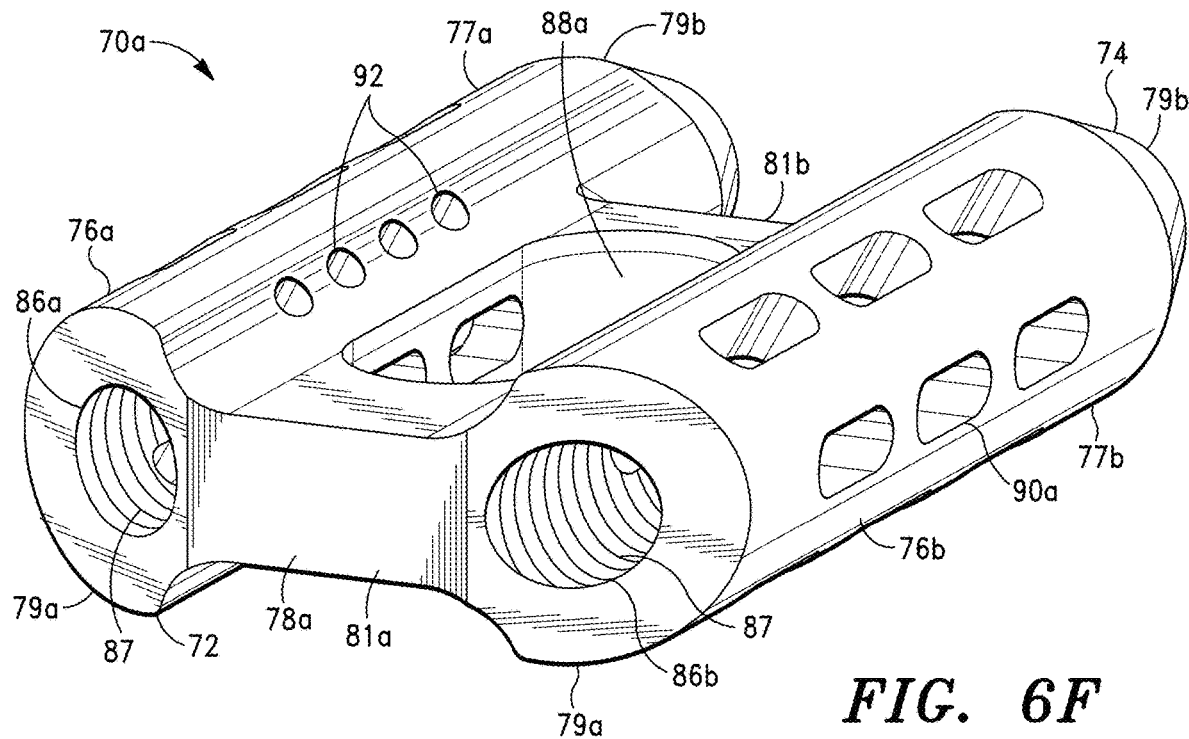
FIG. 6F is a rear perspective view of the prosthesis shown in FIG. 6A, in accordance with the invention.
Figure 6G:
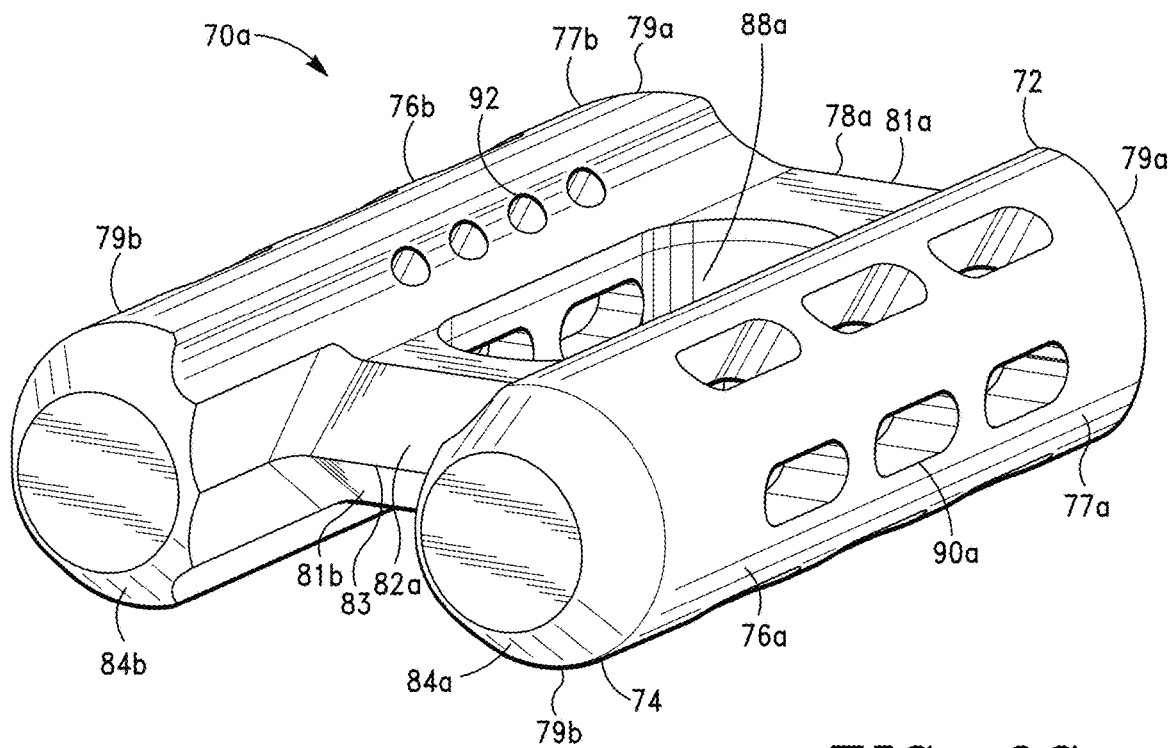
FIG. 6G is a front perspective view of the prosthesis shown in FIG. 6A, in accordance with the invention.

As illustrated in FIGS. 6F and 6G, the first and second elongated partially cylindrical sections 76a, 76b comprise proximal and distal ends 79a, 79b. The bridge section 78a similarly comprises proximal and distal ends 81a, 81b.

According to the invention, the prosthesis 70a can comprise any suitable length from the proximal ends 79a to the distal ends 79b of the elongated partially cylindrical sections 76a, 76b. In some embodiments, the prosthesis 70a comprises a length in the range of 20.0-50.0 mm, more preferably, a length in the range of 30.0-40.0 mm.

According to the invention, the first and second elongated partially cylindrical sections 76a, 76b of the prosthesis 70a can comprise the same length or different lengths, e.g., the second elongated partially cylindrical section 76b comprises a greater length than the first elongated partially cylindrical section 76a, such as illustrated in FIG. 6C.

As illustrated in FIGS. 6D and 6E, the first partially cylindrical surface region 77a preferably comprises a partially cylindrical surface region shape that corresponds to at least a portion of the first lobe region 103 of the pilot SI joint opening 100 and/or the sacrum guide portion 203 of the pilot SI joint opening 200, and/or the second lobe region 104 of the pilot SI joint opening 100 and/or the ilium guide portion 204 of the pilot SI joint opening 200, depending on the entry position of the prosthesis 70a into the pilot SI joint openings 100, 200.

The second partially cylindrical surface region 77b similarly preferably comprises a partially cylindrical surface region shape that corresponds to at least a portion of the first lobe region 103 of the pilot SI joint opening 100 and/or the sacrum guide portion 203 of the pilot SI joint opening 200, or the second lobe region 104 of the pilot SI joint opening 100 and/or the ilium guide portion 204 of the pilot SI joint opening 200, again depending on the entry position of the prosthesis 70a into the pilot SI joint openings 100, 200.

Figure 6J:
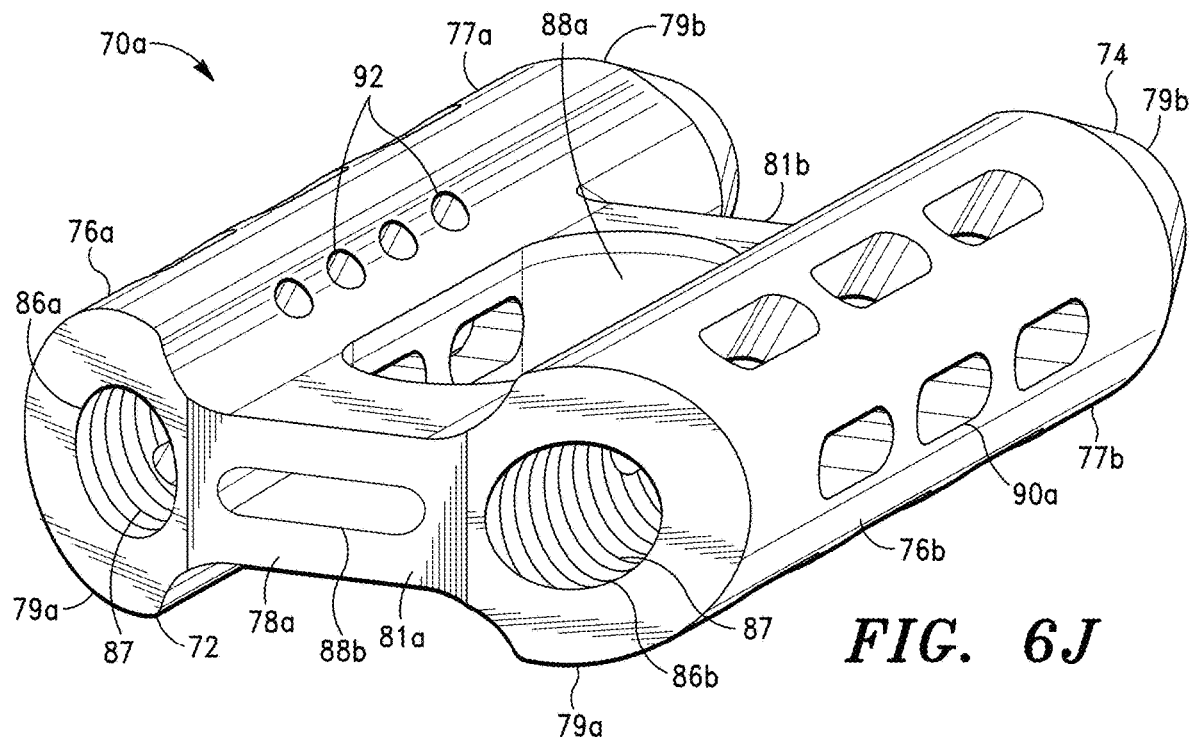
FIG. 6J is another rear perspective view of the prosthesis shown in FIG. 6A comprising a proximal bridge opening, in accordance with the invention.
Figure 6K:
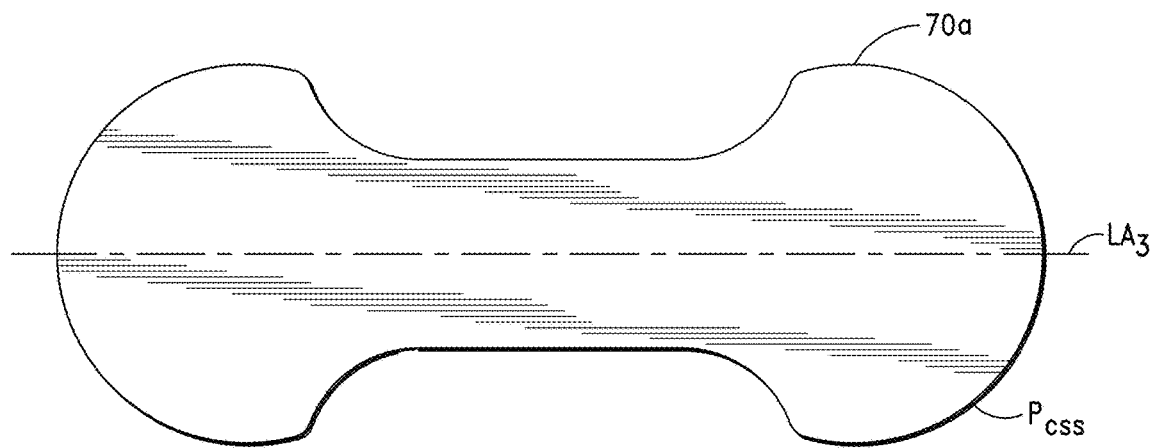
FIG. 6K is another rear plan view of the prosthesis shown in FIG. 6A showing the cross-sectional shape defined by the outer surface of the prosthesis, in accordance with the invention.
Figure 7A:
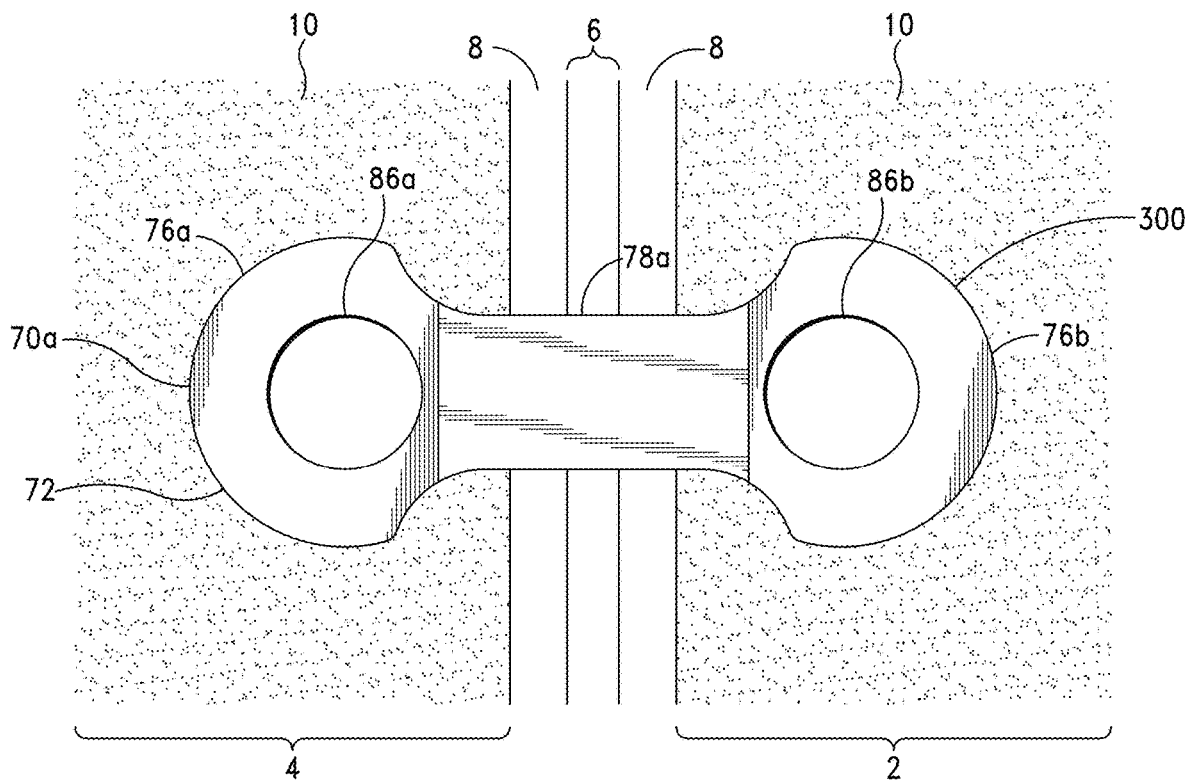
FIG. 7A is an illustration of the prosthesis shown in FIG. 6A inserted into the pilot SI joint opening shown in FIG. 4A and the resulting or induced post-prosthesis insertion SI joint opening, in accordance with the invention.
Figure 7B:
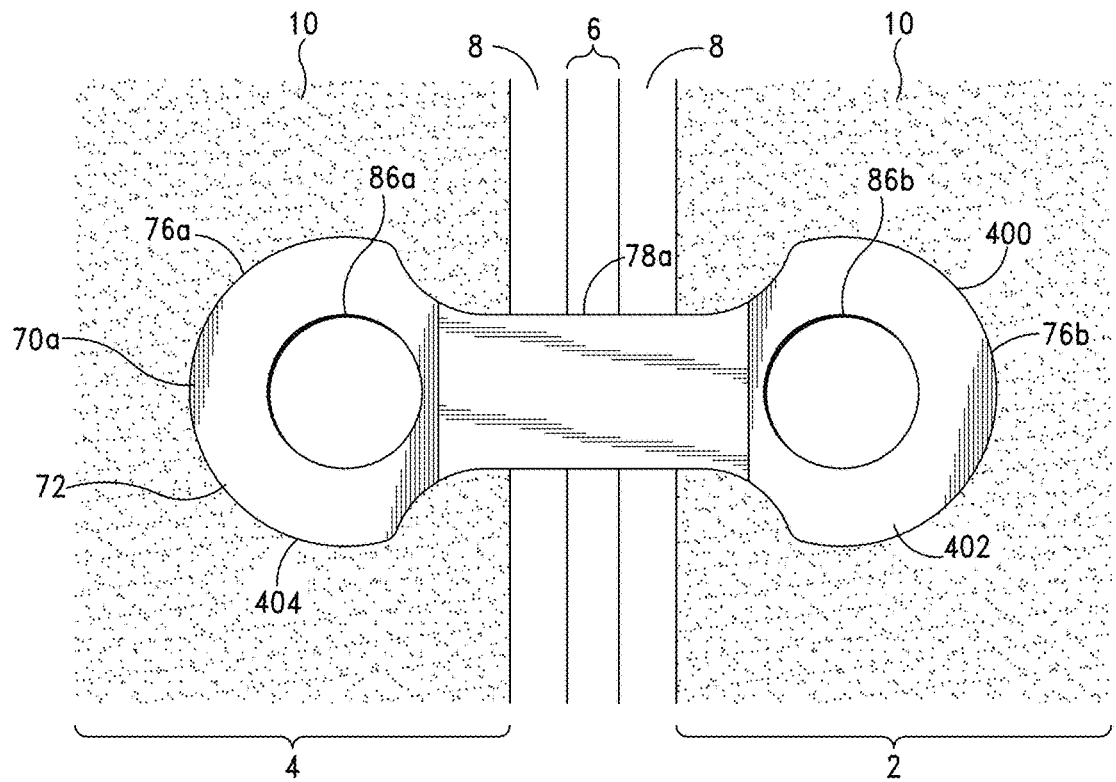
FIG. 7B is an illustration of the prosthesis shown in FIG. 6A inserted in the pilot SI joint opening shown in FIG. 4B and the resulting or induced post-prosthesis insertion SI joint opening, in accordance with the invention.

Referring now to FIG. 6K, according to the invention, the continuous exterior surface of the prosthesis 70a, which is illustrated in FIGS. 6D and 6E, defines a prosthesis cross-sectional shape (denoted "$P_{CSS}$") having a longitudinal axis $LA_3$.

According to one embodiment of the invention, the length of the prosthesis cross-sectional shape Pccs along longitudinal axis $LA_3$ is greater than the length of the pilot SI joint opening 100, i.e., cross-sectional shape thereof illustrated in FIG. 4A, along the longitudinal axis $LA_2$ thereof, whereby, when the prosthesis 70a is inserted into pilot SI joint opening 100, the pilot SI opening 100 transitions to a post-prosthesis insertion SI joint opening 300 comprising a larger cross-sectional length shape that corresponds to the length of the prosthesis cross-sectional shape Pccs.

Figure 8A:
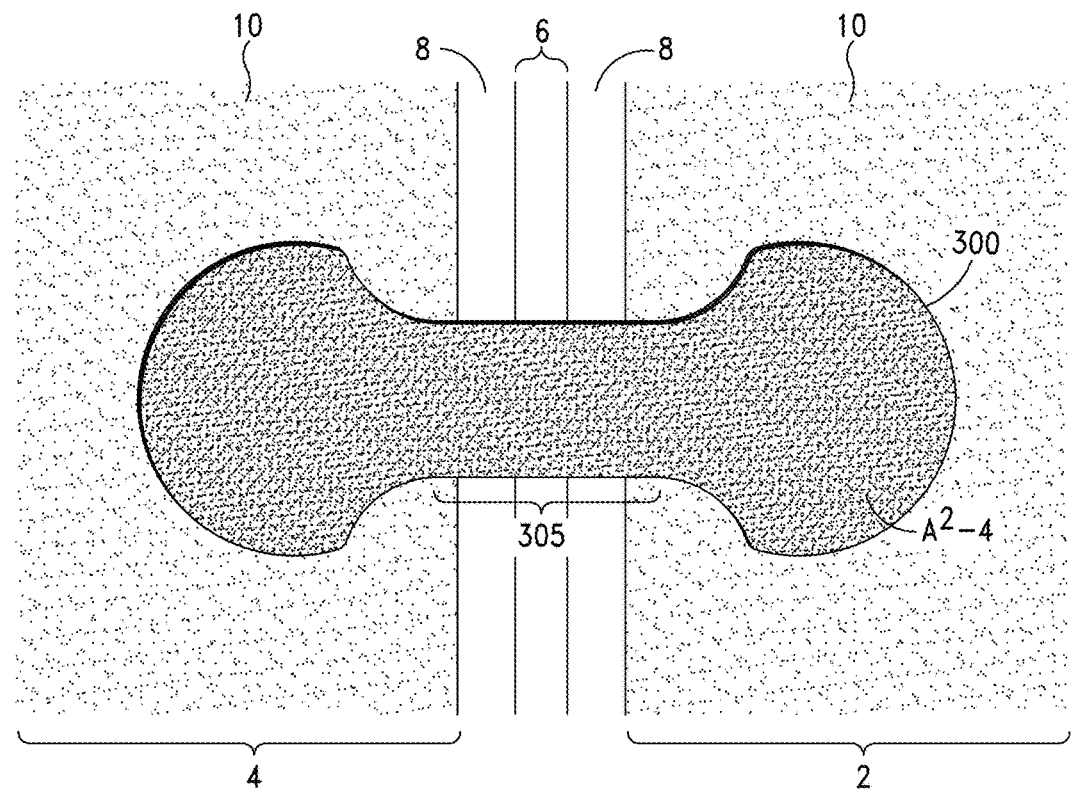
FIG. 8A is an illustration of the post-prosthesis insertion SI joint opening generated or induced when the prosthesis shown in FIG. 6A is inserted in the pilot SI joint opening shown in FIG. 4A, in accordance with the invention.

As illustrated in FIG. 8A, in a preferred embodiment, the cross-sectional area of the opening 300 also comprises a cross-sectional area (denoted "$A^2$-4") that is greater than the cross-sectional area $A^2_i$-1 of the pilot SI joint opening 100.

As further illustrated in FIG. 8A, the noncircular region 105 of pilot SI joint opening 100 also transitions to a much larger noncircular region (denoted "305"), which is achieved by virtue of the tapered distal end of the bridge section, i.e., osteotome, 78a of prosthesis 70a, discussed below, cutting into and through the articular cartilage and cortical bone 8, which define the SI joint 6, and the trabecular bone 10 proximate the SI joint 6.

Figure 8B:
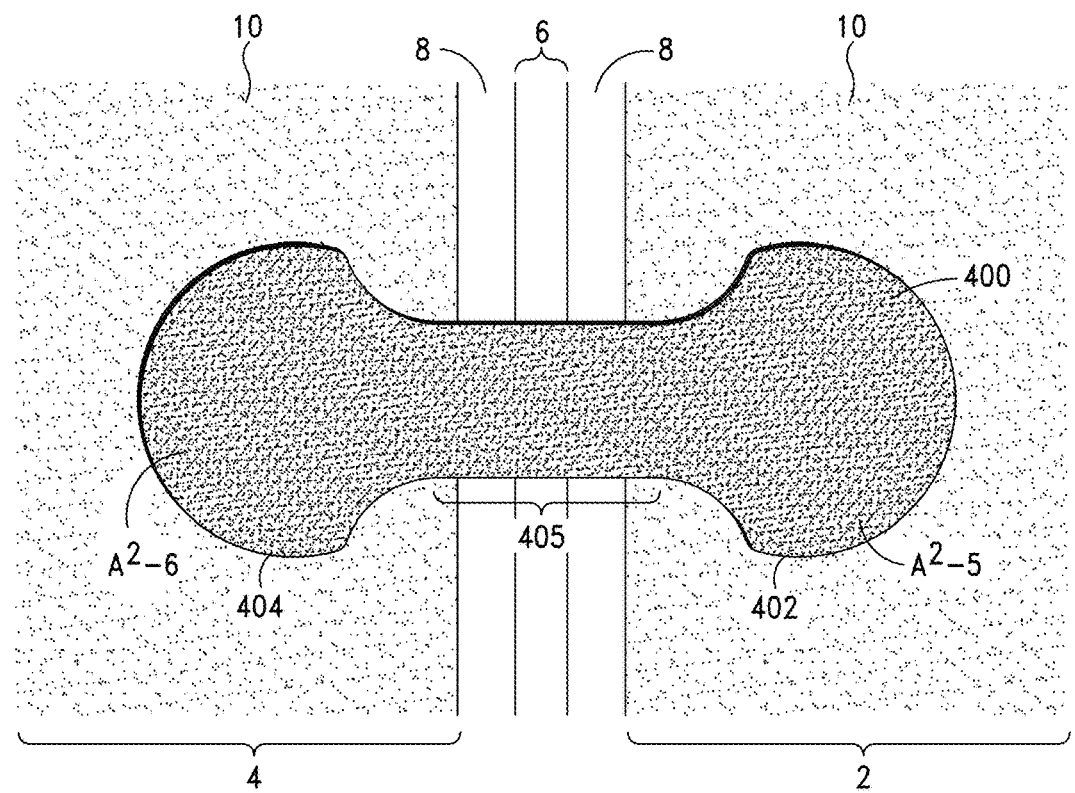
FIG. 8B is an illustration of the post-prosthesis insertion SI joint opening generated or induced when the prosthesis shown in FIG. 6A is inserted in the pilot SI joint opening shown in FIG. 4B and/or 4C, in accordance with the invention.

According to the embodiment of the invention, when the prosthesis 70a is inserted into pilot SI joint opening 200, the pilot SI joint opening 200 similarly transitions to a post-prosthesis insertion SI joint opening 400, wherein, as illustrated in FIG. 8B, the cross-sectional areas of the post-prosthesis sacrum and ilium guide portions of the post-prosthesis insertion SI joint opening 400 (now denoted "402" and "404", respectively) comprise greater cross-sectional areas (denoted "$A^2$-5" and "$A^2$-6").

As further illustrated in FIG. 8B, the post-prosthesis insertion SI joint opening 400 also comprises a noncircular region (denoted "405"), which is similarly achieved by virtue of the tapered bridge or osteotome 78a of the prosthesis 70a cutting into and through the articular cartilage and cortical bone 8, which define the SI joint 6, and the trabecular bone 10 proximate the SI joint 6.

In a preferred embodiment of the invention, to achieve sufficient expansion of the pilot SI joint openings 100, 200 when the prosthesis 70a is inserted therein, preferably, the cross-sectional areas of the regions defined by the first and second elongated partially cylindrical sections 76a, 76b of the prosthesis 70a are at least 0.05% greater than the cross-sectional areas defined by the first and second lobe regions 103, 104 of the pilot SI joint opening 100, and the cross-sectional areas defined by the sacrum and ilium guide portions 203, 204 of pilot SI joint opening 200.

In some embodiments of the invention, the cross-sectional areas of the regions defined by the first and second elongated partially cylindrical sections 76a, 76b of the prosthesis 70a are substantially equal to or slightly smaller, e.g., ≤0.05%, than the cross-sectional areas defined by the first and second lobe regions 103, 104 of the pilot SI joint opening 100, and the cross-sectional areas defined by the sacrum and ilium guide portions 203, 204 of pilot SI joint opening 200.

Referring back to FIG. 6A, in a preferred embodiment, the distal ends 79b of the first and second elongated partially cylindrical sections 76a, 76b comprise tapered regions 84a, 84b, which facilitate (i) insertion of the distal ends 79b of the first and second elongated partially cylindrical sections 76a, 76b into the first and second lobe regions 103, 104 of the pilot SI joint opening 100 and/or the sacrum and ilium guide portions 203, 204 of the pilot SI joint opening 200, and (ii) as discussed above, in some embodiments, transition of the pilot SI joint opening 100 from a first configuration and size (and, hence, cross-sectional area, i.e., $A^2_i$-1 shown in FIG. 4A) to a second expanded configuration and size (and, hence, cross-sectional area, i.e., $A^2$-4 shown in FIG. 8A) when the prosthesis 70a is inserted therein, and transition of the sacrum and ilium guide portions 203, 204 of pilot SI opening 200 from first configurations and sizes (and, hence, cross-sectional areas, i.e., $A^2_i$-2 and $A^2_i$-3 shown in FIG. 4B) to expanded second configurations and sizes (and, hence, cross-sectional areas, i.e., $A^2$-5 and $A^2$-6 shown in FIG. 8B) when the prosthesis 70a is inserted therein.

As illustrated in FIG. 6F, the first elongated partially cylindrical section 76a of the prosthesis 70a comprises an internal prosthesis engagement member lumen 86a that extends from the proximal end 79a of the first elongated partially cylindrical section 76a, and the second elongated partially cylindrical section 76b of the prosthesis 70a also comprises an internal prosthesis engagement member lumen 86b that extends from the proximal end 79a of the second elongated partially cylindrical section 76b.

As indicated above, in a preferred embodiment, the internal prosthesis engagement member lumens 86a, 86b of the prosthesis 70a are sized and configured to receive the prosthesis guide pin 56 of the prosthesis deployment assembly 50 and the prosthesis engagement rod 60 of the prosthesis deployment assembly 50.

As set forth in Co-pending U.S. application Ser. No. 17/463,779 and illustrated in FIGS. 6H and 6I, in a preferred embodiment, the internal prosthesis engagement member lumens 86a, 86b of the first and second elongated partially cylindrical sections 76a, 76b comprise a threaded region 87 proximate the proximal end 79a that is sized and configured to receive and threadably engage the threaded distal end 64 of the prosthesis engagement rod 60 of the prosthesis deployment assembly 50 and the prosthesis extraction rods or screws 602a, 602b of the prosthesis extraction assembly 600.

In a preferred embodiment, the internal prosthesis engagement lumens 86a, 86b are also configured to receive agents and compositions that further facilitate adhesion of the prosthesis 70a to the pilot SI openings 100, 200 of the invention and, thereby, sacrum and/or ilium bone structures, and the aforementioned biologically active agents and compositions, including osteogenic agents and compositions, and pharmacological agents and compositions that facilitate osseous or bone tissue ingrowth into the prosthesis 70a and healing of the SI joint bone structures.

As further illustrated in FIGS. 6A and 6B, in a preferred embodiment, the prosthesis 70a further comprises a plurality of slots 90a and holes 92, which preferably are in communication with the internal prosthesis engagement member lumens 86a, 86b.

In a preferred embodiment, the agents and compositions referenced above are adapted to extrude through the slots 90a (including slots 90a of prostheses 70b, 70c, 70d, 70e, 70f, and 70g, and slots 90b of prosthesis 70g, discussed below) and holes 92 of the prosthesis 70a when the prosthesis 70a (and prostheses 70b, 70c, 70d, 70c, 70f, and 70g) is inserted in a pilot SI joint opening (i.e., pilot SI joint openings 100 or 200), to, as indicated above, (i) further facilitate adhesion of the prosthesis 70a (and prostheses 70b, 70c, 70d, 70c, 70f, and 70g) to the pilot SI openings 100, 200 of the invention and, thereby, sacrum and/or ilium, and (ii) facilitate osseous or bone tissue ingrowth into the prosthesis 70a (and prostheses 70b, 70c, 70d, 70c, 70f, and 70g) and healing of the SI joint bone structures.

Referring now to FIG. 6J, in some embodiments, the bridge section 78a comprises a proximal bridge opening 88b that extends from the bridge section proximal end 81a to and, hence, in communication with the central opening 88a of the bridge section 78a. According to the invention, the proximal bridge opening 88b can comprise any suitable size and/or configuration.

Referring back to FIGS. 6A and 6B, in a preferred embodiment, the distal end 81b of the bridge section or osteotome 78a preferably comprises a taper region 82a, which is configured and adapted to disrupt, i.e., cut into and through, articular cartilage and cortical bone 8 (and, in some aspects, trabecular bone 10), which define a SI joint.

According to the invention, the taper region 82a of the bridge section 78a can comprise various configurations including, without limitation, X-bevel, wedge or bevel-shaped and Y-bevel.

In some embodiments of the invention, the taper region 82a comprises two angled regions that intersect at a central point 83, such as shown in FIGS. 6A and 6F.

Figure 9A:
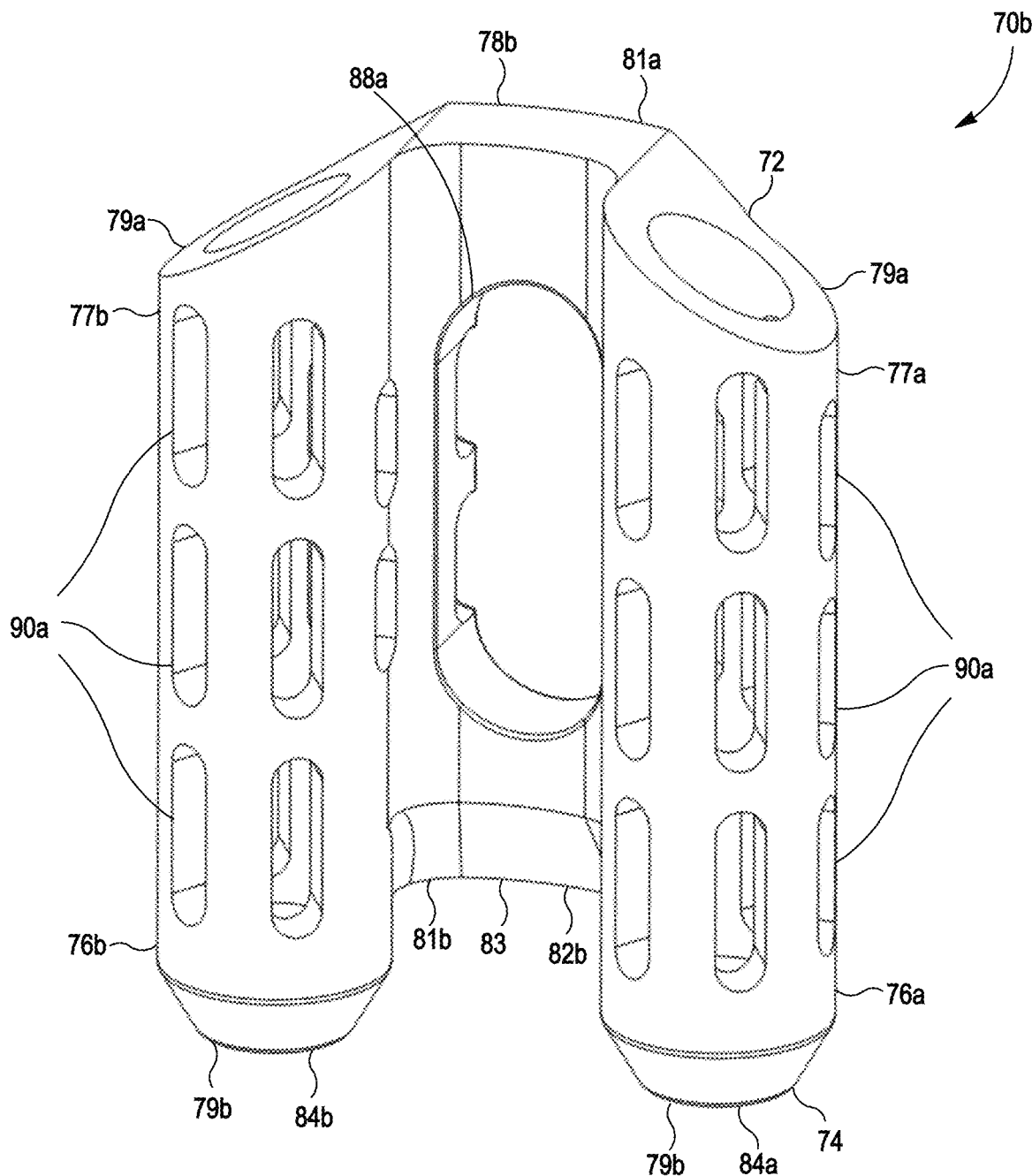
FIG. 9A is a top perspective view of another embodiment of a prosthesis having an offset, arched or radius-shaped bridge section, in accordance with the invention.
Figure 9B:
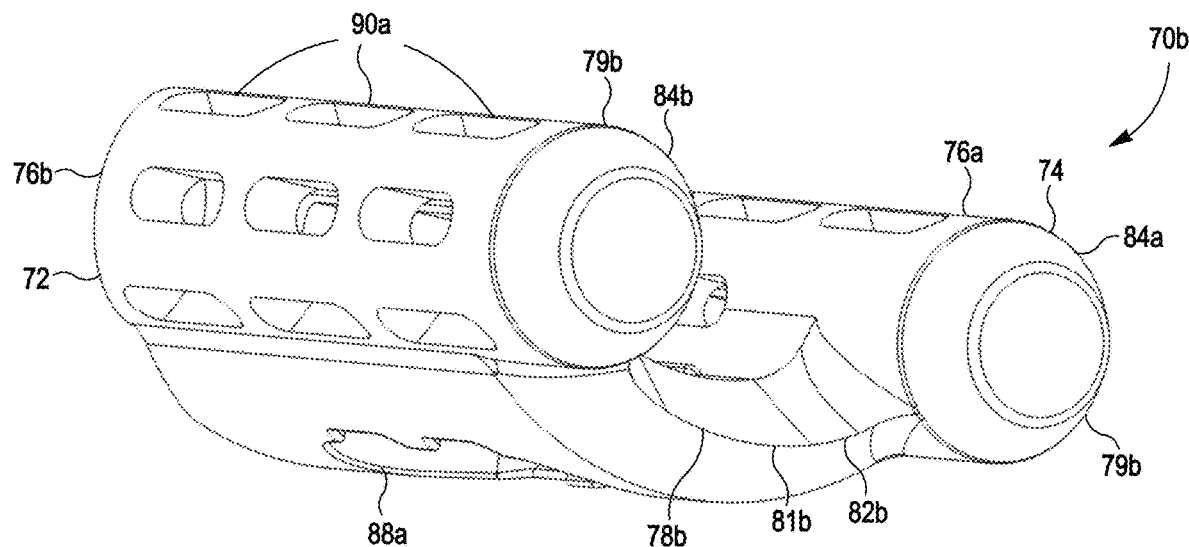
FIG. 9B is a front perspective view of the prosthesis shown in FIG. 9A, in accordance with the invention.
Figure 9C:
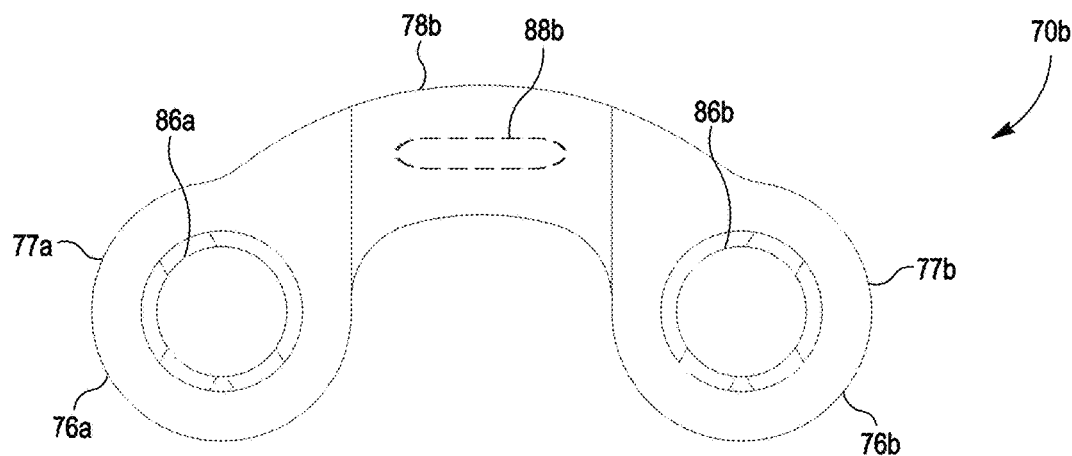
FIG. 9C is an end plan view of the prosthesis shown in FIG. 9A, in accordance with the invention.

Referring now to FIGS. 9A, 9B and 9C, there is shown another embodiment of a prosthesis of the invention (denoted "70b").

As illustrated in FIGS. 9A and 9B, the prosthesis 70b similarly comprises first and second elongated partially cylindrical sections 76a, 76b, which can similarly comprise the same length or different lengths.

As illustrated in FIGS. 9B and 9C, the prosthesis 70b similarly comprises a bridge section or osteotome (in this embodiment, denoted "78b"), which is similarly disposed between and connected to the first and second elongated partially cylindrical sections 76a, 76b.

As further illustrated in FIGS. 9B and 9C, in a preferred embodiment, the bridge section 78b comprises an offset, arched or radius structure that is sized and configured to accommodate the delivery and/or positioning of a primary or supplemental joint support member or device, such as a surgical pin, dowel or screw, e.g., a sacral-alar iliac (S2AI) screw, between the first and second elongated partially cylindrical sections 76a, 76b and above the bridge section 78b.

As illustrated in FIG. 9B, in a preferred embodiment, the distal end 81b of the bridge section 78b, i.e., offset radius structure, similarly comprises a taper region 82b, which is similarly configured and adapted to cut into and through at least articular cartilage and cortical bone.

As illustrated in FIG. 9B, in a preferred embodiment, the first and second elongated partially cylindrical sections 76a, 76b similarly comprise slots 90a, which are preferably in communication with the internal prosthesis engagement member lumens 86a, 86b.

According to the invention, the first and second elongated partially cylindrical sections 76a, 76b can further comprise a plurality of holes that are substantially similar to the holes 92 of the prosthesis 70a.

As illustrated in FIG. 9A, in a preferred embodiment, the bridge section 78b similarly comprises central opening 88a.

Figure 11A:
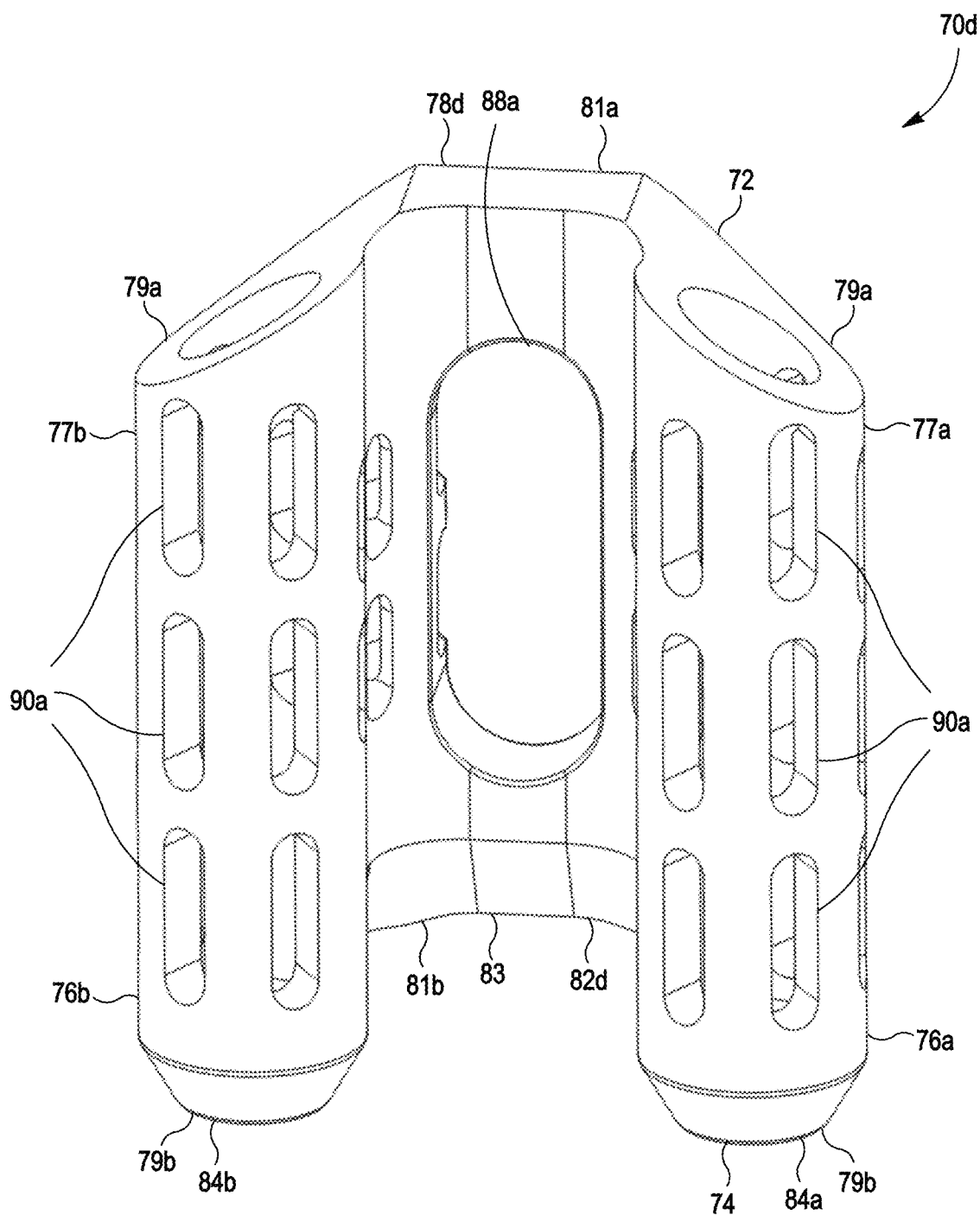
FIG. 11A is a top perspective view of another embodiment of a prosthesis having an offset, U-shaped bridge section, in accordance with the invention.
Figure 11B:
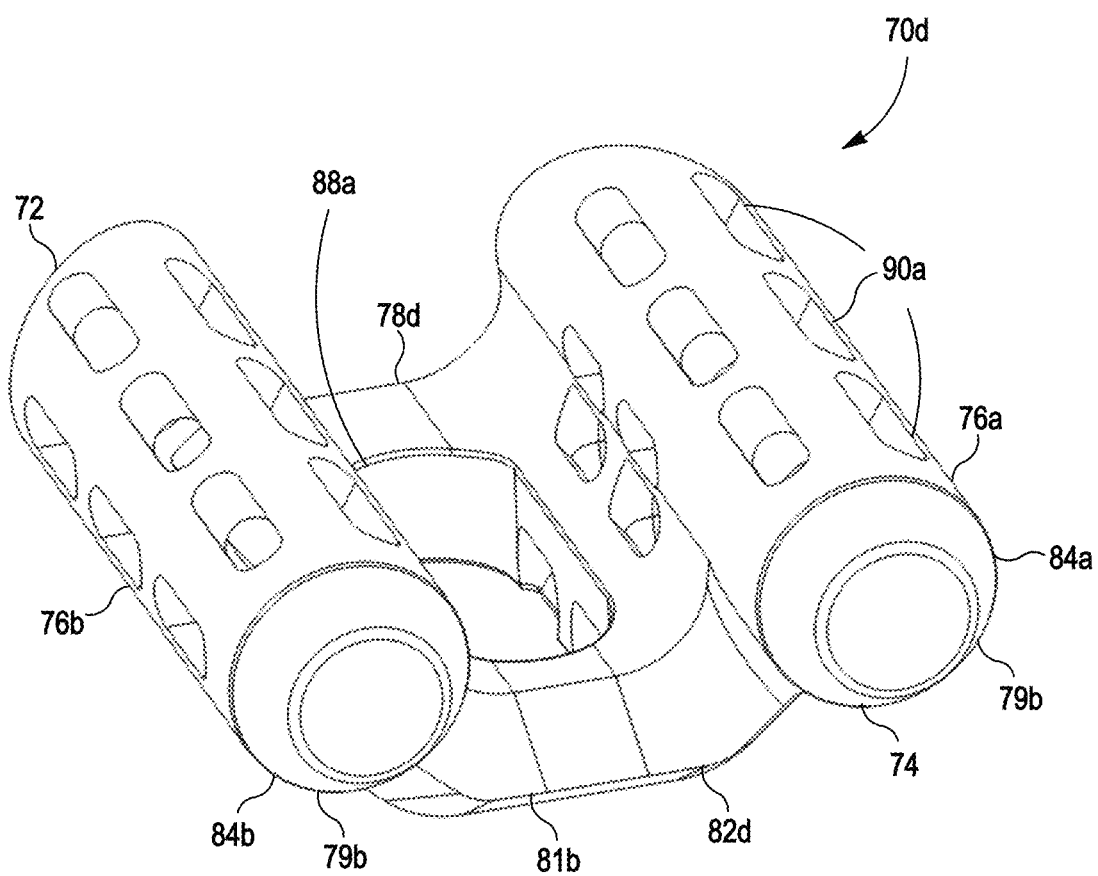
FIG. 11B is a front perspective view of the prosthesis shown in FIG. 11A, in accordance with the invention.
Figure 11C:
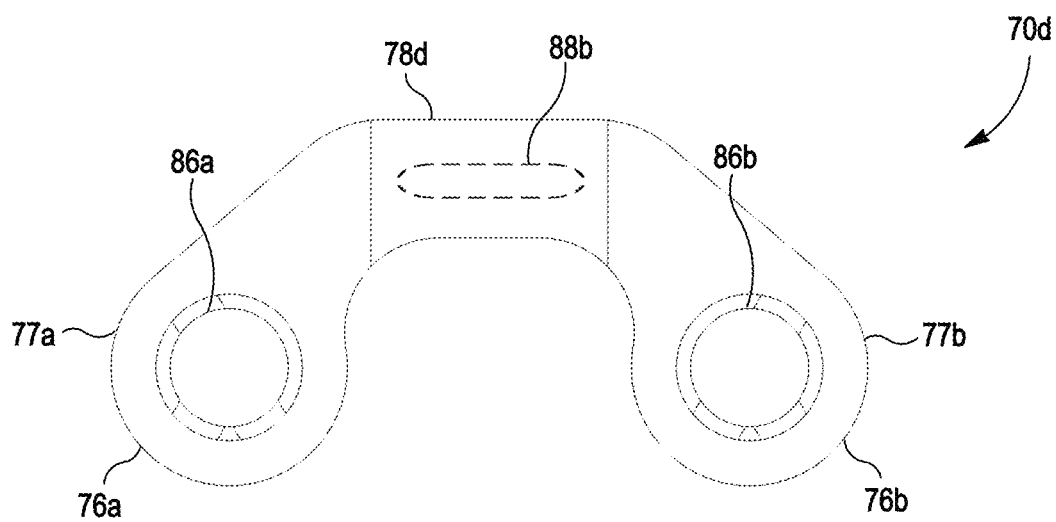
FIG. 11C is an end plan view of the prosthesis shown in FIG. 11A, in accordance with the invention.

As illustrated in FIG. 11C, according to the invention, the bridge section 78b can further comprise the bridge section opening 88b on the proximal end 81a (shown in phantom), which would similarly extend from the bridge section proximal end 81a to the central opening 88a and, hence, be in communication therewith.

According to the invention, the bridge section 78b can further comprise a plurality of slots similar to the slots 90a or holes similar to holes 92, illustrated in FIG. 6A, with and without the central opening 88a.

Figure 10A:
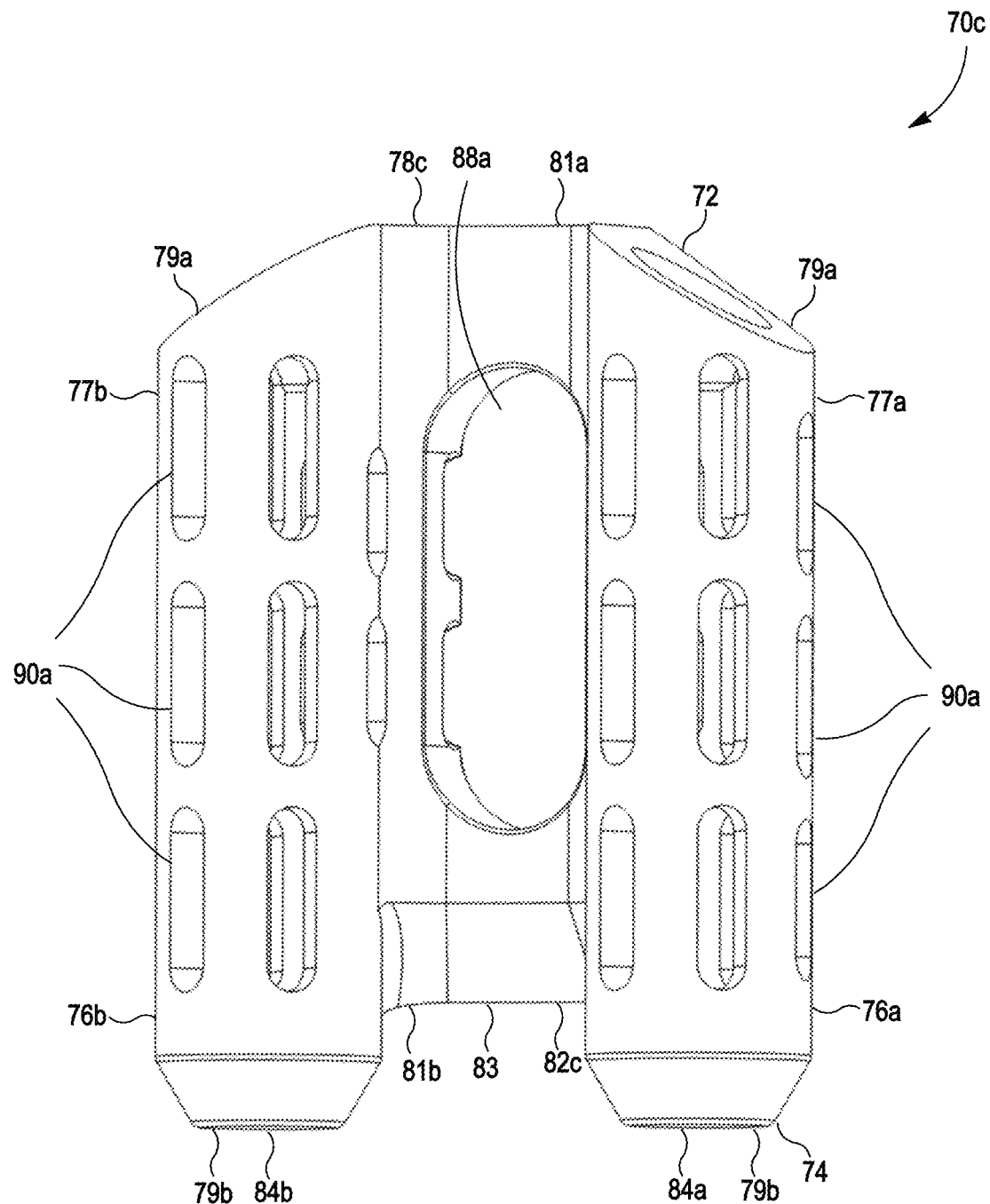
FIG. 10A is a top perspective view of another embodiment of a prosthesis having an offset, V-shaped bridge section, in accordance with the invention.
Figure 10B:
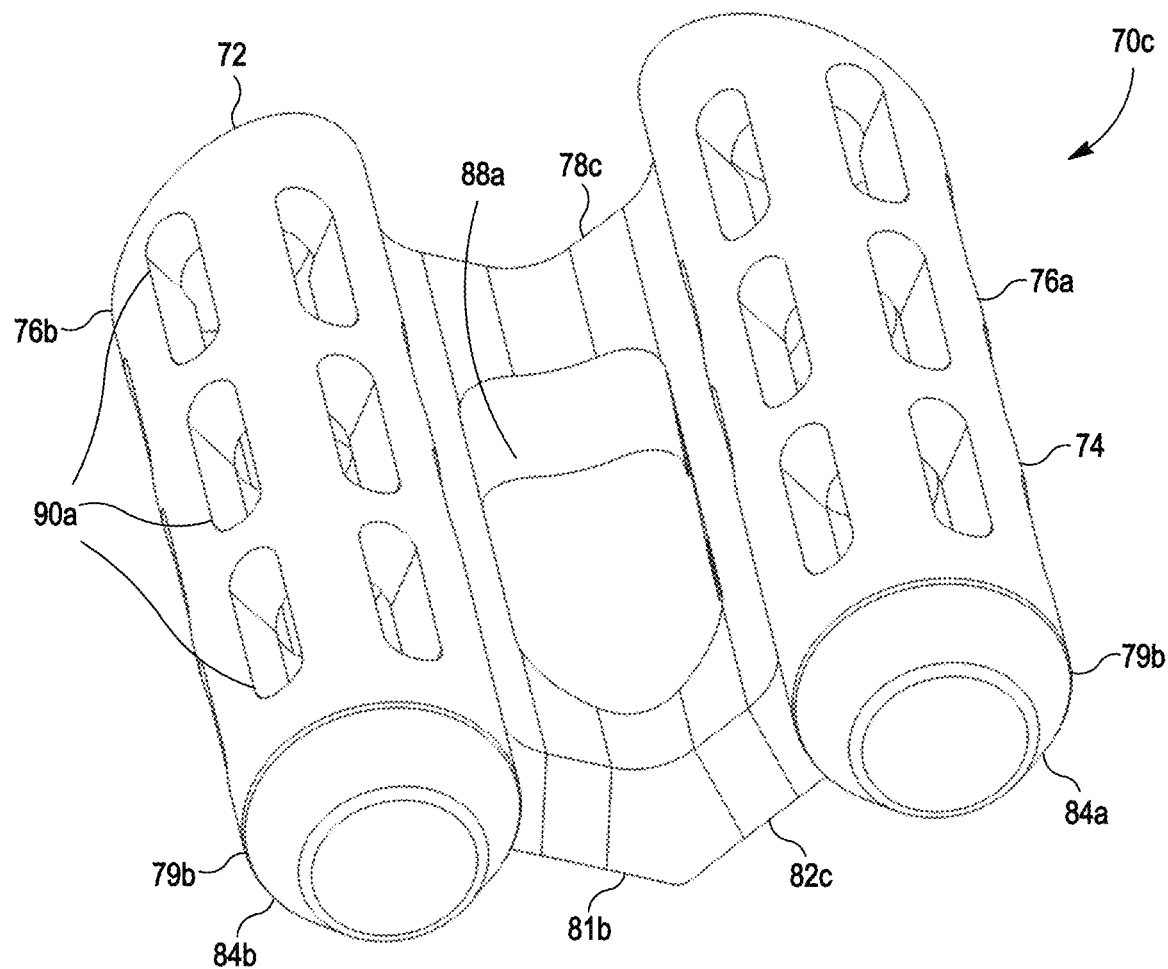
FIG. 10B is a front perspective view of the prosthesis shown in FIG. 10A, in accordance with the invention.
Figure 10C:
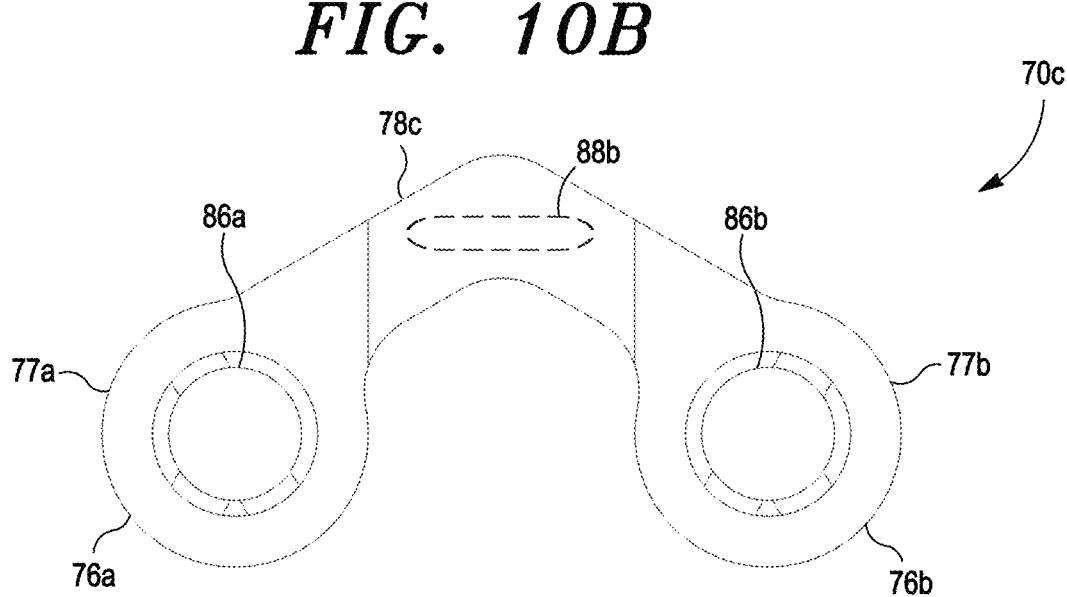
FIG. 10C is an end plan view of the prosthesis shown in FIG. 10A, in accordance with the invention.

Referring now to FIGS. 10A, 10B and 10C, there is shown another embodiment of a prosthesis of the invention (denoted "70c").

As illustrated in FIGS. 10A and 10B, the prosthesis 70c similarly comprises the first and second elongated partially cylindrical sections 76a, 76b, which can similarly comprise the same length or different lengths.

As further illustrated in FIGS. 10B and 10C, the prosthesis 70c similarly comprises a bridge section or osteotome (in this embodiment, denoted "78c"), which is similarly disposed between and connected to the first and second elongated partially cylindrical sections 76a, 76b.

As further illustrated in FIGS. 10B and 10C, in a preferred embodiment, the bridge section 78c comprises an offset, V-shaped structure that is similarly sized and configured to accommodate the delivery and/or positioning of a primary or supplemental joint support member or device, such as a surgical pin, dowel and/or screw, between the first and second elongated partially cylindrical sections 76a, 76b and above the bridge section 78c.

As illustrated in FIG. 10A, in a preferred embodiment, the bridge section 78c similarly comprises central opening 88a.

As illustrated in FIG. 10B, in a preferred embodiment, the distal end 81b of the bridge section 78c, i.e., V-shaped structure, similarly comprises a taper region 82c that is similarly configured to cut into and through at least articular cartilage and cortical bone.

As illustrated in FIG. 10C, according to the invention, the bridge section 78c can similarly comprise the bridge section opening 88b on the proximal end 81a (shown in phantom), which would similarly extend from the bridge section proximal end 81a to the central opening 88a and, hence, be in communication therewith.

According to the invention, the bridge section 78c can further comprise a plurality of slots similar to the slots 90a or holes similar to holes 92, illustrated in FIG. 6A, with and without the central opening 88a.

Referring now to FIGS. 11A, 11B and 11C, there is shown another embodiment of a prosthesis of the invention (denoted "70d").

As illustrated in FIGS. 11A and 11B, the prosthesis 70d similarly comprises the first and second elongated partially cylindrical sections 76a, 76b, which can similarly comprise the same length or different lengths.

As further illustrated in FIGS. 11B and 11C, the prosthesis 70d similarly comprises a bridge section or osteotome (in this embodiment, denoted "78d"), which is similarly disposed between and connected to the first and second elongated partially cylindrical sections 76a, 76b.

As further illustrated in FIGS. 11B and 11C, in a preferred embodiment, the bridge section 78d comprises an offset, U-shaped structure that is similarly sized and configured to accommodate the delivery and/or positioning of a primary or supplemental joint support member or device, such as a surgical pin, dowel and/or screw, between the first and second elongated partially cylindrical sections 76a, 76b and above the bridge section 78d.

As illustrated in FIG. 11A, in a preferred embodiment, the bridge section 78d similarly comprises central opening 88a.

As illustrated in FIG. 11B, in a preferred embodiment, the distal end 81b of the bridge section 78d, i.e., U-shaped structure, similarly comprises a taper region 82d that is similarly configured to cut into and through at least articular cartilage and cortical bone.

As illustrated in FIG. 11C, according to the invention, the bridge section 78d can further comprise the bridge section opening 88b on the proximal end 81a (shown in phantom), which would similarly extend from the bridge section proximal end 81a to the central opening 88a and, hence, in communication therewith.

According to the invention, the bridge section 78d can similarly further comprise a plurality of slots similar to the slots 90a or holes similar to holes 92, illustrated in FIG. 6A, with and without the central opening 88a.

Figure 12A:
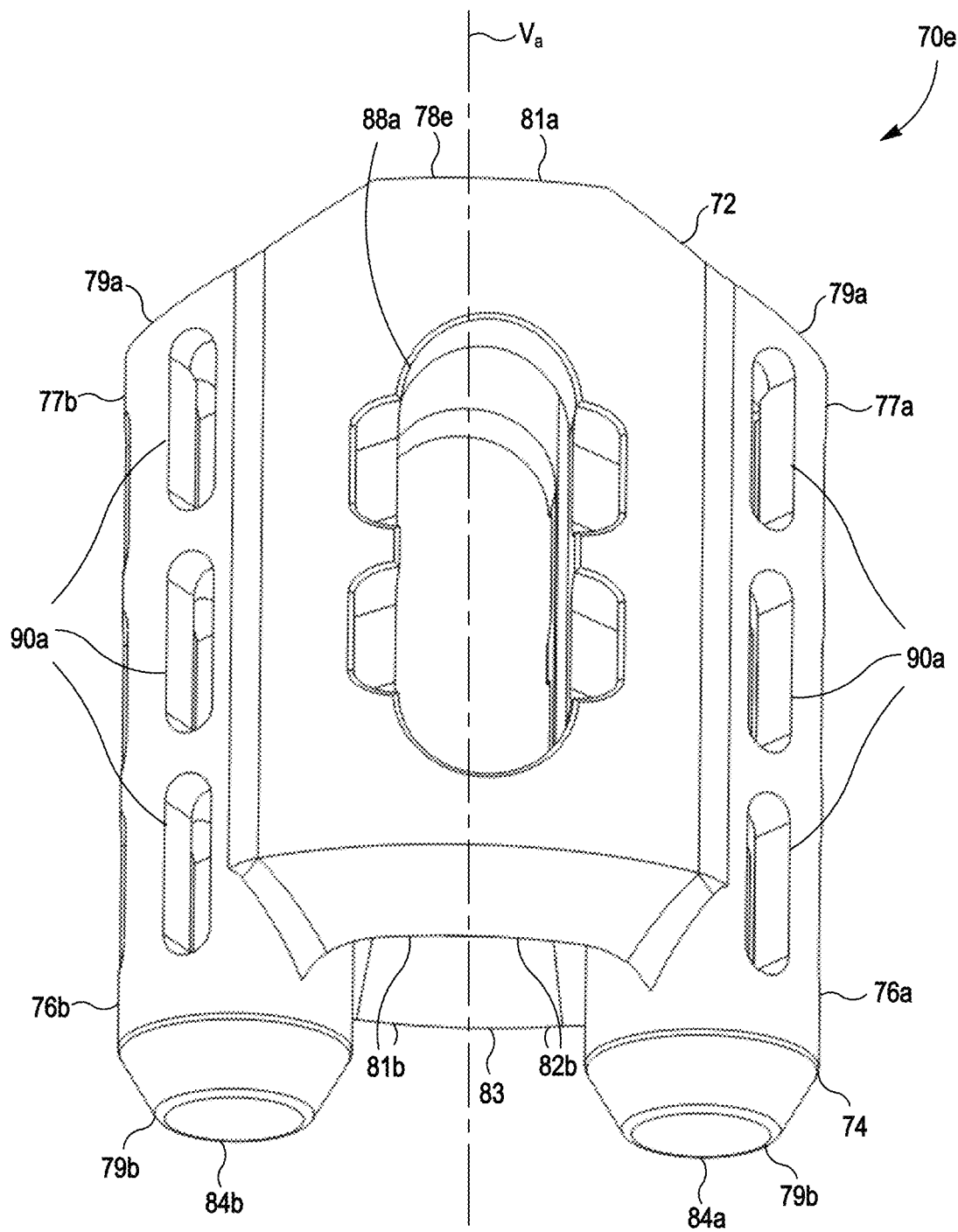
FIG. 12A is a top perspective view of another embodiment of a prosthesis having ovate or arcuate-shaped open bridge section, in accordance with the invention.
Figure 12B:
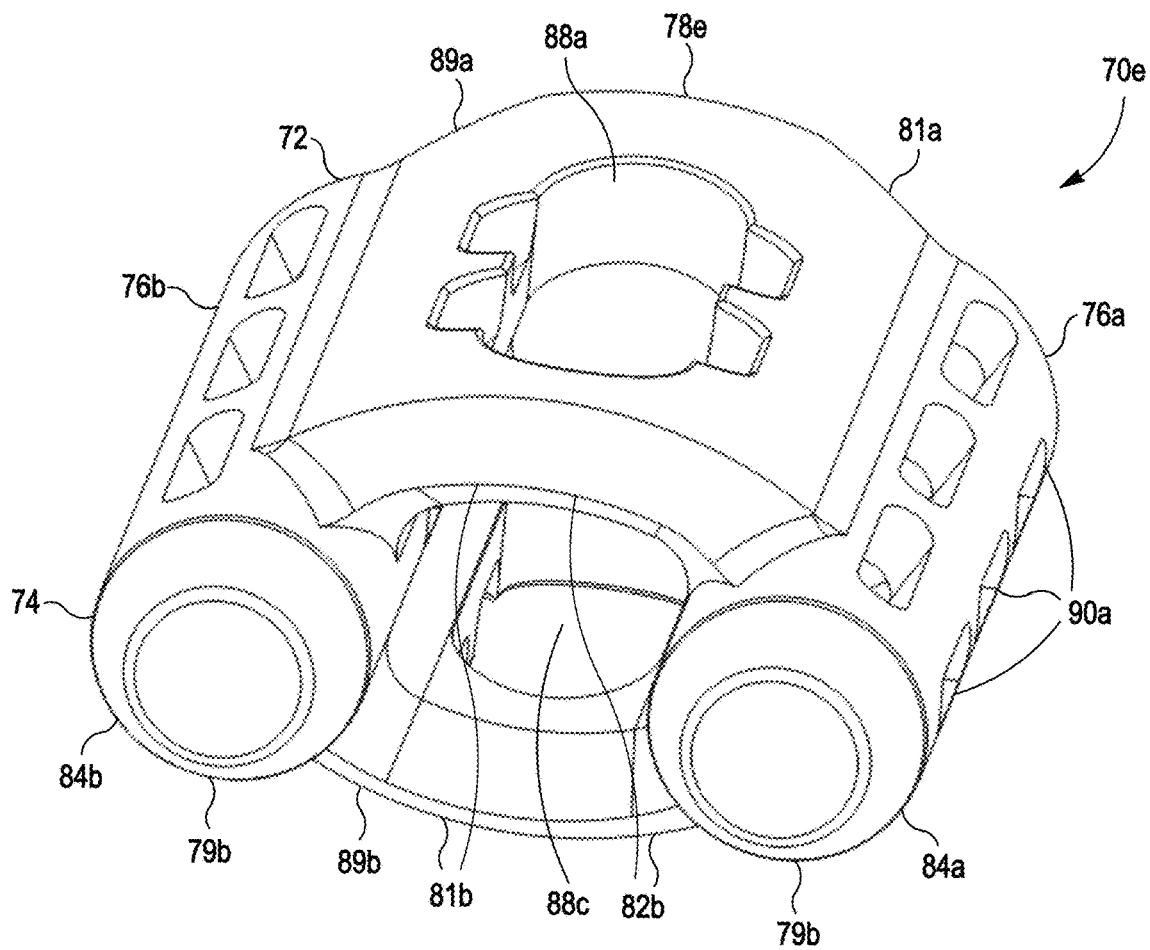
FIG. 12B is a front perspective view of the prosthesis shown in FIG. 12A, in accordance with the invention.
Figure 12C:
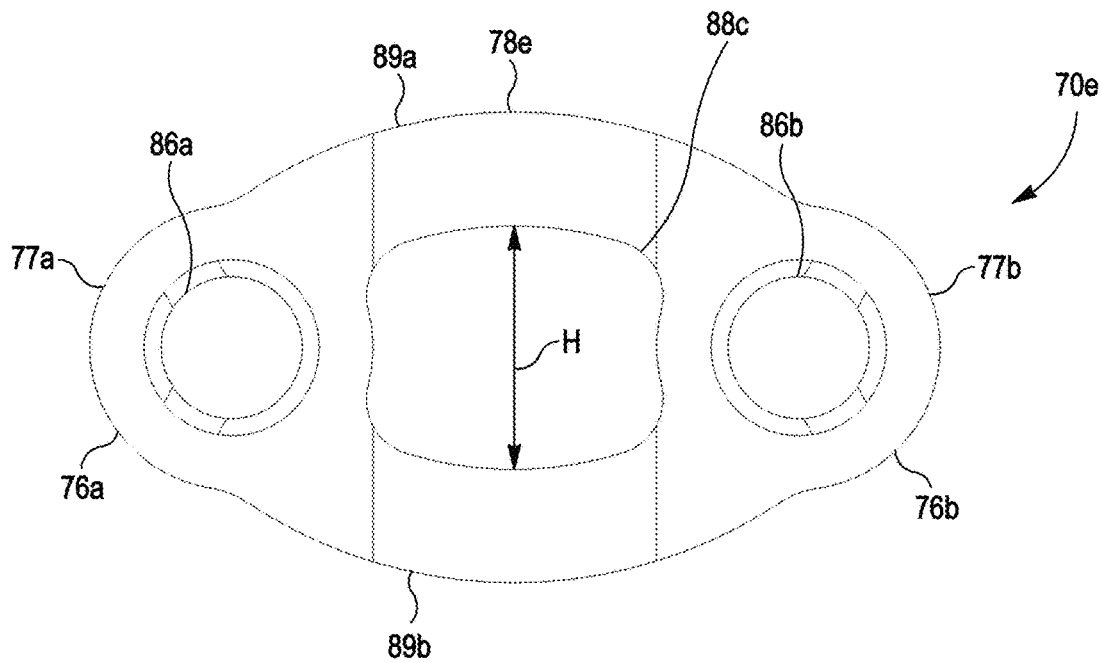
FIG. 12C is an end plan view of the prosthesis shown in FIG. 12A, in accordance with the invention.

Referring now to FIGS. 12A, 12B and 12C, there is shown another embodiment of a prosthesis of the invention (denoted "70e").

As illustrated in FIGS. 12A and 12B, the prosthesis 70e similarly comprises the first and second elongated partially cylindrical sections 76a, 76b, which can similarly comprise the same length or different lengths.

As further illustrated in FIGS. 12B and 12C, the prosthesis 70e similarly comprises a bridge section (in this embodiment, denoted "78c"), which is similarly disposed between and connected to the first and second elongated partially cylindrical sections 76a, 76b.

As further illustrated in FIGS. 12B, and 12C, in a preferred embodiment, the bridge section 78e comprises an ovate-shaped open structure comprising top and bottom sections 89a, 89b, which are spaced apart and, hence, provide an opening 88c therebetween.

According to the invention, the opening 88c between the top and bottom bridge sections 89a, 89b is similarly sized and configured to accommodate the delivery and/or positioning of a primary or supplemental joint support member or device, such as a surgical pin, dowel or screw, between the top and bottom bridge sections 89a, 89b.

In a preferred embodiment, the opening 88c comprises a minimum height (denoted "H") proximate the vertical axis (denoted "$V_a$") in the range of 25.0 mm to 17.0 mm, more preferably, in the range of 20.0 mm to 17.0 mm.

As illustrated in FIG. 12A, in a preferred embodiment, the top and bottom bridge sections 89a, 89b similarly comprise central opening 88a.

As illustrated in FIG. 12B, in a preferred embodiment, the distal ends 81b of the top and bottom bridge sections 89a, 89b similarly comprise taper regions 82b that are configured to cut into and through at least articular cartilage and cortical bone.

According to the invention, the top and/or bottom bridge sections 89a, 89b can similarly further comprise a plurality of slots similar to the slots 90a or holes similar to holes 92, illustrated in FIG. 6A, with and without the central openings 88a.

Figure 13A:
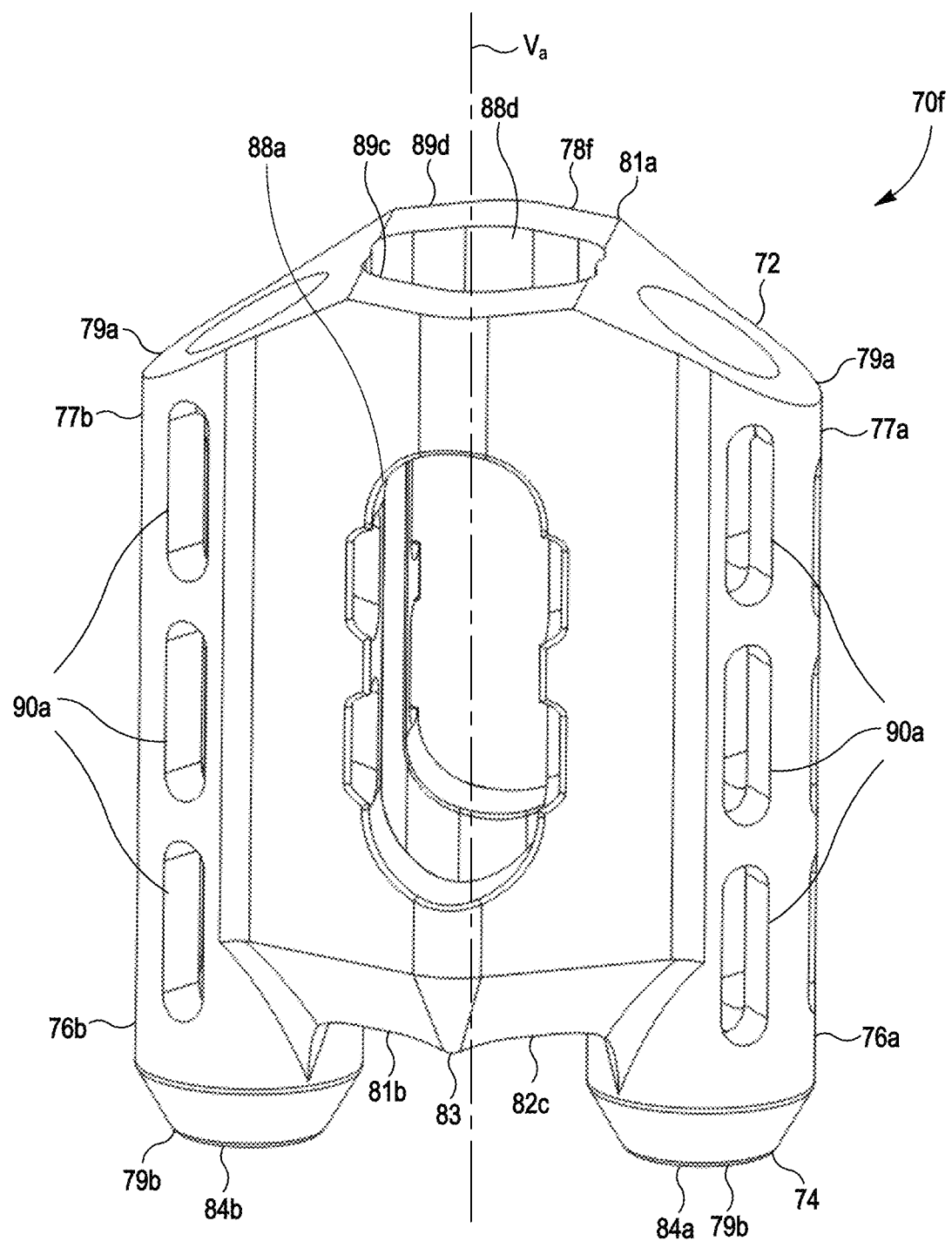
FIG. 13A is a top perspective view of another embodiment of a prosthesis having V-shaped open bridge section, in accordance with the invention.
Figure 13B:
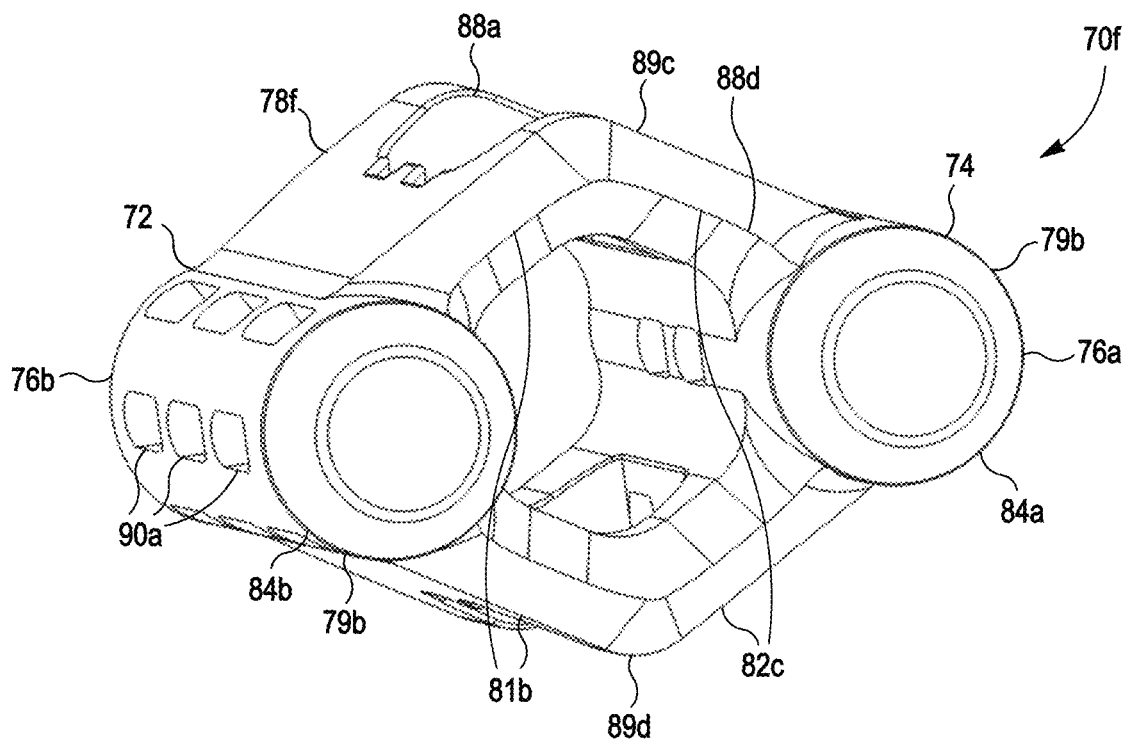
FIG. 13B is a front perspective view of the prosthesis shown in FIG. 13A, in accordance with the invention.
Figure 13C:
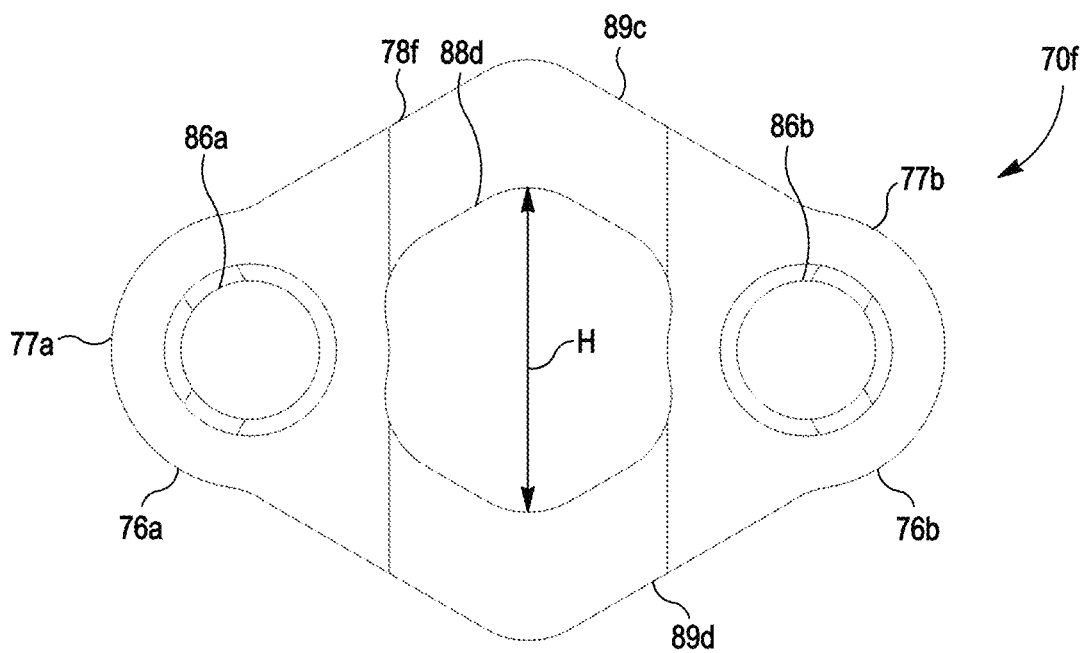
FIG. 13C is an end plan view of the prosthesis shown in FIG. 13A, in accordance with the invention.

Referring now to FIGS. 13A, 13B and 13C, there is shown another embodiment of a prosthesis of the invention (denoted "70f").

As illustrated in FIGS. 13A and 13B, the prosthesis 70f similarly comprises the first and second elongated partially cylindrical sections 76a, 76b, which can similarly comprise the same length or different lengths.

As illustrated in FIGS. 13B and 13C, the prosthesis 70f similarly comprises a bridge section or osteotome (in this embodiment, denoted "78f"), which is similarly disposed between and connected to the first and second elongated partially cylindrical sections 76a, 76b.

As further illustrated in FIGS. 13B and 13C, in a preferred embodiment, the bridge section 78f comprises a V-shaped open structure comprising top and bottom bridge sections 89c, 89d, which are spaced apart and, hence, provide an opening 88d therebetween.

According to the invention, the opening 88d between the top and bottom bridge sections 89c, 89d is similarly sized and configured to accommodate the delivery and/or positioning of a primary or supplemental joint support member or device, such as a surgical pin, dowel or screw, between the top and bottom bridge sections 89c, 89d.

In a preferred embodiment, the opening 88d similarly comprises a minimum height (H) proximate the vertical axis ($V_a$) in the range of 25.0 mm to 17.0 mm, more preferably, in the range of 20.0 mm to 17.0 mm.

As illustrated in FIGS. 13A and 13B, in a preferred embodiment, the top and bottom bridge sections 89c, 89d comprise central opening 88a.

As illustrated in FIG. 13B, in a preferred embodiment, the distal ends 81b of the top and bottom bridge sections 89c, 89d similarly comprise taper regions 82c that are configured to cut into and through at least articular cartilage and cortical bone.

According to the invention, the top and/or bottom bridge sections 89c, 89d can similarly further comprise a plurality of slots similar to the slots 90a or holes similar to holes 92, illustrated in FIG. 6A, with and without the central openings 88a.

Figure 14A:
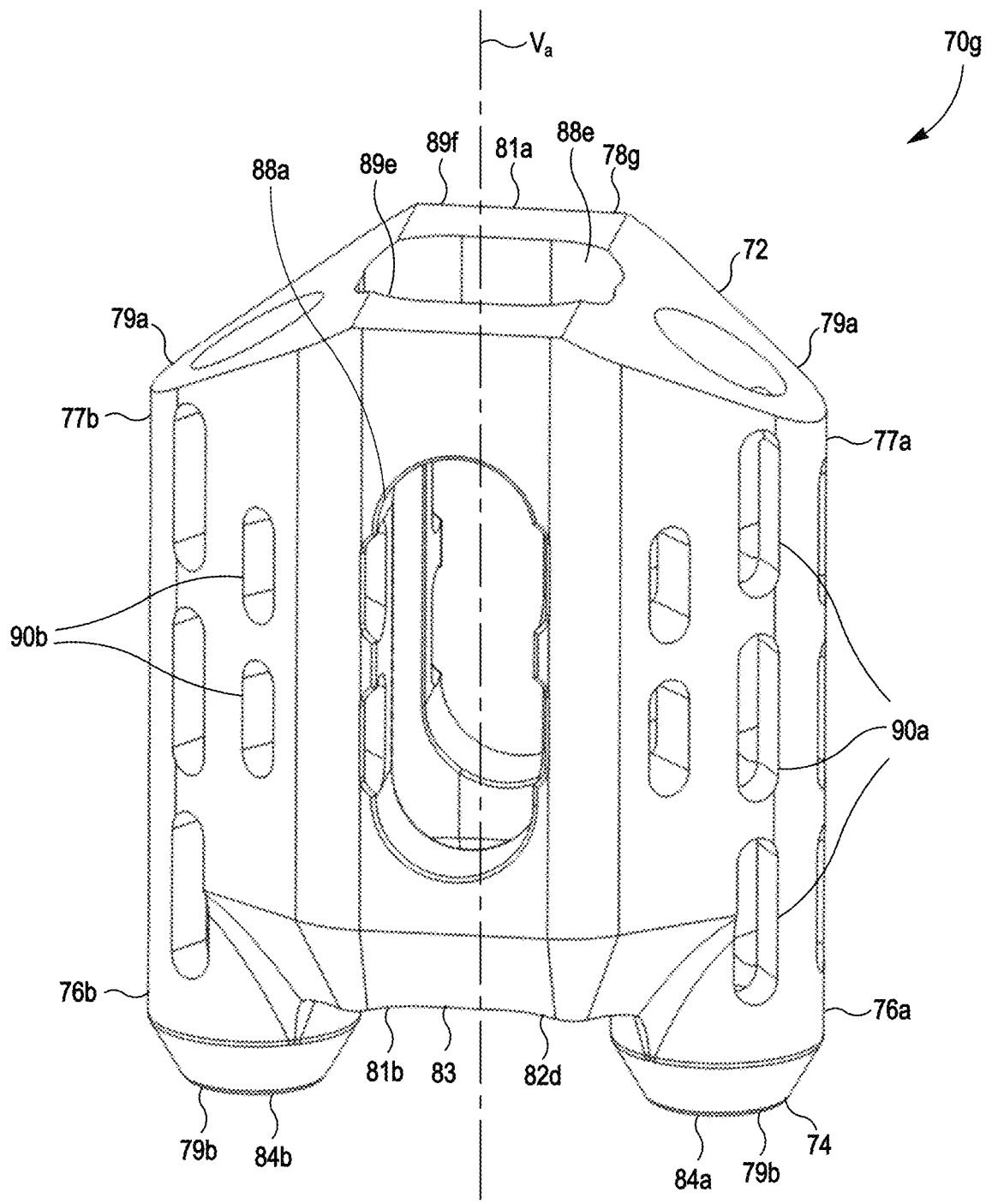
FIG. 14A is a top perspective view of another embodiment of a prosthesis having a rectangular-shaped open bridge section, in accordance with the invention.
Figure 14B:
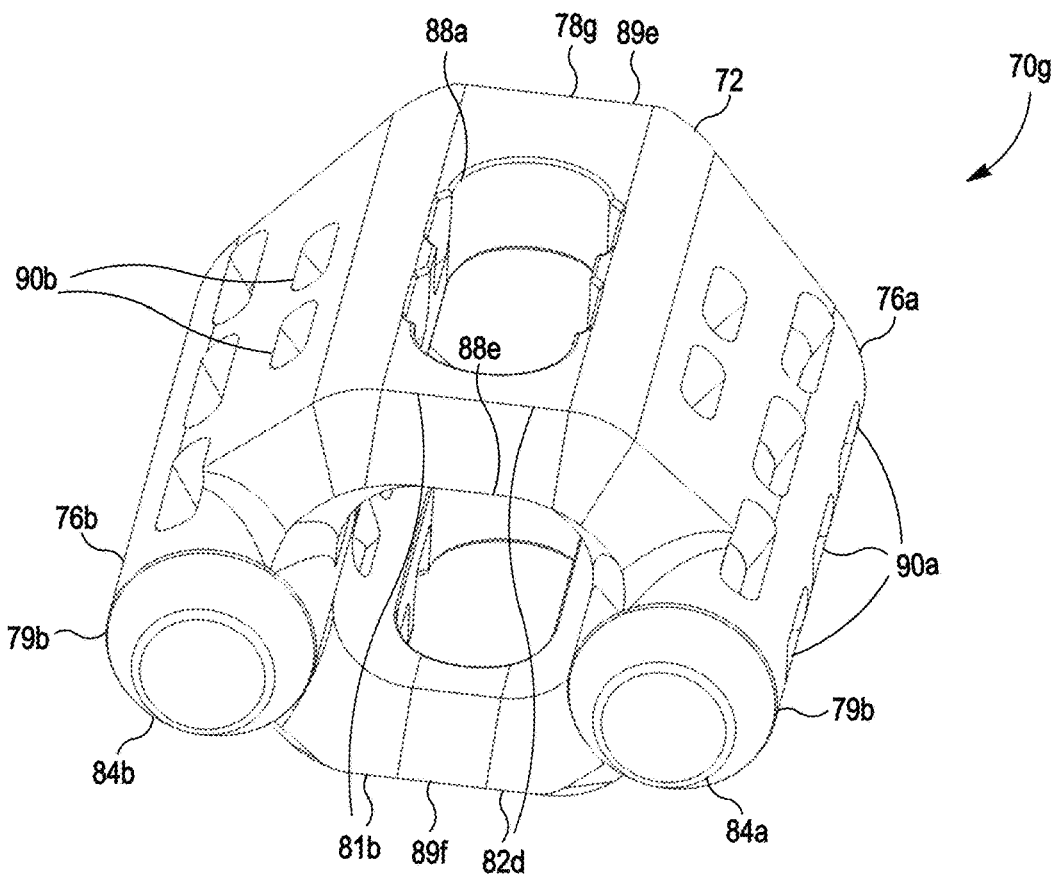
FIG. 14B is a front perspective view of the prosthesis shown in FIG. 14A, in accordance with the invention.
Figure 14C:
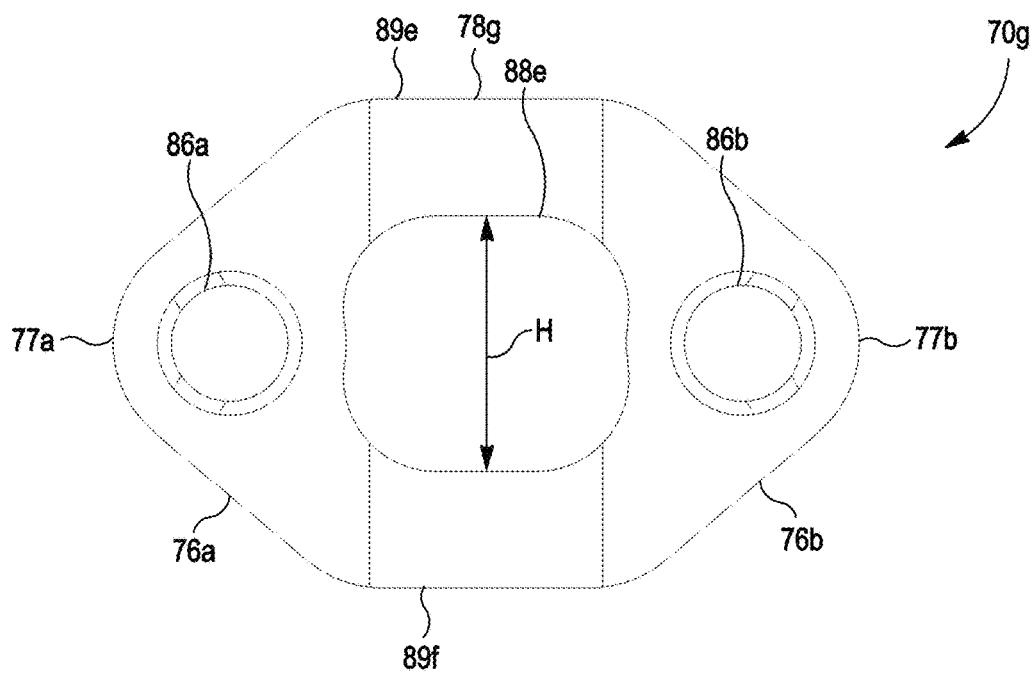
FIG. 14C is an end plan view of the prosthesis shown in FIG. 14A, in accordance with the invention.

Referring now to FIGS. 14A, 14B and 14C, there is shown another embodiment of a prosthesis of the invention (denoted "70g").

As illustrated in FIGS. 14A, 14B and 14C, the prosthesis 70g similarly comprises the first and second elongated partially cylindrical sections 76a, 76b, which can similarly comprise the same length or different lengths.

As illustrated in FIGS. 14A and 14B, the prosthesis 70g similarly comprises a bridge section (in this embodiment, denoted "78g"), which is similarly disposed between and connected to the first and second elongated partially cylindrical sections 76a, 76b.

As further illustrated in FIGS. 14B and 14C, in a preferred embodiment, the bridge section 78g comprises a rectangular shaped open structure comprising top and bottom bridge sections 89e, 89f, which are similarly spaced apart and, hence, provide an opening 88c therebetween.

According to the invention, the opening 88e between the top and bottom bridge sections 89e, 89f is similarly sized and configured to accommodate the delivery and/or positioning of a primary or supplemental joint support member or device, such as a surgical pin, dowel or screw, between the top and bottom bridge sections 89c, 89f.

In a preferred embodiment, the opening 88e similarly comprises a minimum height (H) proximate the vertical axis ($V_a$) in the range of 25.0 mm to 17.0 mm, more preferably, in the range of 20.0 mm to 17.0 mm.

As illustrated in FIGS. 14A and 14B, in a preferred embodiment, the top and bottom bridge sections 89e, 89f similarly comprise central opening 88a.

As illustrated in FIG. 14B, in a preferred embodiment, the distal ends 81b of the top and bottom bridge sections 89e, 89f similarly comprise taper regions 82d that are configured to cut into and through at least articular cartilage and cortical bone.

As illustrated in FIGS. 14A and 14B, the top and bottom bridge sections 89c, 89d comprise a plurality of slots 90b, which preferably are in communication with the opening 88c between top and bottom bridge sections 89c, 89f.

According to the invention, the top and/or bottom bridge sections 89c, 89f can similarly further comprise a plurality of holes similar to holes 92, illustrated in FIG. 6A.

As indicated above, prostheses 70a, 70b, 70c, 70d, 70e, 70f, and 70g, discussed above, are specifically adapted to be advanced into SI joints in a posterior trajectory, wherein the prostheses transfix the SI joints, as defined herein.

Figure 18:
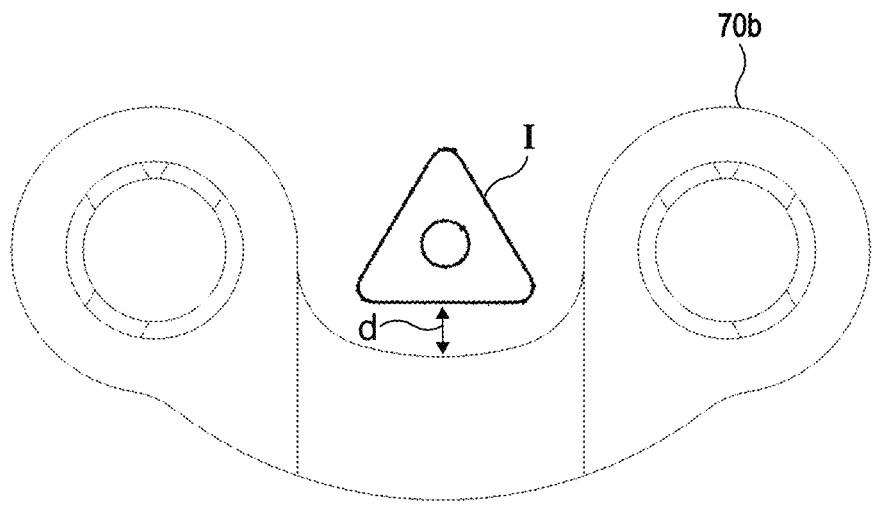
FIG. 18 is an illustration of the prosthesis shown in FIG. 9A with a surgical implant, i.e., orthopedic dowel, disposed between the elongated sections thereof, in accordance with the invention.

According to the invention, the prostheses with offset bridge structures, i.e., prostheses 70b, 70c, 70d, can be advanced into SI joints in different orientations. In a preferred embodiment, the orientations include (i) a first orientation, wherein the offset bridge structure is disposed on a first plane, whereby the offset bridge structure is disposed proximate the bottom of a prior surgical implant (e.g., surgical pin, dowel or screw), such as illustrated in FIG. 18, or a new surgical implant, and (ii) a second orientation, wherein the offset bridge structure is disposed on a second plane, whereby the offset bridge structure is disposed proximate the top of a prior surgical implant or a new surgical implant.

In a preferred embodiment, when prostheses 70b, 70c, 70d are advanced into SI joints, the prior surgical implant or new surgical implant is spaced a distance in the range of 4.0 mm to 7.0 mm from the offset bridge structures thereof.

According to the invention, the prostheses of the invention, i.e., prostheses 70a, 70b, 70c, 70d, 70e, 70f, and 70g, can comprise various biocompatible materials, including metals and metal alloys, such as titanium, stainless-steel, cobalt-chromium alloys, and nickel-titanium alloys.

Prostheses 70a, 70b, 70c, 70d, 70e, 70f, and 70g can also comprise various biocompatible polymers, including, without limitation, reinforced polymers, such as carbon fiber reinforced polymers and metal-framed polymers.

According to the invention, prostheses 70a, 70b, 70c, 70d, 70e, 70f, and 70g can also comprise porous structures to facilitate (i) adhesion of prostheses to a post-prosthesis insertion SI joint opening of the invention; particularly, post-prosthesis insertion SI joint openings 300, 400 and, thereby, to SI joint bone structures, i.e., sacrum and ilium bone structures, and (ii) bone or osseous tissue ingrowth into the prostheses.

According to the invention, prostheses 70a, 70b, 70c, 70d, 70e, 70f, and 70g can also comprise various exterior surface textures and roughness to facilitate or enhance engagement of the prostheses to a post-prosthesis insertion SI joint opening, such as post-prosthesis insertion SI joint openings 300, 400, and, thereby, to SI joint bone structures, i.e., sacrum and ilium bone structures, and/or maintain engagement thereto and positioning therein.

The surface of the prostheses can, thus, comprise a roughness grade number of N1 (Ra=~0.025 μm), N2 (Ra=~0.05 μm), N3 (Ra=~0.1 μm), N4 (Ra=~0.2 μm), N5 (Ra=~0.4 μm), N6 (Ra=~0.08 μm), N7 (Ra=~1.6 μm), N8 (Ra=~3.2 μm), N9 (Ra=~6.3 μm), N10 (Ra=~12.5 μm), N11 (Ra=~25 μm) or N12 (Ra=~50 μm).

In some embodiments of the invention, prostheses 70a, 70b, 70c, 70d, 70e, 70f, and 70g can further comprise an outer coating.

In some embodiments, the outer coating comprises a biocompatible and, preferably, biodegradable adhesive composition. According to the invention, suitable adhesive compositions include, without limitation, poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol and combinations thereof; fibrin-based compositions, collagen-based compositions, including collagen and poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ M Xact, Coseal® and ReSure Sealant; polysaccharide-based compositions, polypeptide-based compositions, and radiation curable materials, such as poly(glycerol-co-sebacate) acrylate (PGSA), discussed below.

In some embodiments, the outer coating comprises a biologically active composition comprising one of the aforementioned biologically active agents (referred to generally as fixation catalysts in Co-pending priority application Ser. No. 13/857,977) or a pharmacological composition comprising one of the forementioned pharmacological agents.

In some embodiments, the outer coating comprises one of the aforementioned polymers and/or compositions comprising same.

In some embodiments, the aforementioned polymer compositions comprise one or more of the aforementioned biologically active agents or pharmacological agents.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly (ε-caprolactone) (PGS-PCL) composites, and compositions comprising same.

As set forth in Co-pending U.S. application Ser. No. 17/463,779, PGS and derivatives thereof possess a unique property of inducing remodeling of damaged osseous or bone tissue, such as at pilot SI joint openings, and, hence, healing of the associated bone structures when disposed proximate thereto.

As set forth in Loh, et al., *Poly(glycerol sebacate) Biomaterial: Synthesis and Biomedical Applications*, Journal of Materials Chemistry B, vol. 3(39), pp. 7641-7652 (2015) and indicated in Table 1 below, a further seminal property of PGS is that its physical state can be modulated during synthesis by controlling the "degree of esterification" via at least one crosslinking agent, e.g., methylene diphenyl diisocyanate (MDI).

TABLE 1

| Degree of Esterification | Physical State |
| --- | --- |
| ≤46% | Solid (Brittle Wax) |
| ~47%-64% | Semi-Solid (Soft Wax) |
| ~65%-75% | Viscous Liquid |
| ~76%-83% | Sticky Elastomer |
| ≥84% | Elastomer |

According to the invention, any suitable degree of esterification of PGS can be employed for PGS when employed in or for PGS based outer coatings (i.e., polymer compositions comprising PGS) and biologically active agent compositions of the invention.

In some embodiments, the PGS based outer coatings comprise a degree of esterification in the range of ~76%-83%, whereby the PGS exhibits adhesive properties, which will enhance engagement of the prostheses of the invention; particularly prostheses 70a, 70b, 70c, 70d, 70e, 70f, and 70g to the post-prosthesis insertion SI joint openings 300, 400 and, thereby, to the SI joint bone structures, i.e., sacrum and ilium bone structures.

As is well established, the physical state of poly(glycerol-co-sebacate) acrylate (PGSA) can also be modulated by combining the PGSA with a suitable photoinitiator and subjecting the PGSA to radiation.

Indeed, as set forth in Nijst, et al., *Synthesis and Characterization of Photocurable Elastomers from Poly(Glycerol-Co-Sebacate)*, Biomacromolecules, vol. 8, no. 10, pp. 3067-3073 (2007), PGSA can be induced to transition from a liquid or flowable state to a solid elastomer state when combined with a photoinitiator, such as 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl and methylcyclopentadienyl manganese tricarbonyl, and subjected to radiation, such as visible light; particularly, radiation in the range of approximately 380.0 nm-750.0 nm, and ultraviolet (UV) light, particularly, radiation in the range of 10.0 nm-400.0 nm.

Thus, in some embodiments, a composition comprising PGSA (also referred to hercin as a "PGSA based composition" and "fixation composition") is employed to enhance the engagement of prostheses 70a, 70b, 70c, 70d, 70e, 70f, and 70g to post-prosthesis insertion SI joint openings, such as post-prosthesis insertion SI joint openings 300, 400, and, thereby, SI joint bone structures, i.e., sacrum and ilium bone structures.

In some embodiments, the PGSA based composition (in a flowable state) is thus disposed in the internal prosthesis engagement member lumens 86a, 86b of prostheses 70a, 70b, 70c, 70d, 70c, 70f, and 70g, whereby the PGSA based composition is dispersed when the prostheses are positioned in the dysfunctional SI joint and fills any gaps between the prostheses and post-prosthesis insertion SI joint openings of the invention; particularly, post-prosthesis insertion SI joint openings 300, 400, and is thereafter cured via radiation and solidified, whereby the solidified PGSA enhances the engagement of the prostheses to the post-prosthesis insertion SI joint openings and, thereby, to the sacrum and ilium bone structures.

PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS based outer coatings and PGS and PGSA based compositions further comprise one or more of the aforementioned biologically active or pharmacological agents.

As indicated above, in some embodiments of the invention, the system for stabilizing dysfunctional SI joints further comprises an image capture apparatus configured and adapted to capture images reflecting positions and/or orientations of the elongated guide probe and/or defect creation assembly when disposed in the body, and, particularly, during advancement of the elongated guide probe and defect creation assembly toward and into the dysfunctional SI joint.

According to the invention, suitable image capture apparatus comprise a fluoroscope, a CT system, an ultrasound system, a radiography system, and a magnetic resonance imaging system.

As indicated above, in some embodiments of the invention, the system for stabilizing dysfunctional SI joints further comprises a drill guide assembly that facilitates proper placement of (i) the elongated guide probe 20 in the dysfunctional SI joint, and (ii) the pilot SI joint openings 100, 200 of the invention and, hence, sacrum and ilium portions thereof, and, thereby, placement of prosthesis 70a (and prostheses 70b, 70c, 70d, 70e, 70f, and 70g of the invention) in the dysfunctional SI joint.

Figure 15A:
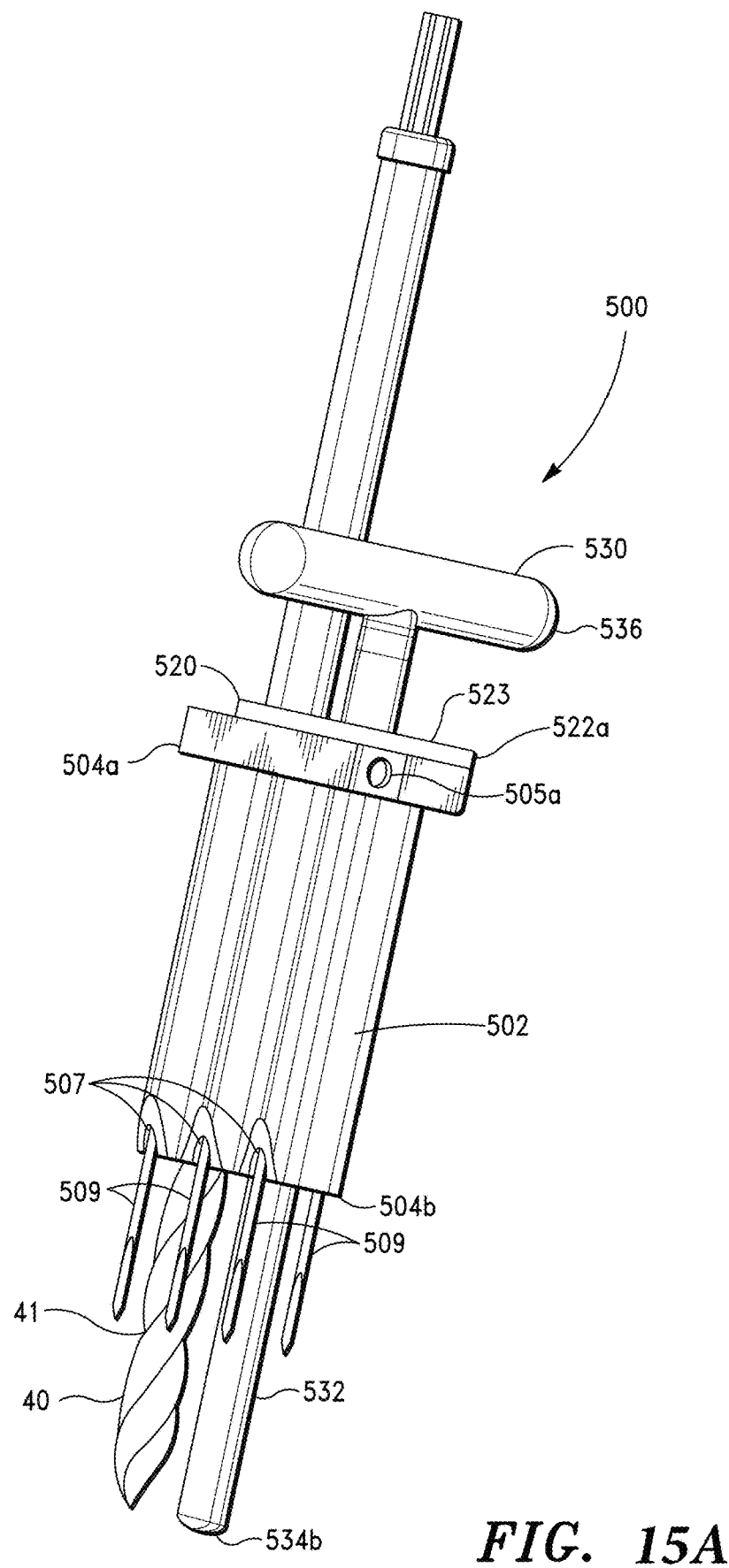
FIG. 15A is a perspective view of one embodiment of drill guide assembly, in accordance with the invention.

Referring now to FIG. 15A, there is shown a preferred embodiment of a drill guide assembly 500 of the invention.

As illustrated in FIG. 15A, the drill guide assembly 500 comprises an access sleeve 502, drill guide 520 and a guide pin 530.

Figure 15B:
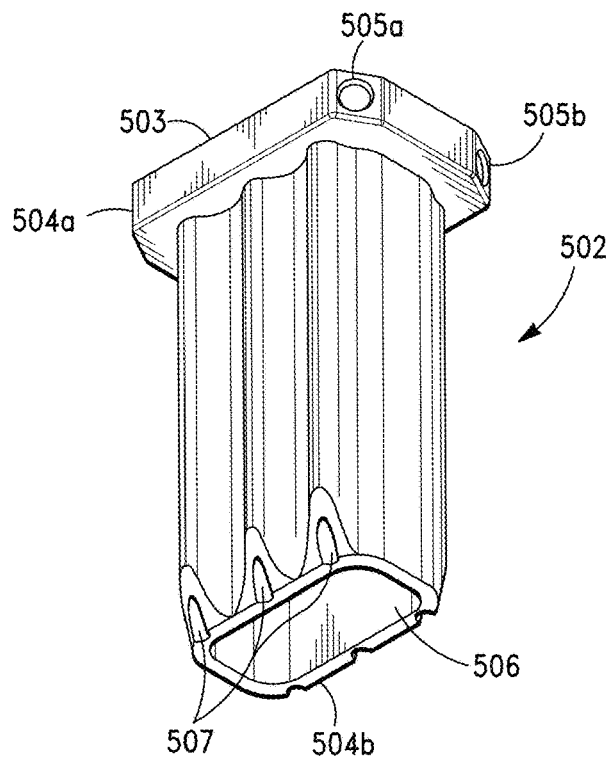
FIG. 15B is a perspective view the access sleeve of the drill guide assembly shown in FIG. 15A, in accordance with the invention.
Figure 15C:
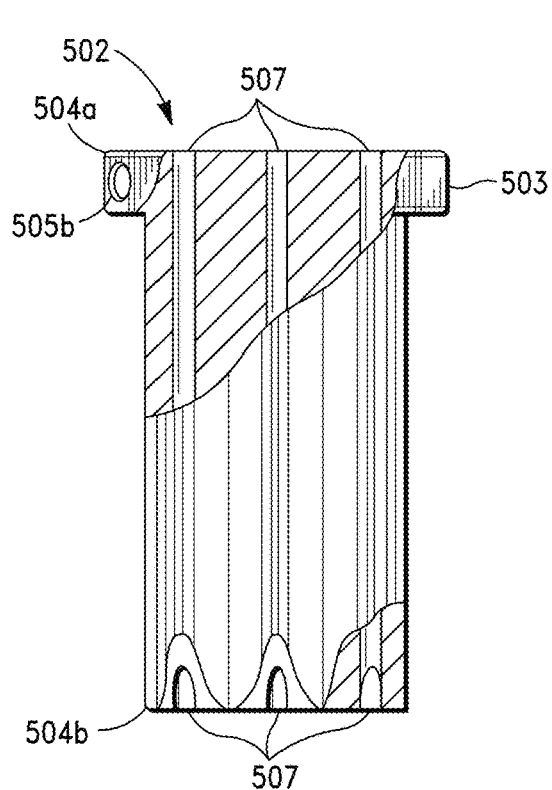
FIG. 15C is a front plan view of the access sleeve shown in FIG. 15B, in accordance with the invention.
Figure 15D:
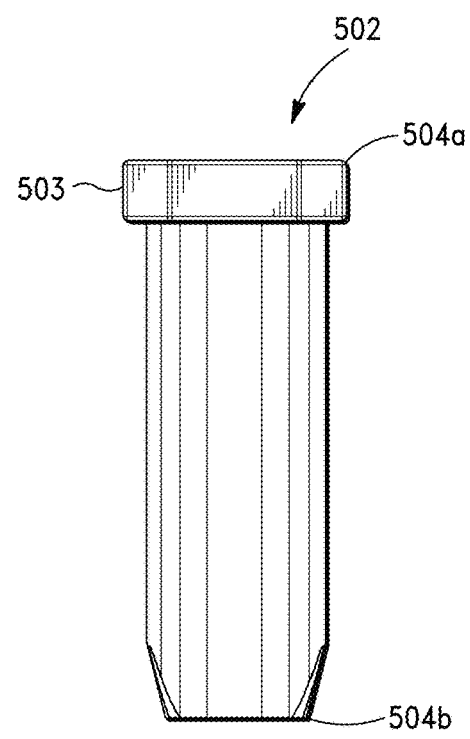
FIG. 15D is a right-side plan view of the access sleeve shown in FIG. 15B, in accordance with the invention.

Referring now to FIGS. 15B-15D, there is shown a preferred embodiment of the access sleeve 502.

As illustrated in FIGS. 15B-15D, the access sleeve 502 comprises proximal and distal ends 504a, 504b, and an internal opening 506 that extends from the proximal end 504a to the distal end 504b of the access sleeve 502, and a plurality of lumens 507, which, as illustrated in FIG. 15A, are sized and configured to receive and position Kirschner wires (K-wires) 509 or similar pin structures therein.

As illustrated in FIG. 15A, in a preferred embodiment, the access sleeve internal opening 506 is sized and configured to receive and position the drill guide 520 therein.

As further illustrated in FIGS. 15B and 15D, the proximal end 504a of the access sleeve 502 comprises a planar region 503, which, as illustrated in FIG. 15A, is configured to seat the proximal end 522a of the drill guide 520 (discussed below) thereon.

In a preferred embodiment, as additionally shown in FIGS. 15B and 15D, the proximal end 504a of the access sleeve 502, i.e., planar region 503, further comprises two (2) threaded holes 505a, 505b, which are preferably disposed on opposing edge regions of the planar region 503. According to the invention, the threaded holes 505a, 505b are sized and configured to receive the threaded end 514 of the access sleeve handle 510, discussed below.

Figure 15F:
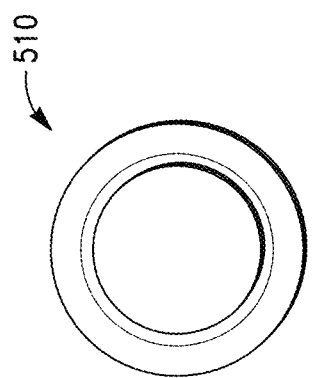
FIG. 15F is an end plan view of the access sleeve handle shown in FIG. 15E, in accordance with the invention.
Figure 15E:
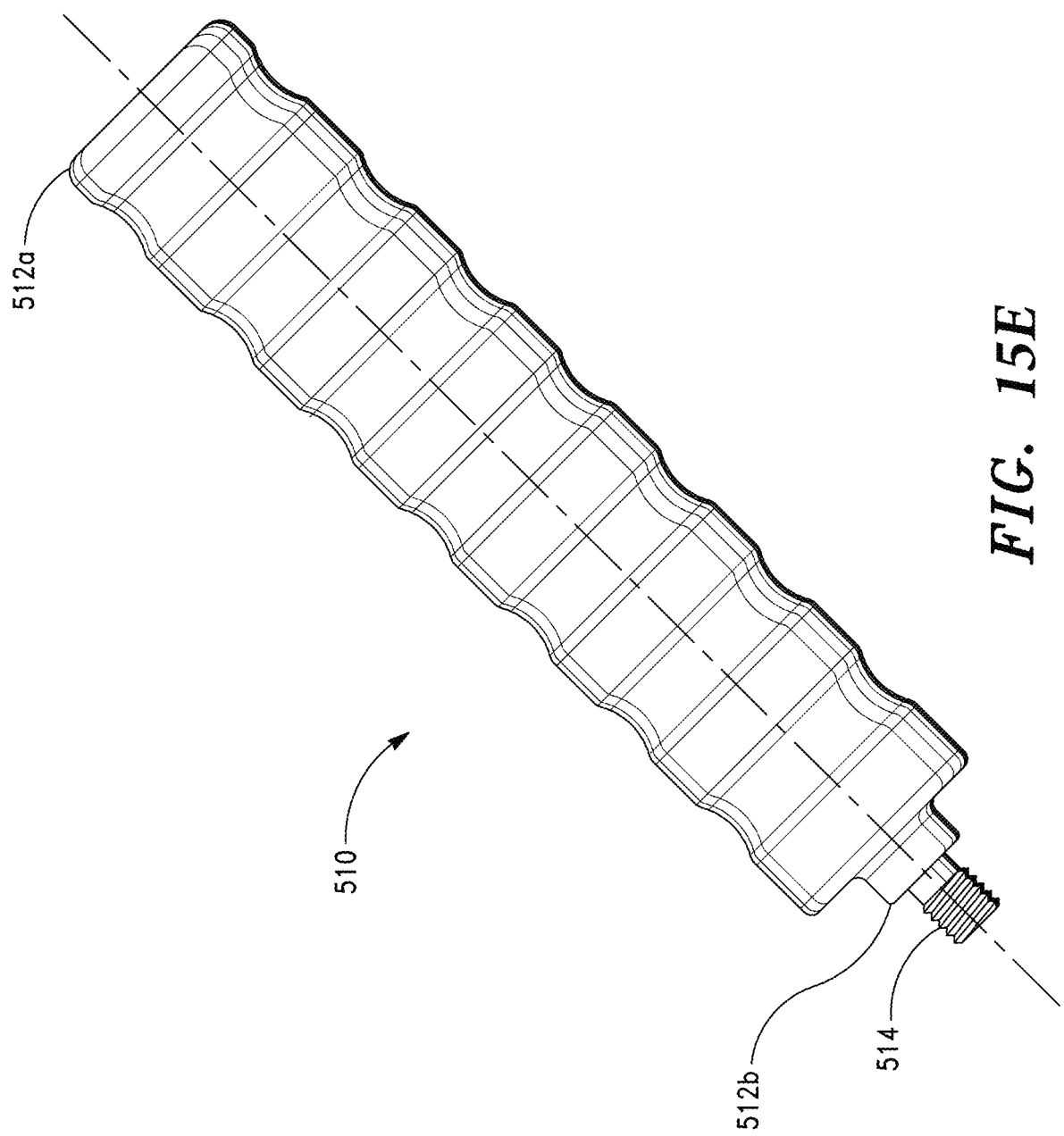
FIG. 15E is a perspective view of one embodiment of an access sleeve handle that is configured to engage the access sleeve shown in FIG. 15B, in accordance with the invention.
Figure 15H:
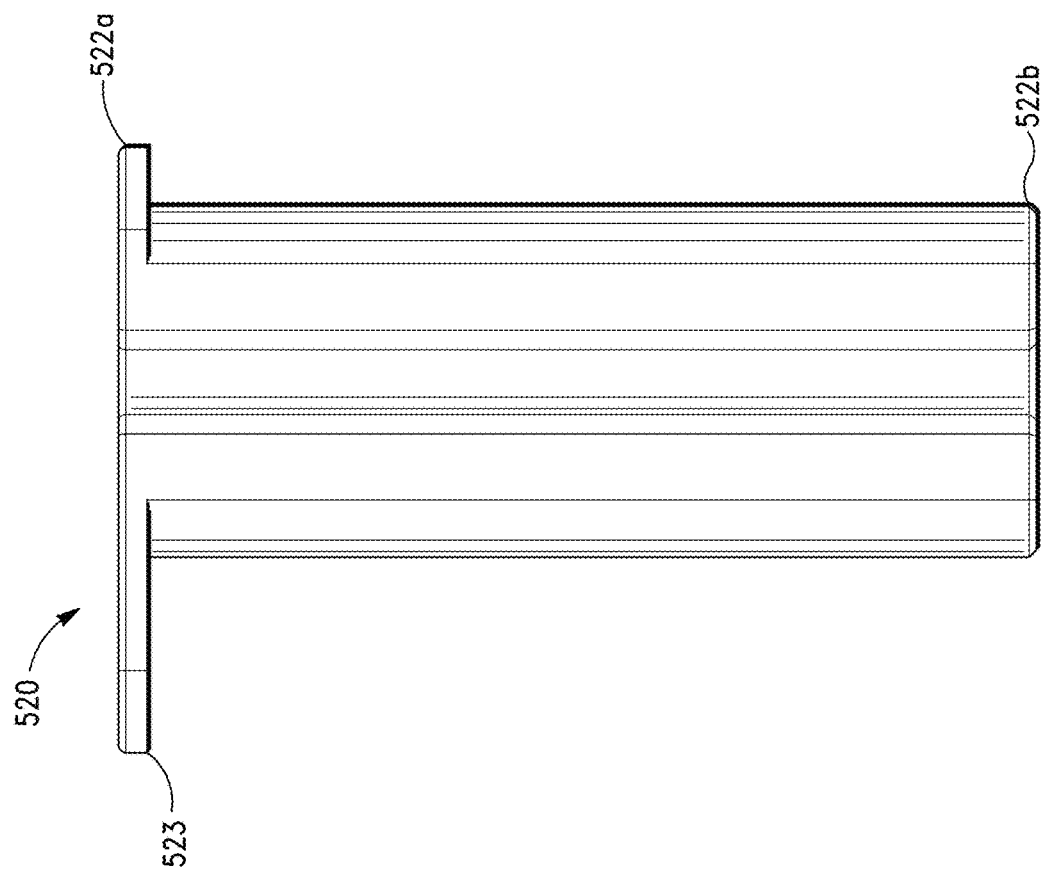
FIG. 15H is a front plan view of the drill guide shown in FIG. 15G, in accordance with the invention.
Figure 15G:
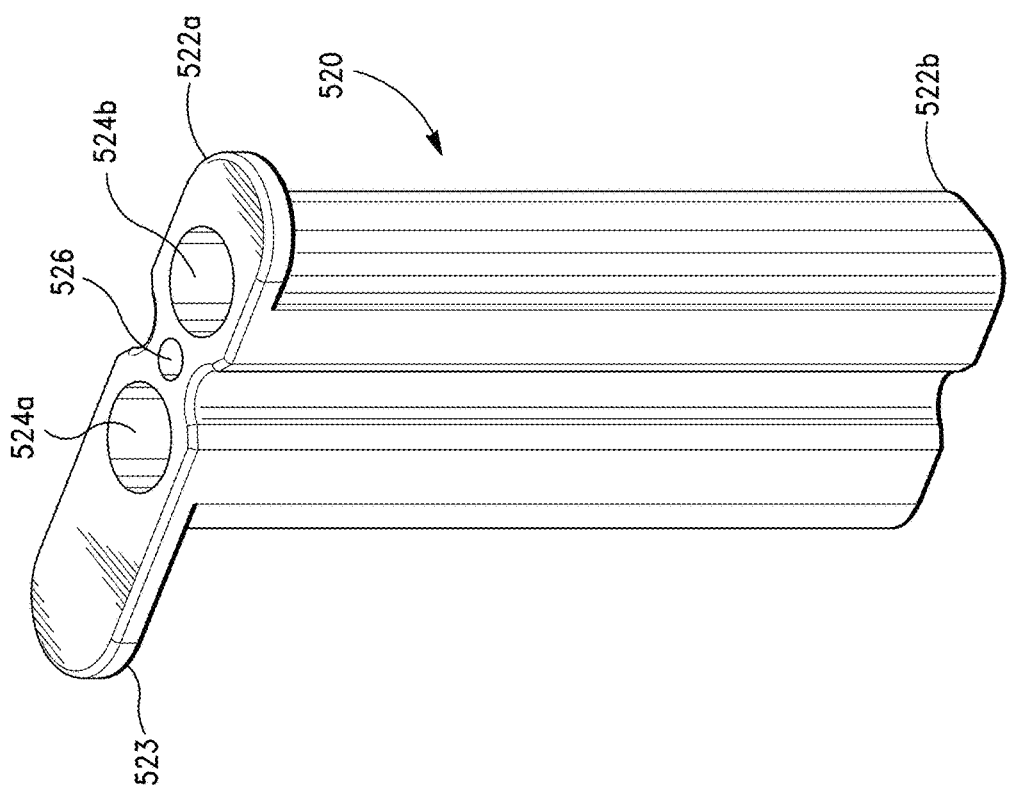
FIG. 15G is a perspective view of the drill guide of the drill guide assembly shown in FIG. 15A, in accordance with the invention.
Figure 15I:
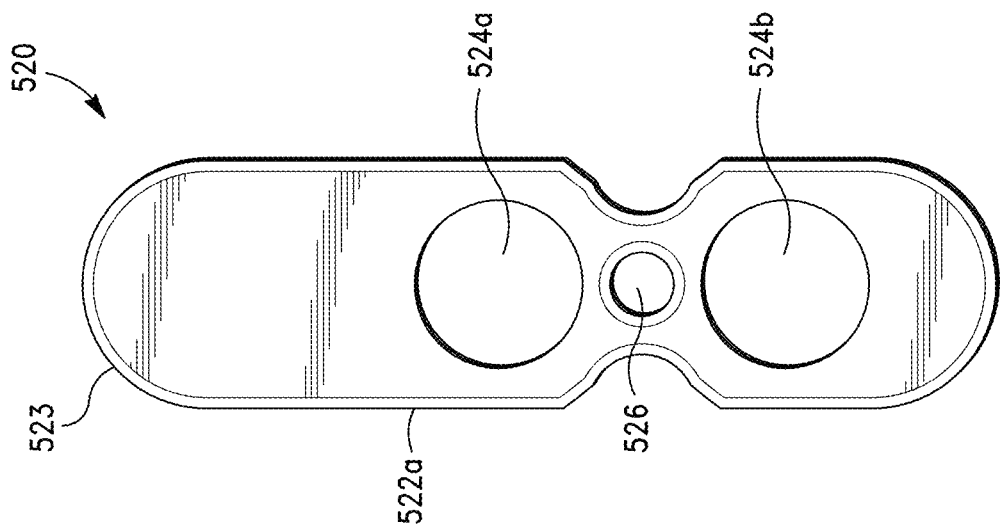
FIG. 15I is a top plan view of the drill guide shown in FIG. 15G, in accordance with the invention.
Figure 15J:
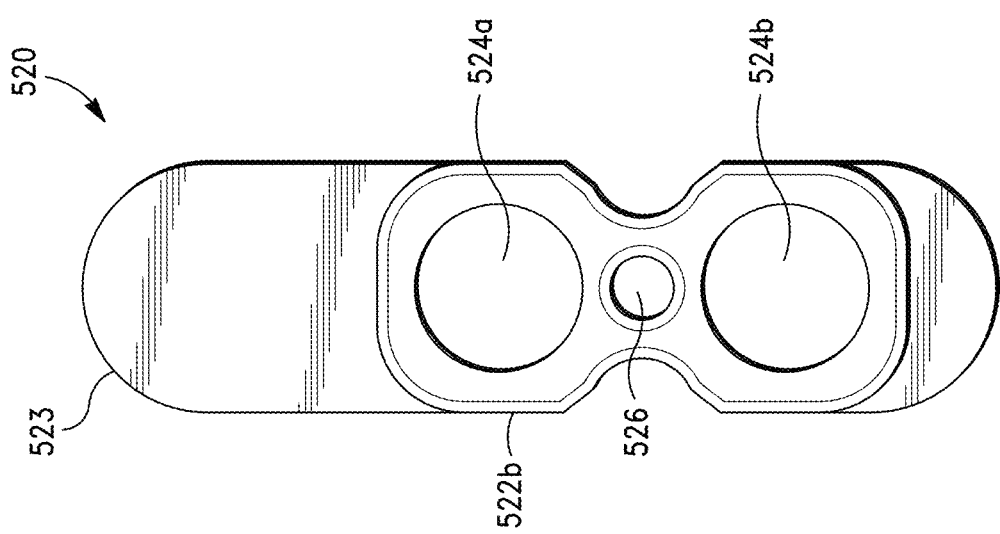
FIG. 15J is a bottom plan view of the drill guide shown in FIG. 15G, in accordance with the invention.

Referring now to FIGS. 15E and 15F, there is shown a preferred embodiment of the access sleeve handle 510.

As illustrated in FIGS. 15E and 15F, the access sleeve handle 510 preferably comprises an elongated cylindrical shaped member comprising proximal and distal ends 512a, 512b.

As further illustrated in FIG. 15E, in a preferred embodiment, the distal end 512b of the access sleeve handle 510 comprises a threaded extension 514 that is sized and configured to cooperate with the threaded holes 505a, 505b of the access sleeve 502, whereby the access sleeve handle 510 can be threadably engaged to the access sleeve 502.

Referring now to FIGS. 15G-15J, there is shown a preferred embodiment of the drill guide 520.

As illustrated in FIGS. 15E-15J, the drill guide 520 comprises proximal and distal ends 522a, 522b, a pair of drill guide lumens 524a, 524b and a drill guide medial lumen 526; the drill guide lumens 524a, 524b and drill guide medial lumen 526 extending from the proximal end 522a to the distal end 522b of the drill guide 520.

Figure 15L:
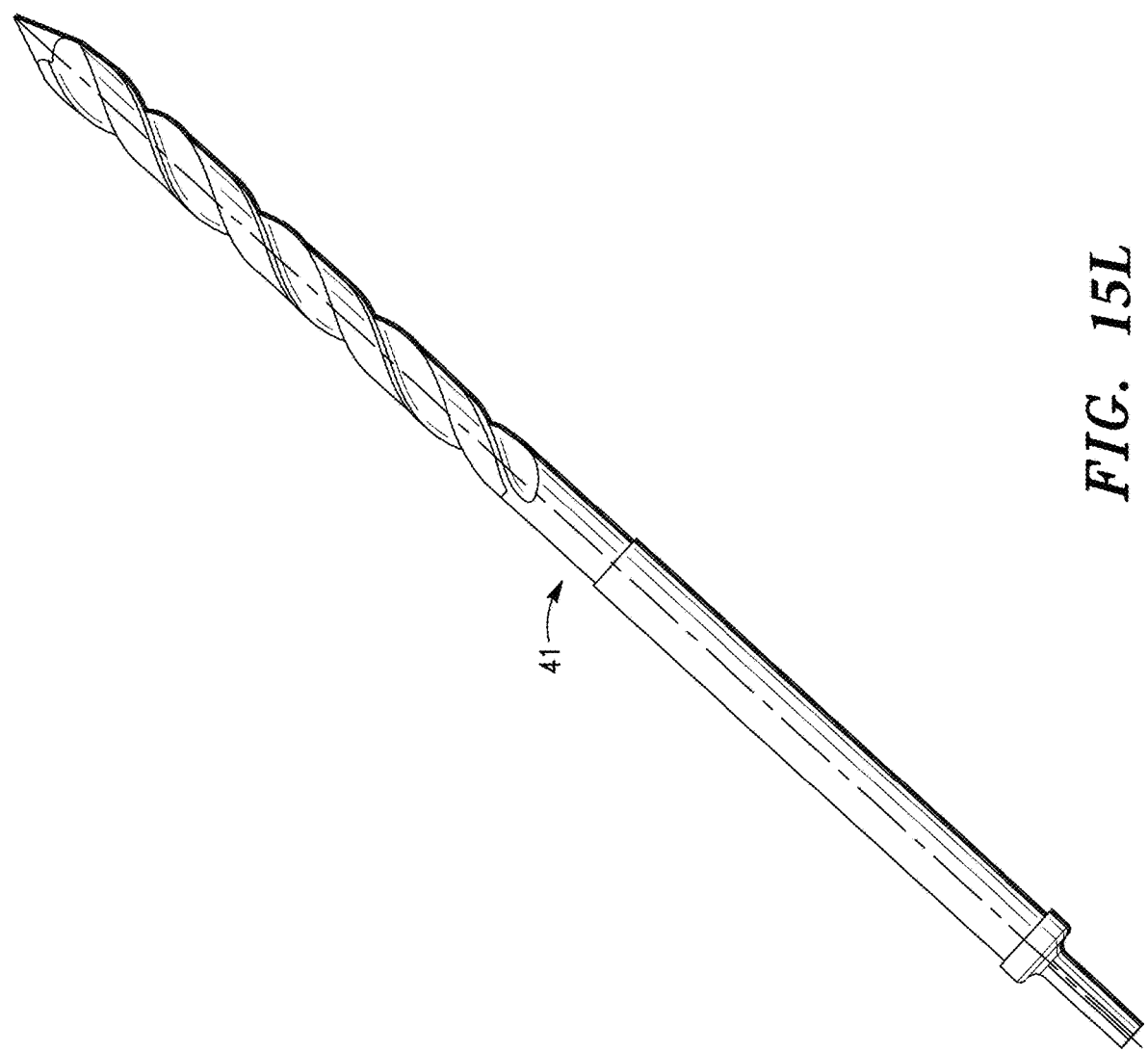
FIG. 15L is a perspective view of the bone dislodging apparatus, i.e., drill bit, shown in FIG. 15A, in accordance with the invention.

As illustrated in FIG. 15A, in a preferred embodiment, the drill guide lumens 524a, 524b are sized and configured to receive (i) a bone dislodging system 40 of the defect creation assembly 30, in this instance, the drill bit 41 shown in FIG. 15L, and (ii) the guide pin 530 shown in FIG. 15K discussed below.

In a preferred embodiment, the drill guide medial lumen 526 is sized and configured to receive and guide the elongated guide probe 20 of the invention to a desired position proximate the dysfunctional SI joint.

According to the invention, the drill guide internal lumens 524a, 524b and drill guide medial lumen 526 can also be sized and configured to receive various other suitable instruments, such as surgical scopes, center punches, location pins, drill probes and drill stop assemblies, to facilitate the creation of a pilot SI joint opening.

Referring back to FIGS. 15G and 15H, in a preferred embodiment, the proximal end 522a of the drill guide 520 comprises a planar configuration comprising an extended region 523, which, as illustrated in FIG. 15A, is sized and configured to abut the proximal end 504a of the access sleeve 502 to position the drill guide 520 therein.

Figure 15K:
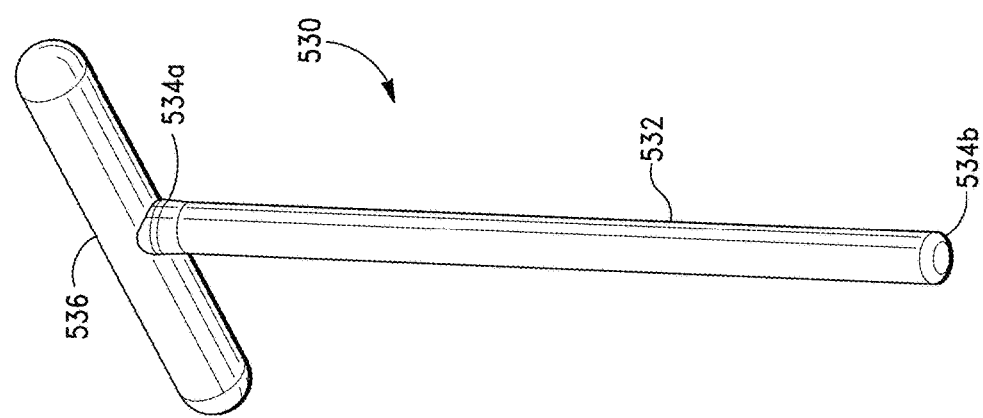
FIG. 15K is a perspective view of the guide pin of the drill guide assembly shown in FIG. 15A, in accordance with the invention.

Referring now to FIG. 15K, there is shown one embodiment of a guide pin 530 of the invention.

As illustrated in FIG. 15K, the guide pin 530 preferably comprises an elongated guide member 532 comprising proximal and distal ends 534a, 534b. The guide pin 530 further comprises a handle 536 that is operatively connected to the proximal end 534a of the guide member 532.

As further indicated above, in some embodiments, the system for stabilizing dysfunctional SI joints further comprises a prosthesis extraction assembly 600 that is configured and adapted to remove prosthesis 70a (and prostheses 70b, 70c, 70d, 70e, 70f, and 70g of the invention) from the expanded post-prosthesis insertion SI joint opening and, thereby, dysfunctional SI joint.

Referring now to FIGS. 16A-16G, there is shown a preferred embodiment of a prosthesis extraction assembly 600 of the invention with prosthesis 70a connected thereto.

Figure 16A:
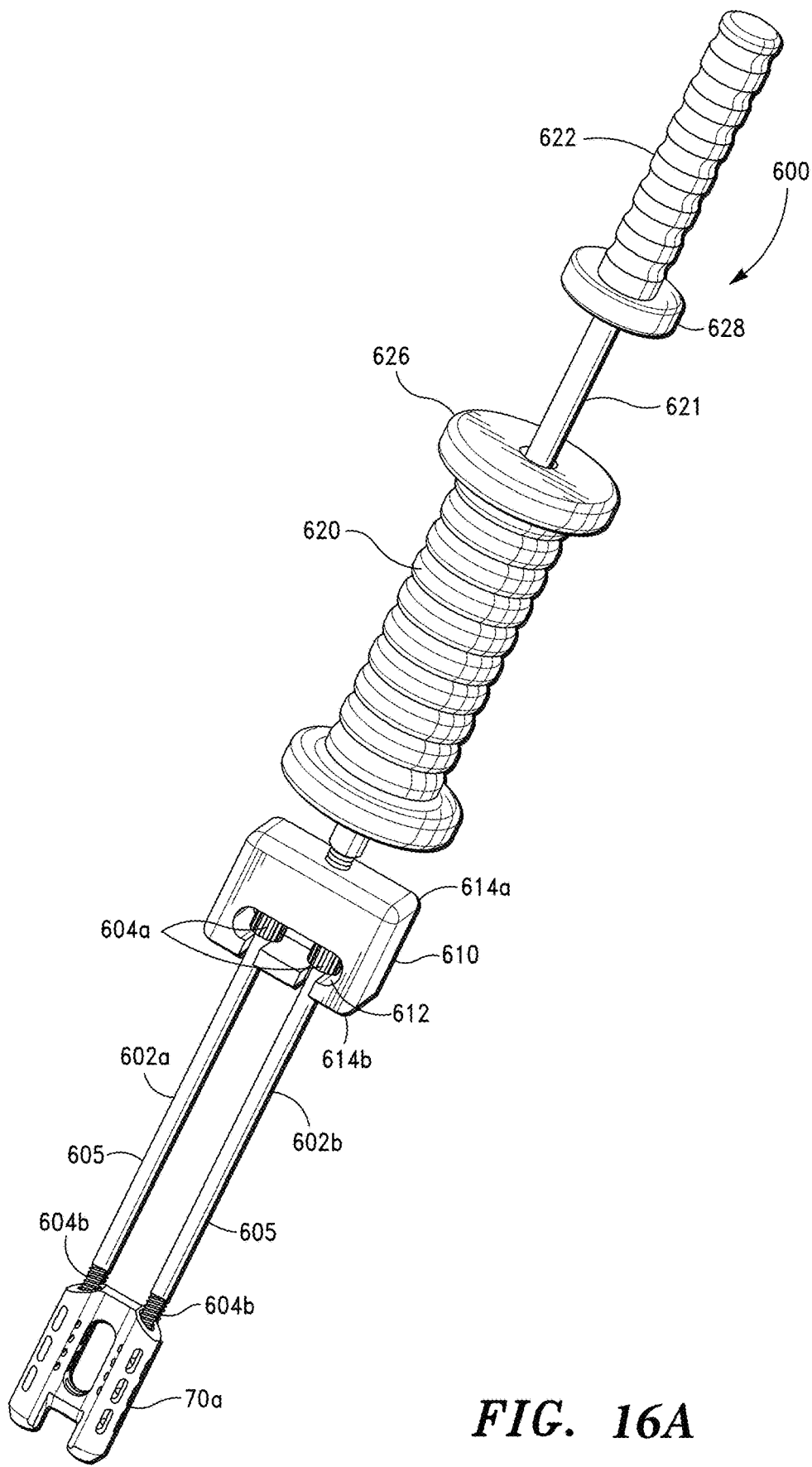
FIG. 16A is a perspective view of one embodiment of a prosthesis extraction assembly, in accordance with the invention.

As illustrated in FIG. 16A, the prosthesis extraction assembly 600 generally comprises prosthesis extraction rods or screws 602a, 602b, an extraction fork 610 and a slap hammer assembly 620.

Figure 16B:
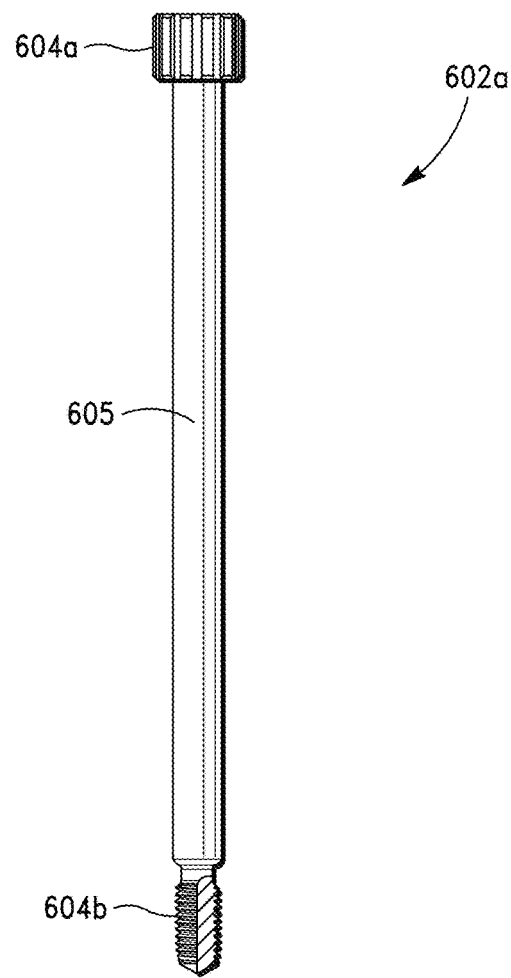
FIG. 16B is a front plan sectional view of the prosthesis extraction rod of the prosthesis extraction assembly shown in FIG. 16A, in accordance with the invention.
Figure 16C:
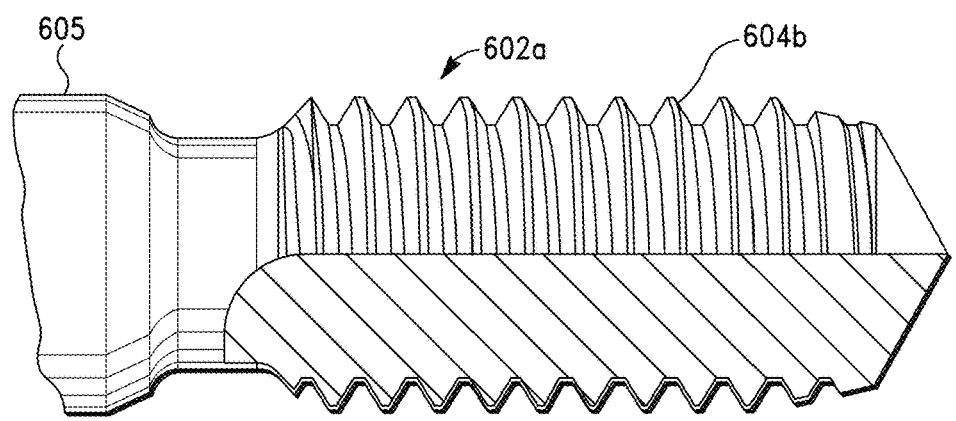
FIG. 16C is a partial section, front sectional plan view of the threaded end of the prosthesis extraction rod shown in FIG. 16B, in accordance with the invention.

As illustrated in FIGS. 16A-16C, the prosthesis extraction rods 602a, 602b comprise elongated rod members 605 comprising capped proximal ends 604a and threaded distal ends 604b, which, in the illustrated embodiment, are sized and configured to threadably engage threaded internal prosthesis engagement lumens 86a, 86b of the prosthesis 70a (and prostheses 70b, 70c, 70d, 70c, 70f, and 70g of the invention).

Figure 16D:
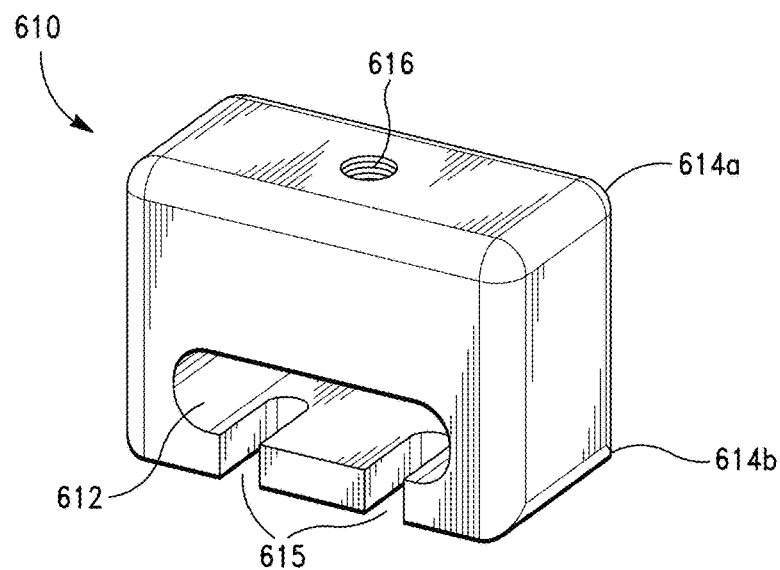
FIG. 16D is a perspective view of the extraction fork of the prosthesis extraction assembly shown in FIG. 16A, in accordance with the invention.
Figure 16E:
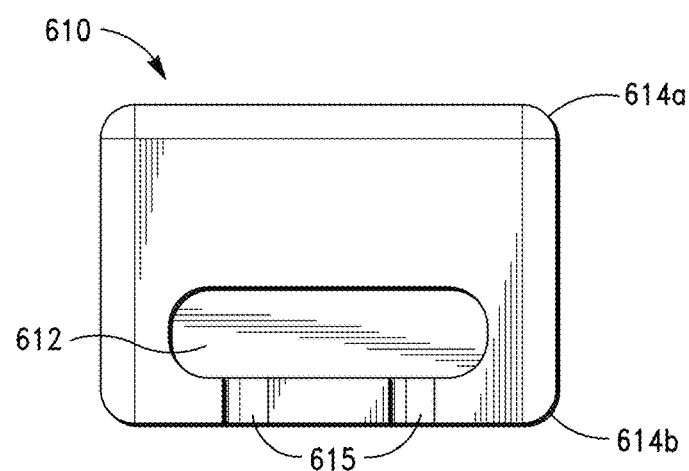
FIG. 16E is a front plan view of the extraction fork shown in FIG. 16D, in accordance with the invention.
Figure 16F:
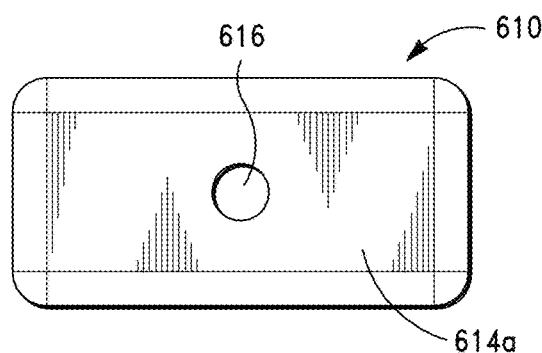
FIG. 16F is a top plan view of the extraction fork shown in FIG. 16D, in accordance with the invention.

As illustrated in FIGS. 16D-16F, the extraction fork 610 comprises proximal and distal ends 614a, 614b, a primary recess 612 and secondary recesses 615 proximate the distal end 614b. The extraction fork 610 further comprises a threaded lumen 616 proximate the proximal end 614a, which, as discussed below, is sized and configured to threadably engage the threaded distal end 624b of the elongated rod member 621 of the slap hammer assembly 620 discussed below.

As illustrated in FIG. 16A, in a preferred embodiment, the secondary recesses 615 of the extraction fork 610 are configured to receive and releasably engage or ensnare the capped proximal ends 604a of the prosthesis extraction rods 602a, 602b.

As further illustrated in FIG. 16A, the extraction fork 610 is further configured to releasably engage the threaded distal end 624b of the slap hammer assembly 620 via the threaded lumen 616.

Figure 16G:
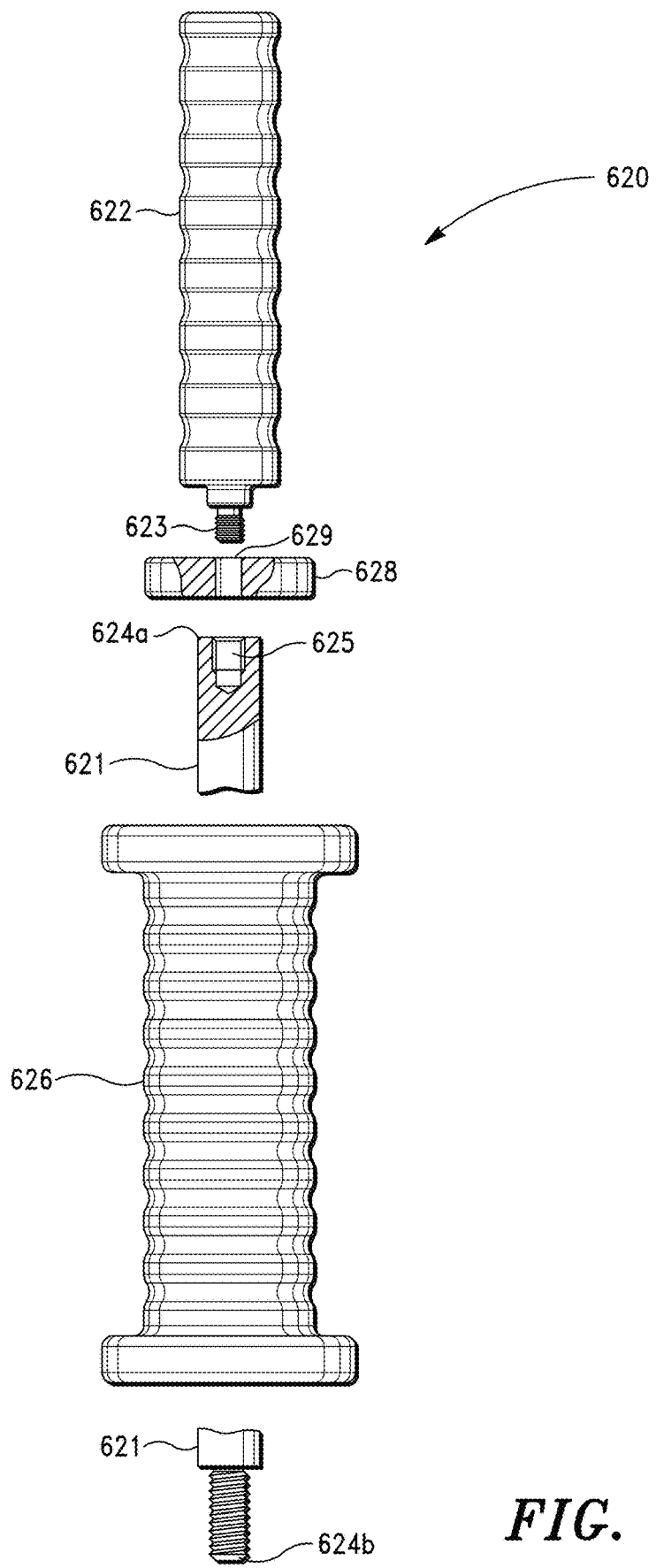
FIG. 16G is an exploded view of the slap hammer assembly of the prosthesis extraction assembly shown in FIG. 16A, in accordance with the invention.

As illustrated in FIGS. 16A and 16G, the slap hammer assembly 620 comprises a handle 622, an elongated rod member 621, a weighted sleeve member 626 and a bump stop 628.

As illustrated in FIG. 16G, the elongated rod member 621 comprises a proximal end 624a, comprising internal threads 625, and a threaded distal end 624b.

As further illustrated in FIG. 16G, the handle 622 comprises threaded distal end 623, which, as illustrated in FIG. 16A, is sized and configured to threadably engage the proximal end 624a of the elongated rod member 621.

As illustrated in FIG. 16A, the threaded distal end 623 of the handle 622 is further sized and configured to receive and seat the bump stop 628 thereon, wherein the bump stop 628 is securely positioned between the handle 622 and elongated rod member 621 when the handle 622 is engaged to the elongated rod member 621.

In a preferred embodiment, the weighted sleeve member 626 is configured to slidably translate along the elongated rod member 621 and abut the proximal end 614a of the extraction fork 610 and bump stop 628 when the slap hammer assembly 620 is releasably engaged to the extraction fork 610.

According to the invention, removal of prosthesis 70a (and prostheses 70b, 70c, 70d, 70c, 70f, and 70g of the invention) from the expanded post-prosthesis insertion SI joint opening is achieved as follows:

the prosthesis extraction rods 602a, 602b are initially connected to the prosthesis; and after the prosthesis extraction rods 602a, 602b are connected to the prosthesis, the surgeon grips the handle 622 of the prosthesis extraction assembly 600 and forcibly abuts the handle 622 against the bump stop 628, wherein a removal or extraction force is exerted on prosthesis via the prosthesis extraction rods 602a, 602b and the prosthesis is released from the expanded post-prosthesis insertion SI joint opening.

EXAMPLES

The following examples are provided to enable those skilled in the art to more clearly understand and practice the present invention. The examples should not be considered as limiting the scope of the invention, but merely as representative thereof.

Example 1

An adult male patient, age 55, presented with significant pain proximate his right SI joint. The patient had previously presented with a traumatic injury to the SI joint and a surgical dowel member was implanted in the SI joint to stabilize the joint.

A CT scan was performed to determine the basis for the patient's pain and check for any SI joint abnormalities. The CT scan indicated that the surgical dowel member had become dislodged and the SI joint was unstable and, hence, causing the pain that the patient was experiencing.

A stabilization procedure was thus performed in accord with the method set forth in Co-pending U.S. application Ser. No. 17/463,779. The specifics of the procedure were as follows:

Prosthesis

The prothesis selected for the procedure was similar to prosthesis 70b illustrated in FIGS. 9A and 9B, and described in detail above.

The prosthesis included a bone graft material, which was placed in the elongated sections of the prosthesis.

Incision

An incision was placed along the lateral lip of the posterior third of the iliac crest to the posterior superior spine to provide a prosthesis entry point into the SI joint.

Creation of Pilot SI Joint Opening

A pilot opening was created in the SI joint with the defect creation assembly shown in FIGS. 3B and 3C, and described above. The bone dislodging apparatus of the assembly comprised a drill assembly and associated drill bit.

The pilot opening that was created in the SI joint was similar to pilot SI joint opening 200 described above.

Prosthesis Placement in SI Joint

The prosthesis was advanced into the SI joint in a posterior trajectory toward the mid-point of the SI end plate and the sacral promontory.

The prothesis was positioned in the SI joint with the surgical dowel member disposed between and substantially parallel to the elongated members of the prosthesis, and approximately 5.0 mm ("d") from the central region of the bridge section, such as illustrated in FIG. 18, where the surgical dowel member is similarly denoted ("I").

Post-Procedure Assessment

Three (3) months after the joint stabilization procedure, the patient was evaluated by a specialist. CT scan images of the patient's SI joint were taken. A series of post procedure tests were also performed to determine the stability of the SI joint and mobility of the musculoskeletal structures of the pelvic and lumbar regions proximate the SI joint.

The CT scans reflected (i) secure and proper placement of the prosthesis in the SI joint, (ii) substantial solid bridging of osseous tissue, and, hence, bone across the SI joint and, (iii) substantial ossification around the prosthesis.

The post procedure tests were also very favorable. The patient tested positive to the flexion abduction and external rotation (FABER) test. The patient also responded very favorably to Gaenslen, thigh thrust, compression and distraction tests.

The tests thus confirmed that the SI joint was stabilized and that the musculoskeletal structures of the pelvic and lumbar regions proximate thereto were restored to a near normal level.

Example 2

An adolescent female patient, age 13, presented with scoliosis of the spine characterized by a curvature in the spine greater than 40.0°. The patient, who was a candidate for a posterior multilevel spinal fusion surgery procedure, underwent a posterior multilevel spinal fusion procedure, which included two (2) sacral-alar iliac (S2AI) screws that were placed in the left and right SI joints to stabilize the joint in conjunction with two (2) surgical rods and a series of pedicle screws.

Twelve (12) weeks after the procedure the patient complained of lower back pain proximate to a SI joint.

A CT scan was performed to determine the basis for the patient's pain and check for any SI joint abnormalities. The CT scan indicated that the sacral-alar iliac (S2AI) screw in the right SI joint was dislodged and the SI joint was unstable and, hence, likely causing the pain that the patient was experiencing.

A stabilization procedure was thus similarly performed in accord with the method set forth in Co-pending U.S. application Ser. No. 17/463,779.

Prosthesis

The prothesis selected for the procedure was similar to prosthesis 70e illustrated in FIGS. 12A and 12B, and described in detail above.

Incision

An incision was similarly placed along the lateral lip of the posterior third of the iliac crest to the posterior superior spine to provide a prosthesis entry point into the right SI joint through the posterior ligaments at approximately the S3 level.

Creation of Pilot SI Joint Opening

A pilot opening was created in the SI joint with the defect creation assembly shown in FIGS. 3B and 3C, and described above. The pilot SI joint opening was similar to pilot SI joint opening 200 described above.

Prosthesis Placement in SI Joint

The prosthesis was advanced through the incision and into the SI joint in a posterior trajectory toward the mid-point of the SI end plate and the sacral promontory.

Figure 19:
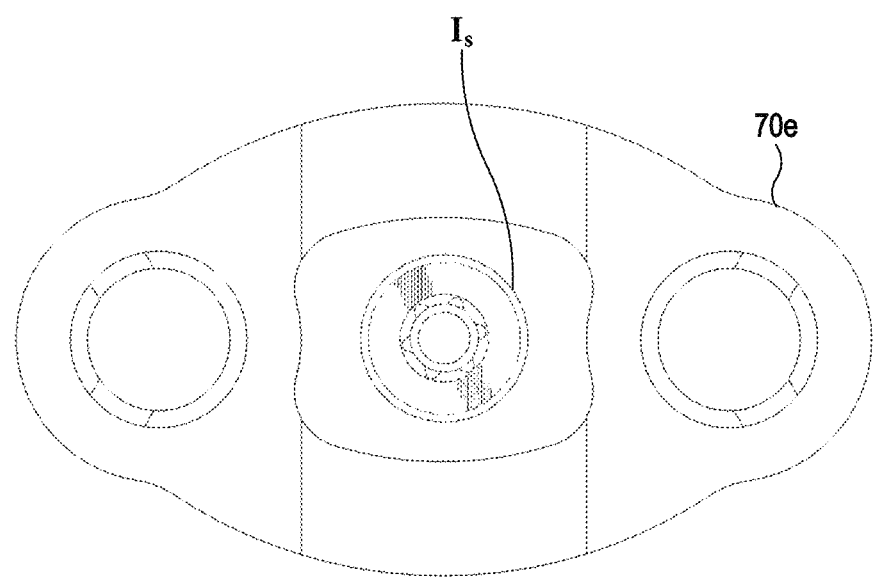
FIG. 19 is an illustration of the prosthesis shown in FIG. 12A with a surgical implant, i.e., orthopedic screw, disposed between the elongated sections thereof, in accordance with the invention.

The prothesis was positioned in the SI joint with the S2AI screw disposed between and substantially parallel to the elongated members of the prosthesis, and between the top and bottom bridge sections, as illustrated in FIG. 19, where the S2AI screw is denoted "Is".

Post-Procedure Assessment

Four (4) months after the joint stabilization procedure, the patient was evaluated by a specialist. CT scan images of the patient's SI joint were similarly taken. A series of post procedure tests were also performed to determine the stability of the SI joint and mobility of the musculoskeletal structures of the pelvic and lumbar regions proximate the SI joint.

The CT scans similarly reflected (i) secure and proper placement of the prosthesis in the SI joint, (ii) substantial solid bridging of osseous tissue, and, hence, bone across the SI joint and, (iii) substantial ossification around the prosthesis.

The post procedure tests were similarly very favorable. The patient also tested positive to the flexion abduction and external rotation (FABER) test, and responded very favorably to Gaenslen, thigh thrust, compression and distraction tests.

The tests thus confirmed that the SI joint was stabilized and that the musculoskeletal structures of the pelvic and lumbar regions proximate thereto were restored to a near normal level.

As will readily be appreciated by one having ordinary skill in the art, the present invention provides numerous advantages compared to prior art methods and apparatus for stabilizing dysfunctional SI joints. Among the advantages are the following:

the provision of improved SI joint stabilization systems and apparatus, which can be readily employed in minimally-invasive SI joint stabilization procedures to stabilize dysfunctional SI joints via a posterior approach;

the provision of improved SI joint prostheses, which, when implanted in a dysfunctional SI joint, effectively ameliorate pain associated with the SI joint dysfunction;

the provision of improved SI joint prostheses, which can readily be employed in minimally-invasive SI joint stabilization procedures and provide secure engagement to SI joint structures;

the provision of improved SI joint prostheses, which can readily be employed in minimally-invasive SI joint stabilization procedures and provide supplemental stabilization of SI joint structures with prior implants, such as a sacral-alar iliac (S2AI) screw or surgical dowel member;

the provision of improved SI joint prostheses, which can readily be employed in conjunction with surgical or orthopedic pins, dowels and screws to provide enhanced stabilization of SI joint structures;

the provision of improved SI joint prostheses, which can readily be employed in minimally-invasive SI joint stabilization procedures and possess optimal structural properties to effectively stabilize dysfunctional SI joints; and the provision of improved SI joint prostheses, which can readily be employed in minimally-invasive SI joint stabilization methods and facilitate remodeling of damaged osseous tissue and regeneration of new osseous tissue and osseous tissue structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An apparatus for stabilizing a dysfunctional sacroiliac (SI) joint, said dysfunctional SI joint comprising a sacrum bone structure, an ilium bone structure and an intraarticular region disposed between said sacrum bone structure and said ilium bone structure, said apparatus comprising:

a monolithic member configured and adapted to be advanced into said dysfunctional SI joint in a posterior trajectory, said monolithic member further adapted to transfix said dysfunctional SI joint when said monolithic member is said advanced into said dysfunctional SI joint, said monolithic member comprising a first elongated cylindrical shaped section, a second elongated cylindrical shaped section and a bridge section, said bridge section disposed between said first elongated section and said second elongated section and not extending beyond said first elongated section and said second elongated section in a longitudinal direction, said first elongated cylindrical shaped section configured to be advanced into said sacrum bone structure when said monolithic member is said advanced into said dysfunctional SI joint in said posterior trajectory, said first elongated cylindrical shaped section comprising a first open proximal end, a first distal end and a first tapered region disposed on said first distal end, said second elongated cylindrical shaped section configured to be advanced into said ilium bone structure when said monolithic member is said advanced into said dysfunctional SI joint in said posterior trajectory, said second elongated cylindrical shaped section comprising a second open proximal end, a second distal end and a second tapered region disposed on said second distal end, said bridge section adapted to be advanced into at least said intraarticular region of said SI joint when said monolithic member is said advanced into said dysfunctional SI joint in said posterior trajectory, wherein said bridge section is configured to traverse said sacrum bone structure, said intraarticular region and said ilium bone structure of said dysfunctional SI joint, said bridge section comprising a first proximal end and a third distal end disposed opposite said first proximal end, said bridge section comprising an ovate-shaped open bridge structure comprising a top bridge member and a separate bottom bridge member, said top bridge member and said bottom bridge member defining an open region between said top bridge member and said bottom bridge member, said monolithic member comprising a first interface of said top bridge member at a first top region of said first elongated cylindrical shaped section and a second interface of said bottom bridge member and at a first bottom region of said first elongated cylindrical shaped section, said first interface and said second interface being spaced a first distance apart, and a third interface of said top bridge member at a second top region of said second elongated cylindrical shaped section and a fourth interface of said bottom bridge member at a second bottom region of said second elongated cylindrical shaped section, said third interface and said fourth interface being spaced a second distance apart, said top bridge member of said ovate-shaped open bridge structure comprising a second proximal end, a fourth distal end and a third tapered region disposed on said fourth distal end, said top bridge member of said ovate-shaped open bridge structure further comprising a first elongate opening disposed between said second proximal end of said top bridge member and said fourth distal end of said top bridge member and extending through said top bridge member, said bottom bridge member of said ovate-shaped open bridge structure comprising a third proximal end, a fifth distal end and a fourth tapered region disposed on said fifth distal end.

2. The apparatus of claim 1, wherein said first elongated cylindrical shaped section of said monolithic member further comprises a first plurality of slots.

3. The apparatus of claim 2, wherein said first elongated cylindrical shaped section further comprises a first internal lumen in communication with said first open proximal end and said first plurality of slots of said first elongated cylindrical shaped section, said first internal lumen adapted to receive a first osteogenic composition therein.

4. The apparatus of claim 1, wherein said second elongated cylindrical shaped section of said monolithic member further comprises a second plurality of slots.

5. The apparatus of claim 4, wherein said second elongated cylindrical shaped section further comprises a second internal lumen in communication with said second open proximal end and said second plurality of slots of said second elongated cylindrical shaped section, said second internal lumen adapted to receive a second osteogenic composition therein.

6. The apparatus of claim 1, wherein said bottom bridge member of said ovate-shaped open bridge structure further comprises a second elongate opening disposed between said third proximal end and said fifth distal end of said bottom bridge member and extending through said bottom bridge member.

7. The apparatus of claim 1, wherein said top bridge member extends beyond said first interface of said top bridge member at said first top region of said first elongated cylindrical shaped section and said third interface of said top bridge member at said second top region of said second elongated cylindrical shaped section in a first vertical direction and said bottom bridge member extends beyond said second interface of said bottom bridge member and at said first bottom region of said first elongated cylindrical shaped section and said fourth interface of said bottom bridge member at said second bottom region of said second elongated cylindrical shaped section in a second vertical direction.

* * * * *